US012727766B2

(12) United States Patent
Al-Ali et al.

(10) Patent No.: US 12,727,766 B2
(45) Date of Patent: Sep. 8, 2026

(54) WEARABLE MONITORING DEVICE

(71) Applicant: Masimo Corporation, Irvine, CA (US)

(72) Inventors: Ammar Al-Ali, San Juan Capistrano, CA (US); Richard Priddell, Irvine, CA (US); Erik Karl Kinast, Santa Ana, CA (US); Stephen Scruggs, Newport Beach, CA (US); Nicolsson Fernandes, Pasadena, CA (US); Maxwell Gilmore, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 280 days.

(21) Appl. No.: 18/583,725

(22) Filed: Feb. 21, 2024

(65) Prior Publication Data

US 2024/0277280 A1 Aug. 22, 2024

Related U.S. Application Data

(60) Provisional application No. 63/486,456, filed on Feb. 22, 2023.

(51) Int. Cl.
*H01R 13/24* (2006.01)
*A61B 5/00* (2006.01)
(Continued)

(52) U.S. Cl.
CPC ............ *A61B 5/01* (2013.01); *A61B 5/02055* (2013.01); *A61B 5/256* (2021.01); *A61B 5/28* (2021.01);
(Continued)

(58) Field of Classification Search
CPC ....... A61B 5/01; A61B 5/02055; A61B 5/256; A61B 5/28; A61B 5/303; A61B 5/308;
(Continued)

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

WO WO 2019/027700 2/2019
WO WO 2024/178152 8/2024

OTHER PUBLICATIONS

US 2024/0016391 A1, 01/2024, Lapotko et al. (withdrawn)
International Search Report and Written Opionion in PCT application No. PCT/US2024/016772, dated May 17, 2024, pp. 22.

*Primary Examiner* — Abdullah A Riyami
*Assistant Examiner* — Nelson R. Burgos-Guntin
(74) *Attorney, Agent, or Firm* — Knobbe, Martens, Olson & Bear, LLP

(57) ABSTRACT

A wearable device configured to measure physiological parameters of a subject is described. The wearable device can include a dock having a plurality of prongs, a dock circuit layer having a plurality of conductive strips positioned along the plurality of prongs, and a plurality of electrodes in electrical communication with the dock circuit layer. The wearable device can also include a hub configured to be removably secured to the dock, the hub having a housing with a plurality of openings, and a hub circuit layer arranged within the interior of the housing. When the hub and dock are secured to one another, the plurality of prongs of the frame extend towards the plurality of openings of the housing of the hub and cause the plurality of conductive strips to contact portions of the hub circuit layer to facilitate electrical communication between the plurality of electrodes and the hub circuit layer.

27 Claims, 26 Drawing Sheets

(51) Int. Cl.
*A61B 5/01* (2006.01)
*A61B 5/0205* (2006.01)
*A61B 5/256* (2021.01)
*A61B 5/28* (2021.01)
*A61B 5/30* (2021.01)
*A61B 5/308* (2021.01)
*A61B 5/332* (2021.01)

(52) U.S. Cl.
CPC .............. *A61B 5/303* (2021.01); *A61B 5/308* (2021.01); *A61B 5/332* (2021.01); *A61B 5/6832* (2013.01); *A61B 2560/0214* (2013.01); *A61B 2562/222* (2013.01); *A61B 2562/227* (2013.01)

(58) Field of Classification Search
CPC .................. A61B 5/332; A61B 5/6832; A61B 2560/0214; A61B 2562/222; A61B 2562/227; A61B 2562/0271; A61B 5/0008; A61B 5/259; A61B 5/447; A61B 2560/0443; A61B 2562/16; A61B 5/0006; A61B 5/6833; A61B 5/282; A61B 5/6823; H01R 12/714; H01R 13/2442; H01R 2201/12; H01R 13/15; H01R 13/00; H01R 12/00
See application file for complete search history.

(56) References Cited

U.S. PATENT DOCUMENTS 5,319,355 A 6/1994 Russek
5,337,744 A 8/1994 Branigan
5,341,805 A 8/1994 Stavridi et al.
5,377,676 A 1/1995 Vari et al.
5,431,170 A 7/1995 Mathews
5,436,499 A 7/1995 Namavar et al.
5,456,252 A 10/1995 Vari et al.
5,479,934 A 1/1996 Imran
5,482,036 A 1/1996 Diab et al.
5,494,043 A 2/1996 O'Sullivan et al.
5,533,511 A 7/1996 Kaspari et al.
5,590,649 A 1/1997 Caro et al.
5,602,924 A 2/1997 Durand et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,890,929 A 4/1999 Mills et al.
5,919,134 A 7/1999 Diab
5,987,343 A 11/1999 Kinast
5,997,343 A 12/1999 Mills et al.
6,002,952 A 12/1999 Diab et al.
6,010,937 A 1/2000 Karam et al.
6,027,452 A 2/2000 Flaherty et al.
6,040,578 A 3/2000 Malin et al.
6,066,204 A 5/2000 Haven
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,152,754 A 11/2000 Gerhardt et al.
6,184,521 B1 2/2001 Coffin, IV et al.
6,232,609 B1 5/2001 Snyder et al.
6,241,683 B1 6/2001 Macklem et al.
6,253,097 B1 6/2001 Aronow et al.
6,255,708 B1 7/2001 Sudharsanan et al.
6,280,381 B1 8/2001 Malin et al.
6,285,896 B1 9/2001 Tobler et al.
6,308,089 B1 10/2001 von der Ruhr et al.
6,317,627 B1 11/2001 Ennen et al.
6,321,100 B1 11/2001 Parker
6,334,065 B1 12/2001 Al-Ali et al.
6,360,114 B1 3/2002 Diab et al.
6,368,283 B1 4/2002 Xu et al.
6,411,373 B1 6/2002 Garside et al.
6,415,167 B1 7/2002 Blank et al.
6,430,437 B1 8/2002 Marro
6,430,525 B1 8/2002 Weber et al.
6,463,311 B1 10/2002 Diab
6,470,199 B1 10/2002 Kopotic et al.
6,487,429 B2 11/2002 Hockersmith et al.
6,505,059 B1 1/2003 Kollias et al.
6,525,386 B1 2/2003 Mills et al.
6,526,300 B1 2/2003 Kiani et al.
6,534,012 B1 3/2003 Hazen et al.
6,542,764 B1 4/2003 Al-Ali et al.
6,580,086 B1 6/2003 Schulz et al.
6,584,336 B1 6/2003 Ali et al.
6,587,196 B1 7/2003 Stippick et al.
6,587,199 B1 7/2003 Luu
6,597,932 B2 7/2003 Tian et al.
6,606,511 B1 8/2003 Ali et al.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,658,276 B2 12/2003 Kiani et al.
6,661,161 B1 12/2003 Lanzo et al.
6,697,656 B1 2/2004 Al-Ali
6,697,658 B2 2/2004 Al-Ali
RE38,476 E 3/2004 Diab et al.
RE38,492 E 4/2004 Diab et al.
6,738,652 B2 5/2004 Mattu et al.
6,760,607 B2 7/2004 Al-Ali
6,788,965 B2 9/2004 Ruchti et al.
6,816,241 B2 11/2004 Grubisic
6,822,564 B2 11/2004 Al-Ali
6,850,787 B2 2/2005 Weber et al.
6,850,788 B2 2/2005 Al-Ali
6,876,931 B2 4/2005 Lorenz et al.
6,920,345 B2 7/2005 Al-Ali et al.
6,934,570 B2 8/2005 Kiani et al.
6,943,348 B1 9/2005 Coffin IV
6,956,649 B2 10/2005 Acosta et al.
6,961,598 B2 11/2005 Diab
6,970,792 B1 11/2005 Diab
6,985,764 B2 1/2006 Mason et al.
6,990,364 B2 1/2006 Ruchti et al.
6,998,247 B2 2/2006 Monfre et al.
7,003,338 B2 2/2006 Weber et al.
7,015,451 B2 3/2006 Dalke et al.
7,027,849 B2 4/2006 Al-Ali
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,133,710 B2 11/2006 Acosta et al.
7,142,901 B2 11/2006 Kiani et al.
7,225,006 B2 5/2007 Al-Ali et al.
RE39,672 E 6/2007 Shehada et al.
7,254,429 B2 8/2007 Schurman et al.
7,254,431 B2 8/2007 Al-Ali et al.
7,254,434 B2 8/2007 Schulz et al.
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,341,559 B2 3/2008 Schulz et al.
7,343,186 B2 3/2008 Lamego et al.
D566,282 S 4/2008 Al-Ali et al.
7,356,365 B2 4/2008 Schurman
7,371,981 B2 5/2008 Abdul-Hafiz
7,373,193 B2 5/2008 Al-Ali et al.

(56) References Cited

U.S. PATENT DOCUMENTS 7,377,794 B2 5/2008 Al-Ali et al.
7,395,158 B2 7/2008 Monfre et al.
7,415,297 B2 8/2008 Al-Ali et al.
7,438,683 B2 10/2008 Al-Ali et al.
7,483,729 B2 1/2009 Al-Ali et al.
D587,657 S 3/2009 Al-Ali et al.
7,500,950 B2 3/2009 Al-Ali et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
D592,507 S 5/2009 Wachman et al.
7,530,942 B1 5/2009 Diab
7,593,230 B2 9/2009 Abul-Haj et al.
7,596,398 B2 9/2009 Al-Ali et al.
7,606,608 B2 10/2009 Blank et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,761,127 B2 7/2010 Al-Ali et al.
7,764,982 B2 7/2010 Dalke et al.
D621,516 S 8/2010 Kiani et al.
7,791,155 B2 9/2010 Diab
RE41,912 E 11/2010 Parker
7,880,626 B2 2/2011 Al-Ali et al.
7,909,772 B2 3/2011 Popov et al.
7,919,713 B2 4/2011 Al-Ali et al.
7,937,128 B2 5/2011 Al-Ali
7,937,129 B2 5/2011 Mason et al.
7,941,199 B2 5/2011 Kiani
7,957,780 B2 6/2011 Lamego et al.
7,962,188 B2 6/2011 Kiani et al.
7,976,472 B2 7/2011 Kiani
7,990,382 B2 8/2011 Kiani
8,008,088 B2 8/2011 Bellott et al.
RE42,753 E 9/2011 Kiani-Azarbayjany et al.
8,028,701 B2 10/2011 Al-Ali et al.
8,048,040 B2 11/2011 Kiani
8,050,728 B2 11/2011 Al-Ali et al.
RE43,169 E 2/2012 Parker
8,118,620 B2 2/2012 Al-Ali et al.
8,130,105 B2 3/2012 Al-Ali et al.
8,182,443 B1 5/2012 Kiani
8,190,223 B2 5/2012 Al-Ali et al.
8,203,438 B2 6/2012 Kiani et al.
8,203,704 B2 6/2012 Merritt et al.
8,219,172 B2 7/2012 Schurman et al.
8,224,411 B2 7/2012 Al-Ali et al.
8,229,532 B2 7/2012 Davis
8,233,955 B2 7/2012 Al-Ali et al.
8,255,026 B1 8/2012 Al-Ali
8,265,723 B1 9/2012 McHale et al.
8,274,360 B2 9/2012 Sampath et al.
8,280,473 B2 10/2012 Al-Ali
8,315,683 B2 11/2012 Al-Ali et al.
RE43,860 E 12/2012 Parker
8,346,330 B2 1/2013 Lamego
8,353,842 B2 1/2013 Al-Ali et al.
8,355,766 B2 1/2013 MacNeish, III et al.
8,374,665 B2 2/2013 Lamego
8,388,353 B2 3/2013 Kiani et al.
8,401,602 B2 3/2013 Kiani
8,414,499 B2 4/2013 Al-Ali et al.
8,418,524 B2 4/2013 Al-Ali
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,707 B2 6/2013 Kiani
8,471,713 B2 6/2013 Poeze et al.
8,473,020 B2 6/2013 Kiani et al.
8,509,867 B2 8/2013 Workman et al.
8,515,509 B2 8/2013 Bruinsma et al.
8,523,781 B2 9/2013 Al-Ali
D692,145 S 10/2013 Al-Ali et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,584,345 B2 11/2013 Al-Ali et al.
8,588,880 B2 11/2013 Abdul-Hafiz et al.
8,630,691 B2 1/2014 Lamego et al.
8,641,631 B2 2/2014 Sierra et al.
8,652,060 B2 2/2014 Al-Ali
8,666,468 B1 3/2014 Al-Ali
8,670,811 B2 3/2014 O'Reilly
RE44,823 E 4/2014 Parker
RE44,875 E 4/2014 Kiani et al.
8,688,183 B2 4/2014 Bruinsma et al.
8,690,799 B2 4/2014 Telfort et al.
8,702,627 B2 4/2014 Telfort et al.
8,712,494 B1 4/2014 MacNeish, III et al.
8,715,206 B2 5/2014 Telfort et al.
8,723,677 B1 5/2014 Kiani
8,740,792 B1 6/2014 Kiani et al.
8,755,535 B2 6/2014 Telfort et al.
8,755,872 B1 6/2014 Marinow
8,764,671 B2 7/2014 Kiani
8,768,423 B2 7/2014 Shakespeare et al.
8,771,204 B2 7/2014 Telfort et al.
8,781,544 B2 7/2014 Al-Ali et al.
8,790,268 B2 7/2014 Al-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,840,549 B2 9/2014 Al-Ali et al.
8,852,094 B2 10/2014 Al-Ali et al.
8,852,994 B2 10/2014 Wojtczuk et al.
8,897,847 B2 11/2014 Al-Ali
8,911,377 B2 12/2014 Al-Ali
8,989,831 B2 3/2015 Al-Ali et al.
8,998,809 B2 4/2015 Kiani
9,066,666 B2 6/2015 Kiani
9,066,680 B1 6/2015 Al-Ali et al.
9,095,316 B2 8/2015 Welch et al.
9,106,038 B2 8/2015 Telfort et al.
9,107,625 B2 8/2015 Telfort et al.
9,131,881 B2 9/2015 Diab et al.
9,138,180 B1 9/2015 Coverston et al.
9,153,112 B1 10/2015 Kiani et al.
9,192,329 B2 11/2015 Al-Ali
9,192,351 B1 11/2015 Telfort et al.
9,195,385 B2 11/2015 Al-Ali et al.
9,211,095 B1 12/2015 Al-Ali
9,218,454 B2 12/2015 Kiani et al.
9,245,668 B1 1/2016 Vo et al.
9,267,572 B2 2/2016 Barker et al.
9,277,880 B2 3/2016 Poeze et al.
9,307,928 B1 4/2016 Al-Ali et al.
9,323,894 B2 4/2016 Kiani
D755,392 S 5/2016 Hwang et al.
9,326,712 B1 5/2016 Kiani
9,392,945 B2 7/2016 Al-Ali et al.
9,408,542 B1 8/2016 Kinast et al.
9,436,645 B2 9/2016 Al-Ali et al.
9,445,759 B1 9/2016 Lamego et al.
9,474,474 B2 10/2016 Lamego et al.
9,480,435 B2 11/2016 Olsen
9,510,779 B2 12/2016 Poeze et al.
9,517,024 B2 12/2016 Kiani et al.
9,532,722 B2 1/2017 Lamego et al.
9,560,996 B2 2/2017 Kiani
9,579,039 B2 2/2017 Jansen et al.
9,622,692 B2 4/2017 Lamego et al.

(56) References Cited

U.S. PATENT DOCUMENTS

D788,312 S 5/2017 Al-Ali et al.
9,649,054 B2 5/2017 Lamego et al.
9,697,928 B2 7/2017 Al-Ali et al.
9,717,458 B2 8/2017 Lamego et al.
9,724,016 B1 8/2017 Al-Ali et al.
9,724,024 B2 8/2017 Al-Ali
9,724,025 B1 8/2017 Kiani et al.
9,749,232 B2 8/2017 Sampath et al.
9,750,442 B2 9/2017 Olsen
9,750,461 B1 9/2017 Telfort
9,775,545 B2 10/2017 Al-Ali et al.
9,778,079 B1 10/2017 Al-Ali et al.
9,782,077 B2 10/2017 Lamego et al.
9,787,568 B2 10/2017 Lamego et al.
9,808,188 B1 11/2017 Perea et al.
9,839,379 B2 12/2017 Al-Ali et al.
9,839,381 B1 12/2017 Weber et al.
9,847,749 B2 12/2017 Kiani et al.
9,848,800 B1 12/2017 Lee et al.
9,861,298 B2 1/2018 Eckerbom et al.
9,861,305 B1 1/2018 Weber et al.
9,877,650 B2 1/2018 Muhsin et al.
9,891,079 B2 2/2018 Dalvi
9,924,897 B1 3/2018 Abdul-Hafiz
9,936,917 B2 4/2018 Poeze et al.
9,955,937 B2 5/2018 Telfort
9,965,946 B2 5/2018 Al-Ali et al.
D820,865 S 6/2018 Muhsin et al.
9,986,952 B2 6/2018 Dalvi et al.
D822,215 S 7/2018 Al-Ali et al.
D822,216 S 7/2018 Barker et al.
10,010,276 B2 7/2018 Al-Ali et al.
10,086,138 B1 10/2018 Novak, Jr.
10,111,591 B2 10/2018 Dyell et al.
D833,624 S 11/2018 DeJong et al.
10,123,729 B2 11/2018 Dyell et al.
D835,282 S 12/2018 Barker et al.
D835,283 S 12/2018 Barker et al.
D835,284 S 12/2018 Barker et al.
D835,285 S 12/2018 Barker et al.
10,149,616 B2 12/2018 Al-Ali et al.
10,154,815 B2 12/2018 Al-Ali et al.
10,159,412 B2 12/2018 Lamego et al.
10,188,348 B2 1/2019 Al-Ali et al.
RE47,218 E 2/2019 Al-Ali
RE47,244 E 2/2019 Kiani et al.
RE47,249 E 2/2019 Kiani et al.
10,205,291 B2 2/2019 Scruggs et al.
10,226,187 B2 3/2019 Al-Ali et al.
10,231,657 B2 3/2019 Al-Ali et al.
10,231,670 B2 3/2019 Blank et al.
RE47,353 E 4/2019 Kiani et al.
10,279,247 B2 5/2019 Kiani
10,292,664 B2 5/2019 Al-Ali
10,299,720 B2 5/2019 Brown et al.
10,327,337 B2 6/2019 Schmidt et al.
10,327,713 B2 6/2019 Barker et al.
10,332,630 B2 6/2019 Al-Ali
10,383,520 B2 8/2019 Wojtczuk et al.
10,383,527 B2 8/2019 Al-Ali
10,388,120 B2 8/2019 Muhsin et al.
D864,120 S 10/2019 Forrest et al.
10,441,181 B1 10/2019 Telfort et al.
10,441,196 B2 10/2019 Eckerbom et al.
10,448,844 B2 10/2019 Al-Ali et al.
10,448,871 B2 10/2019 Al-Ali et al.
10,456,038 B2 10/2019 Lamego et al.
10,463,340 B2 11/2019 Telfort et al.
10,471,159 B1 11/2019 Lapotko et al.
10,505,311 B2 12/2019 Al-Ali et al.
10,524,738 B2 1/2020 Olsen
10,532,174 B2 1/2020 Al-Ali
10,537,285 B2 1/2020 Shreim et al.
10,542,903 B2 1/2020 Al-Ali et al.
10,555,678 B2 2/2020 Dalvi et al.
10,568,553 B2 2/2020 O'Neil et al.
10,608,817 B2 3/2020 Haider et al.
D880,477 S 4/2020 Forrest et al.
10,617,302 B2 4/2020 Al-Ali et al.
10,617,335 B2 4/2020 Al-Ali et al.
10,637,181 B2 4/2020 Al-Ali et al.
D886,849 S 6/2020 Muhsin et al.
D887,548 S 6/2020 Abdul-Hafiz et al.
D887,549 S 6/2020 Abdul-Hafiz et al.
10,667,764 B2 6/2020 Ahmed et al.
D890,708 S 7/2020 Forrest et al.
10,721,785 B2 7/2020 Al-Ali
10,736,518 B2 8/2020 Al-Ali et al.
10,750,984 B2 8/2020 Pauley et al.
D897,098 S 9/2020 Al-Ali
10,779,098 B2 9/2020 Iswanto et al.
10,827,961 B1 11/2020 Iyengar et al.
10,828,007 B1 11/2020 Telfort et al.
10,832,818 B2 11/2020 Muhsin et al.
10,849,554 B2 12/2020 Shreim et al.
10,856,750 B2 12/2020 Indorf
D906,970 S 1/2021 Forrest et al.
D908,213 S 1/2021 Abdul-Hafiz et al.
10,918,281 B2 2/2021 Al-Ali et al.
10,932,705 B2 3/2021 Muhsin et al.
10,932,729 B2 3/2021 Kiani et al.
10,939,878 B2 3/2021 Kiani et al.
10,956,950 B2 3/2021 Al-Ali et al.
D916,135 S 4/2021 Indorf et al.
D917,046 S 4/2021 Abdul-Hafiz et al.
D917,550 S 4/2021 Indorf et al.
D917,564 S 4/2021 Indorf et al.
D917,704 S 4/2021 Al-Ali et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
11,006,867 B2 5/2021 Al-Ali
D921,202 S 6/2021 Al-Ali et al.
11,024,064 B2 6/2021 Muhsin et al.
11,026,604 B2 6/2021 Chen et al.
D925,597 S 7/2021 Chandran et al.
D927,699 S 8/2021 Al-Ali et al.
11,076,777 B2 8/2021 Lee et al.
11,114,188 B2 9/2021 Poeze et al.
D933,232 S 10/2021 Al-Ali et al.
D933,233 S 10/2021 Al-Ali et al.
D933,234 S 10/2021 Al-Ali et al.
11,145,408 B2 10/2021 Sampath et al.
11,147,518 B1 10/2021 Al-Ali et al.
11,185,262 B2 11/2021 Al-Ali et al.
11,191,484 B2 12/2021 Kiani et al.
D946,596 S 3/2022 Ahmed
D946,597 S 3/2022 Ahmed
D946,598 S 3/2022 Ahmed
D946,617 S 3/2022 Ahmed
11,272,839 B2 3/2022 Al-Ali et al.
11,289,199 B2 3/2022 Al-Ali
RE49,034 E 4/2022 Al-Ali
11,298,021 B2 4/2022 Muhsin et al.
D950,580 S 5/2022 Ahmed
D950,599 S 5/2022 Ahmed
D950,738 S 5/2022 Al-Ali et al.
D957,648 S 7/2022 Al-Ali
11,382,567 B2 7/2022 O'Brien et al.
11,389,093 B2 7/2022 Triman et al.
11,406,286 B2 8/2022 Al-Ali et al.
11,417,426 B2 8/2022 Muhsin et al.
11,439,329 B2 9/2022 Lamego
11,445,948 B2 9/2022 Scruggs et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
D971,933 S 12/2022 Ahmed
D973,072 S 12/2022 Ahmed
D973,685 S 12/2022 Ahmed
D973,686 S 12/2022 Ahmed

(56) References Cited

U.S. PATENT DOCUMENTS

D974,193 S 1/2023 Forrest et al.
D979,516 S 2/2023 Al-Ali et al.
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
D989,112 S 6/2023 Muhsin et al.
D989,327 S 6/2023 Al-Ali et al.
11,678,829 B2 6/2023 Al-Ali et al.
11,679,579 B2 6/2023 Al-Ali
11,684,296 B2 6/2023 Vo et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.
D998,625 S 9/2023 Indorf et al.
D998,630 S 9/2023 Indorf et al.
D998,631 S 9/2023 Indorf et al.
D999,244 S 9/2023 Indorf et al.
D999,245 S 9/2023 Indorf et al.
D999,246 S 9/2023 Indorf et al.
11,766,198 B2 9/2023 Pauley et al.
D1,000,975 S 10/2023 Al-Ali et al.
11,803,623 B2 10/2023 Kiani et al.
11,832,940 B2 12/2023 Diab et al.
D1,013,179 S 1/2024 Al-Ali et al.
11,872,156 B2 1/2024 Telfort et al.
11,879,960 B2 1/2024 Ranasinghe et al.
11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
D1,031,729 S 6/2024 Forrest et al.
12,004,869 B2 6/2024 Kiani et al.
12,014,328 B2 6/2024 Wachman et al.
D1,036,293 S 7/2024 Al-Ali et al.
D1,037,462 S 7/2024 Al-Ali et al.
12,029,844 B2 7/2024 Pauley et al.
12,048,534 B2 7/2024 Vo et al.
12,064,217 B2 8/2024 Ahmed et al.
12,066,426 B1 8/2024 Lapotko et al.
D1,041,511 S 9/2024 Indorf et al.
D1,042,596 S 9/2024 DeJong et al.
D1,042,852 S 9/2024 Hwang
12,076,159 B2 9/2024 Belur Nagaraj et al.
12,082,926 B2 9/2024 Sharma et al.
D1,044,828 S 10/2024 Chandran et al.
D1,048,571 S 10/2024 Yu et al.
D1,048,908 S 10/2024 Al-Ali et al.
12,106,752 B2 10/2024 Campbell et al.
12,114,974 B2 10/2024 Al-Ali et al.
12,126,683 B2 10/2024 Koo et al.
12,127,838 B2 10/2024 Olsen et al.
12,128,213 B2 10/2024 Kiani et al.
12,131,661 B2 10/2024 Pauley et al.
D1,050,910 S 11/2024 Al-Ali et al.
12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Al-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin
D1,066,244 S 3/2025 Lim et al.
D1,066,672 S 3/2025 Al-Ali et al.
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0144582 A1 7/2003 Cohen et al.
2003/0156288 A1 8/2003 Barnum et al.
2003/0212312 A1 11/2003 Coffin, IV et al.
2004/0106163 A1 6/2004 Workman, Jr. et al.
2005/0055276 A1 3/2005 Kiani et al.
2005/0234317 A1 10/2005 Kiani
2006/0073719 A1 4/2006 Kiani
2006/0189871 A1 8/2006 Al-Ali et al.
2007/0073116 A1 3/2007 Kiani et al.
2007/0117473 A1 5/2007 Uchida et al.
2007/0180140 A1 8/2007 Welch et al.
2007/0244377 A1 10/2007 Cozad et al.
2008/0064965 A1 3/2008 Jay et al.
2008/0094228 A1 4/2008 Welch et al.
2008/0103375 A1 5/2008 Kiani
2008/0221418 A1 9/2008 Al-Ali et al.
2009/0036759 A1 2/2009 Ault et al.
2009/0093687 A1 4/2009 Telfort et al.
2009/0095926 A1 4/2009 MacNeish, III
2009/0247984 A1 10/2009 Lamego et al.
2009/0275844 A1 11/2009 Al-Ali
2010/0004518 A1 1/2010 Vo et al.
2010/0030040 A1 2/2010 Poeze et al.
2010/0099964 A1 4/2010 O'Reilly et al.
2010/0234718 A1 9/2010 Sampath et al.
2010/0270257 A1 10/2010 Wachman et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0118561 A1 5/2011 Tari et al.
2011/0137297 A1 6/2011 Kiani et al.
2011/0172498 A1 7/2011 Olsen et al.
2011/0213274 A1* 9/2011 Telfort ................. A61B 5/7214 600/586
2012/0123231 A1 5/2012 O'Reilly
2012/0165629 A1 6/2012 Merritt et al.
2012/0209084 A1 8/2012 Olsen et al.
2012/0226117 A1 9/2012 Lamego et al.
2012/0283524 A1 11/2012 Kiani et al.
2013/0023775 A1 1/2013 Lamego et al.
2013/0060147 A1 3/2013 Welch et al.
2013/0096405 A1 4/2013 Garfio
2013/0296672 A1 11/2013 O'Neil et al.
2013/0345921 A1 12/2013 Al-Ali et al.
2014/0081175 A1* 3/2014 Telfort ..................... A61B 7/04 600/586
2014/0166076 A1 6/2014 Kiani et al.
2014/0180160 A1 6/2014 Brown et al.
2014/0187973 A1 7/2014 Brown et al.
2014/0275871 A1 9/2014 Lamego et al.
2014/0275872 A1 9/2014 Merritt et al.
2014/0316217 A1 10/2014 Purdon et al.
2014/0316218 A1 10/2014 Purdon et al.
2014/0323897 A1 10/2014 Brown et al.
2014/0323898 A1 10/2014 Purdon et al.
2015/0005600 A1 1/2015 Blank et al.
2015/0011907 A1 1/2015 Purdon et al.
2015/0073241 A1 3/2015 Lamego
2015/0080754 A1 3/2015 Purdon et al.
2015/0099950 A1 4/2015 Al-Ali et al.
2017/0024748 A1 1/2017 Haider
2017/0055896 A1* 3/2017 Al-Ali ...................... A61B 5/01
2017/0173632 A1* 6/2017 Al-Ali ...................... C09J 7/405
2017/0251974 A1 9/2017 Shreim et al.
2018/0008146 A1* 1/2018 Al-Ali ................ A61B 5/14552
2018/0242876 A1* 8/2018 Hughes .................. G16H 40/67
2018/0242926 A1 8/2018 Muhsin et al.

(56) References Cited

U.S. PATENT DOCUMENTS

2018/0247712 A1 8/2018 Muhsin et al.
2019/0038170 A1* 2/2019 Baxi .................... A61B 5/0205
2020/0111552 A1 4/2020 Ahmed
2020/0113496 A1* 4/2020 Scruggs ............. A61B 5/02444
2020/0113520 A1 4/2020 Abdul-Hafiz et al.
2020/0138368 A1 5/2020 Kiani et al.
2020/0163597 A1 5/2020 Dalvi et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1* 10/2020 Al-Ali ................ A61B 5/02438
2020/0329983 A1 10/2020 Al-Ali et al.
2020/0329993 A1 10/2020 Al-Ali et al.
2021/0022628 A1 1/2021 Telfort et al.
2021/0104173 A1 4/2021 Pauley et al.
2021/0117525 A1 4/2021 Kiani et al.
2021/0161465 A1 6/2021 Barker et al.
2021/0236729 A1 8/2021 Kiani et al.
2021/0259634 A1* 8/2021 Ginestet ............... A61B 5/0002
2021/0275101 A1 9/2021 Vo et al.
2021/0290072 A1 9/2021 Forrest
2021/0290080 A1 9/2021 Ahmed
2021/0290120 A1 9/2021 Al-Ali
2021/0290177 A1 9/2021 Novak, Jr.
2021/0290184 A1 9/2021 Ahmed
2021/0296008 A1* 9/2021 Novak, Jr. ........... A61B 5/0008
2021/0330200 A1 10/2021 Al-Ali et al.
2021/0330228 A1 10/2021 Olsen et al.
2021/0386382 A1 12/2021 Olsen et al.
2021/0402110 A1 12/2021 Pauley et al.
2022/0022748 A1* 1/2022 Al-Ali .................... A61B 5/002
2022/0039707 A1 2/2022 Sharma et al.
2022/0053892 A1 2/2022 Al-Ali et al.
2022/0071562 A1 3/2022 Kiani
2022/0096603 A1 3/2022 Kiani et al.
2022/0151521 A1 5/2022 Krishnamani et al.
2022/0175292 A1* 6/2022 McClung ............. A61B 5/6841
2022/0218244 A1 7/2022 Kiani et al.
2022/0233128 A1 7/2022 Pike et al.
2022/0287574 A1 9/2022 Telfort et al.
2022/0296161 A1 9/2022 Al-Ali et al.
2022/0361819 A1 11/2022 Al-Ali et al.
2022/0379059 A1 12/2022 Yu et al.
2022/0392610 A1 12/2022 Kiani et al.
2023/0028745 A1 1/2023 Al-Ali
2023/0038389 A1 2/2023 Vo
2023/0045000 A1 2/2023 Al-Ali et al.
2023/0045647 A1 2/2023 Vo
2023/0058052 A1 2/2023 Al-Ali
2023/0058342 A1 2/2023 Kiani
2023/0069789 A1 3/2023 Koo et al.
2023/0087671 A1 3/2023 Telfort et al.
2023/0110152 A1 4/2023 Forrest et al.
2023/0111198 A1 4/2023 Yu et al.
2023/0115397 A1 4/2023 Vo et al.
2023/0116371 A1 4/2023 Mills et al.
2023/0135297 A1 5/2023 Kiani et al.
2023/0138098 A1 5/2023 Telfort et al.
2023/0145155 A1 5/2023 Krishnamani et al.
2023/0147750 A1 5/2023 Barker et al.
2023/0210417 A1 7/2023 Al-Ali et al.
2023/0222805 A1 7/2023 Muhsin et al.
2023/0222887 A1 7/2023 Muhsin et al.
2023/0226331 A1 7/2023 Kiani et al.
2023/0284916 A1 9/2023 Telfort
2023/0284943 A1 9/2023 Scruggs et al.
2023/0301562 A1 9/2023 Scruggs et al.
2023/0346993 A1 11/2023 Kiani et al.
2023/0368221 A1 11/2023 Haider
2023/0371893 A1 11/2023 Al-Ali et al.
2023/0389837 A1 12/2023 Krishnamani et al.
2024/0016418 A1 1/2024 Devadoss et al.
2024/0016419 A1 1/2024 Devadoss et al.
2024/0047061 A1 2/2024 Al-Ali et al.
2024/0049310 A1 2/2024 Al-Ali et al.
2024/0049986 A1 2/2024 Al-Ali et al.
2024/0081656 A1 3/2024 DeJong et al.
2024/0122486 A1 4/2024 Kiani
2024/0180456 A1 6/2024 Al-Ali
2024/0188872 A1 6/2024 Al-Ali et al.
2024/0245855 A1 7/2024 Vo et al.
2024/0260894 A1 8/2024 Olsen
2024/0267698 A1 8/2024 Telfort et al.
2024/0277233 A1 8/2024 Al-Ali
2024/0298920 A1 9/2024 Fernkbist et al.
2024/0306985 A1 9/2024 Vo et al.
2024/0324953 A1 10/2024 Telfort
2024/0380246 A1 11/2024 Moran
2024/0380247 A1 11/2024 Moran
2024/0404549 A1 12/2024 Campbell et al.
2025/0000458 A1 1/2025 Abdul-Hafiz et al.
2025/0037836 A1 1/2025 Kiani

* cited by examiner

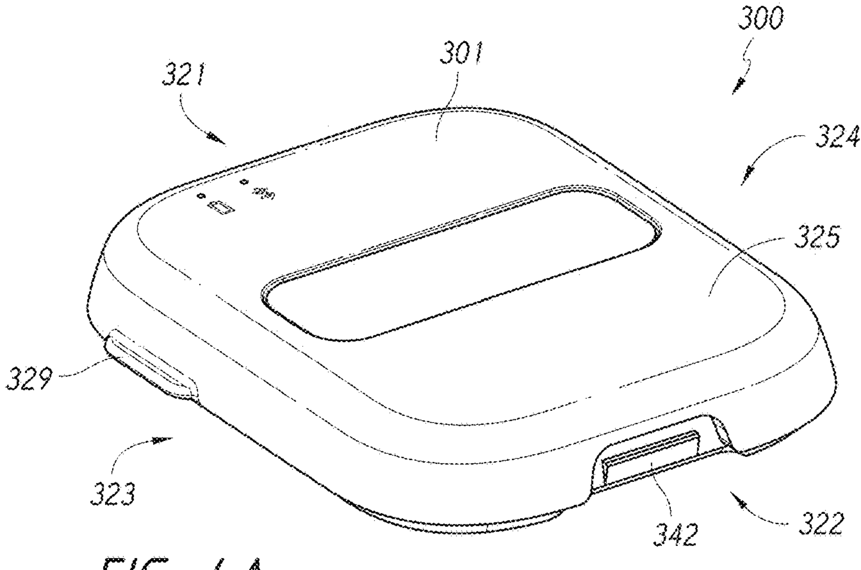
FIG. 4A
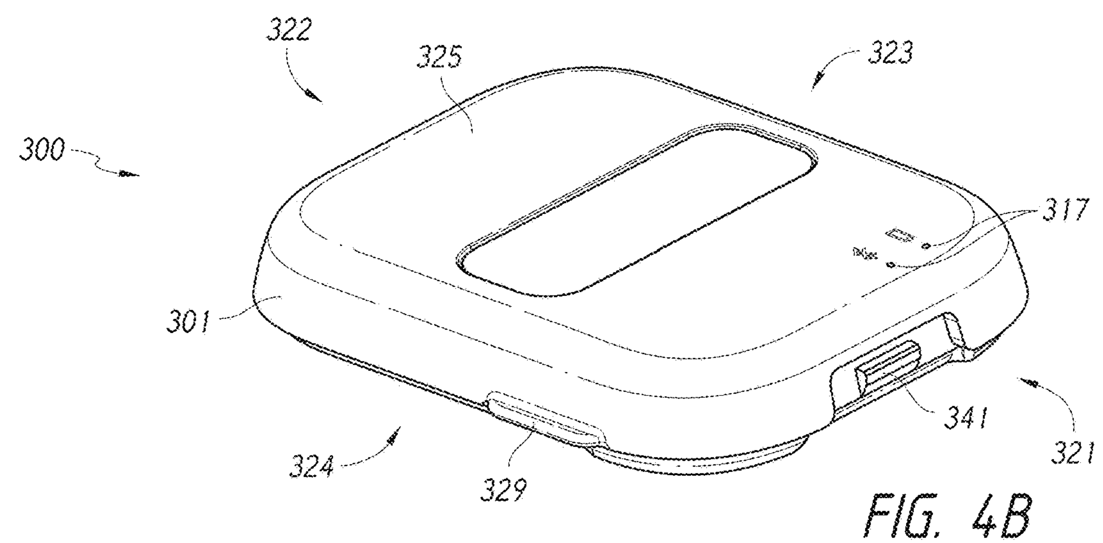
FIG. 4B
300
323
338
337
378
333
335
334
336
322
335
326
374
337
378
345
301
346
341
324
333
329
331
321
FIG. 4C

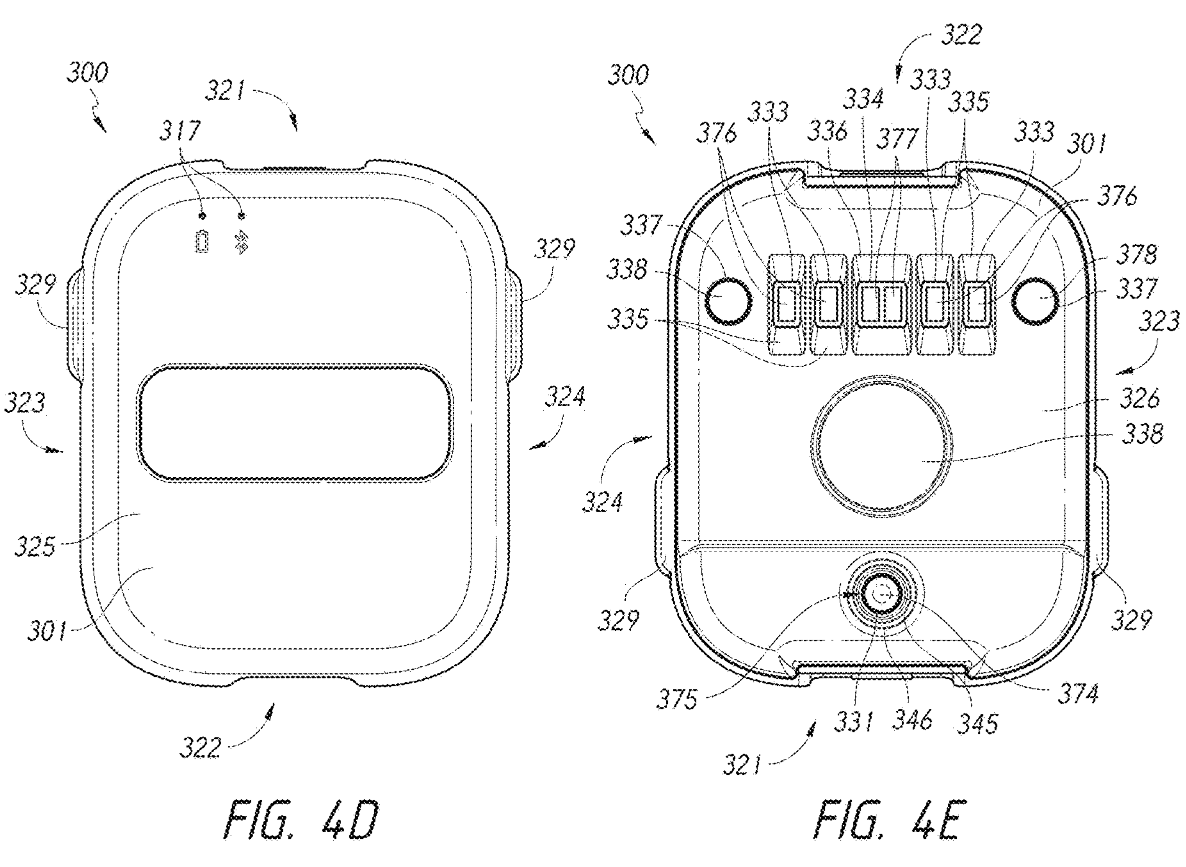
FIG. 4D
FIG. 4E
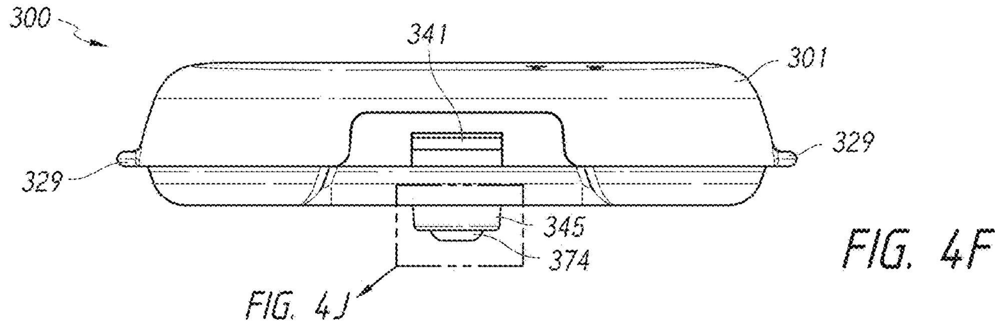
FIG. 4F
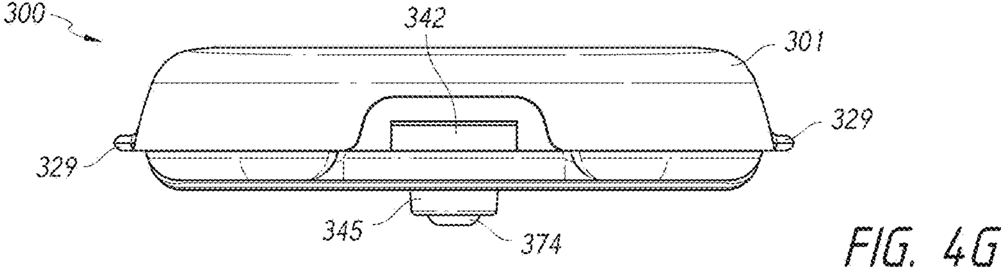
FIG. 4G

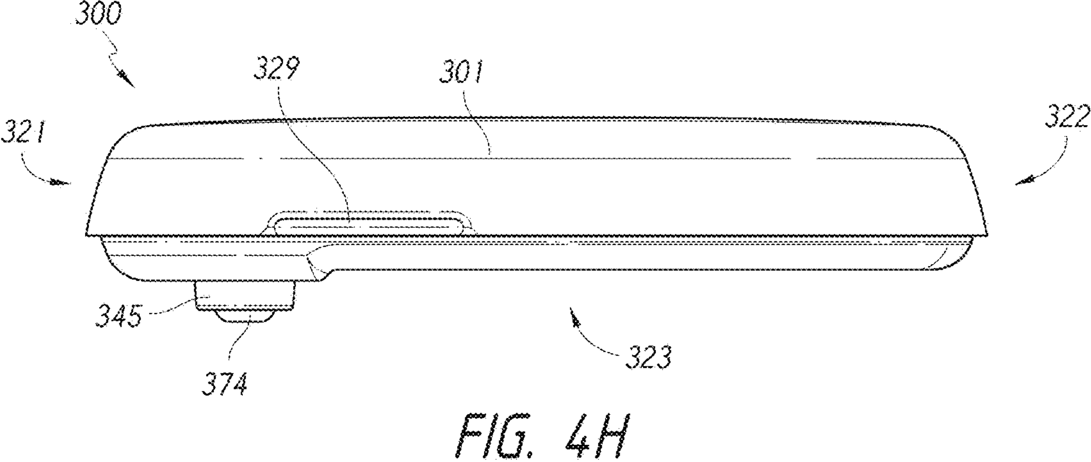
FIG. 4H
300
301
329
322
321
324
345
374
FIG. 4I
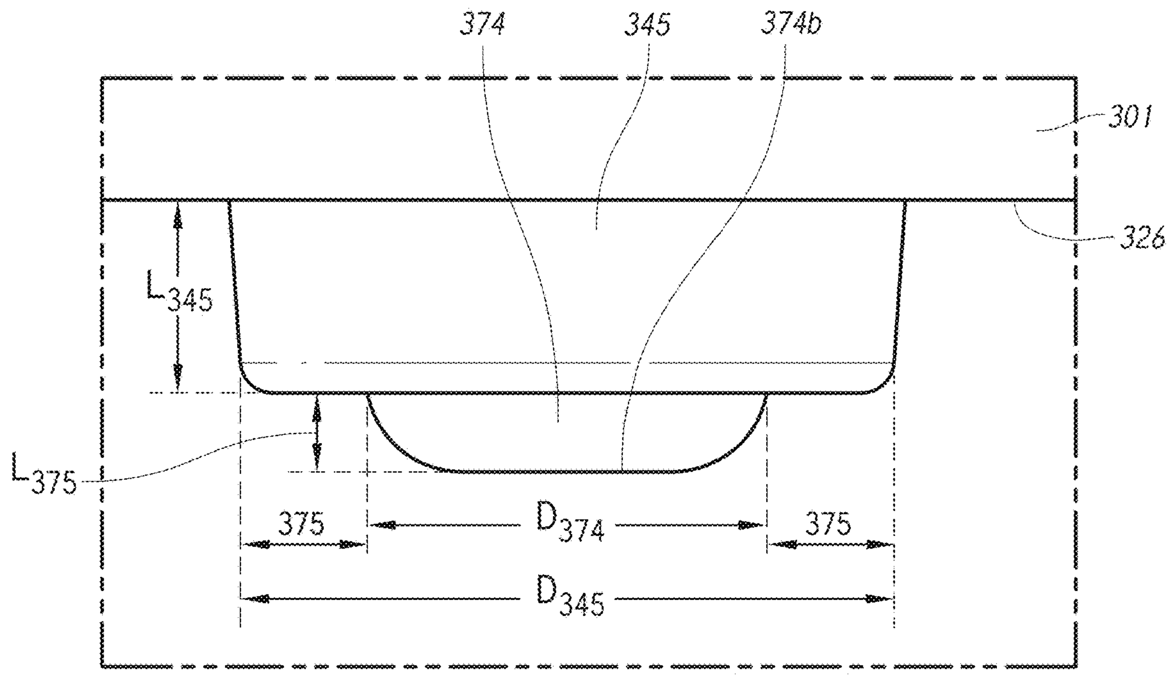
FIG. 4J 301a
327
342a
349
352
381
372
381
378
391
351
350
376
377
300
374
374b
376
381
395
371
381
378
335
337
301b
333
334
346
336
342b
345
333
331
337
326
338
335

400
420
422
402
401
406
410

420
400
422
402

406
412
401
400
420
402
408
410
442
401

WEARABLE MONITORING DEVICE

INCORPORATION BY REFERENCE TO ANY PRIORITY APPLICATIONS

This application claims priority to U.S. Provisional Application No. 63/486,456, filed Feb. 22, 2023, titled "Electrocardiogram Device". The above-listed application and any and all applications for which a foreign or domestic priority claim is identified in the Application Data Sheet as filed with the present application are hereby incorporated by reference under 37 CFR 1.57.

TECHNICAL FIELD

The present disclosure generally relates to systems, methods, and devices for monitoring a subject's physiological information.

BACKGROUND

Electrocardiogram (ECG) is a widely accepted noninvasive procedure that detects the electronic impulses of a subject's heart. It is often used to detect problems and/or abnormal conditions that may be related to the subject's heart. Temperature is also a widely accepted indicator of subject's health. Temperatures that are too low or too high can negatively impact a subject's metabolic rate, organ function, and/or can cause tissue damage. By collecting and monitoring ECG and temperature data of a subject, care providers can detect and/or prevent harmful conditions such as infections, cardiac arrest, stroke, and other types of conditions.

SUMMARY

This disclosure describes, among other things, implementations of wearable devices, methods, and/or systems for monitoring one or more physiological parameters and/or other parameters of a subject. Such physiological parameters and/or other parameters can include cardiac activity and/or function, body temperature, orientation, movement and/or position of a subject, among others. Advantageously, the wearable devices described herein can monitor such physiological parameters of a subject wirelessly, freeing the subject from being tethered by cabling. The wearable devices described herein can be configured to be secured to the subject (for example, secured to the subject's body).

Disclosed herein is a wearable device comprising a dock and a hub. The dock can comprise: one or more substrates configured to be secured to skin of a subject; a frame coupled to the one or more substrates, the frame comprising a plurality of prongs; and a dock circuit layer comprising a plurality of conductive strips positioned along the plurality of prongs of the frame. The wearable device can further comprise: a plurality of electrodes for monitoring cardiac activity of the subject; and a plurality of cables configured to facilitate electrical communication between the plurality of electrodes and the dock circuit layer. The hub can be configured to be removably secured to the dock and can comprise: a housing comprising an interior and a plurality of openings; a hub circuit layer arranged within the interior of the housing; and one or more hardware processors coupled to the hub circuit layer. In some implementations, when the hub and dock are secured to one another, the plurality of prongs of the frame extend towards the plurality of openings of the housing of the hub and cause the plurality of conductive strips to contact portions of the hub circuit layer to facilitate electrical communication between the plurality of electrodes and the hub circuit layer.

In some implementations, the hub and dock are secured to one another, the plurality of prongs of the frame extend at least partially through the plurality of openings of the housing of the hub and cause the plurality of conductive strips to contact said portions of the hub circuit layer. In some implementations: each of the plurality of prongs comprises a first end connected to a portion of the frame, a second end opposite said first end, and a curved portion that is closer to said second end than to said first end; and when the hub and dock are secured to one another, said curved portions of the plurality of prongs extend at least partially through the plurality of openings of the housing of the hub and cause the plurality of conductive strips to contact portions of the hub circuit layer.

In some implementations: each of the plurality of prongs comprises a first end connected to a portion of the frame, a second end opposite said first end, a convex portion, and a concave portion; said convex portion is closer to said first end than said concave portion; said concave portion is closer to said second end than said convex portion; and when the hub and dock are secured to one another, said concave portions of the plurality of prongs extend at least partially through the plurality of openings of the housing of the hub and cause the plurality of conductive strips to contact portions of the hub circuit layer. In some implementations, said concave portion: comprises a smaller amount of a length of each of said plurality of prongs; is shorter than said convex portion; and/or has a smaller radius of curvature than said convex portion. In some implementations, each of the plurality of prongs comprises a bump on said concave portion, said bumps of the plurality of prongs configured to facilitate contact between the plurality of conductive strips and the portions of the hub circuit layer.

In some implementations, the hub is configured to removably secure to the frame of the dock, wherein the frame includes at least one mechanical connector configured to secure to at least one mechanical connector of the hub. In some implementations, each of the plurality of prongs comprises a bump, said bumps of the plurality of prongs configured to facilitate contact between the plurality of conductive strips and the portions of the hub circuit layer.

In some implementations, said plurality of electrodes are external electrodes configured to be secured to the subject's skin away from the dock, and wherein the wearable device further comprises at least one internal electrode operably positioned by the frame of the dock. In some implementations, the wearable device comprises two internal electrodes spaced from one another and operably positioned by the frame of the dock. In some implementations, the one or more substrates comprises two substrates separated by a channel, wherein each of the two substrates are associated with a different one of the two internal electrodes, and wherein said channel provides electrical isolation between the two internal electrodes. In some implementations, each of the two substrates are configured to be positioned between their respective internal electrode and the subject's skin.

In some implementations, the one or more substrates are electrically and/or thermally conductive. In some implementations, the housing further comprises a plurality of inwardly tapered recesses, each of the plurality of inwardly tapered recesses surrounding a different one of the plurality of openings. In some implementations, the hub further comprises one or more electrical contacts coupled to the hub circuit layer and configured to allow a battery of the hub to receive power from a charging device, and wherein the housing comprises one or more charger contact openings configured to provide access to said one or more electrical contacts. In some implementations, the hub further comprises a temperature sensor.

In some implementations: said plurality of openings of the housing of the hub are prong openings of the housing; said housing further comprises a top portion, a bottom portion, and a probe opening extending through said bottom portion, said bottom portion positioned closer to the subject's skin when the hub and dock are secured to one another and the dock is secured to the subject's skin; said hub circuit layer is a circuit board, said circuit board comprising a first surface, a second surface, and at least one hole extending through the circuit board between the first and second surfaces. In some of implementations, said hub further comprises: a temperature sensor mounted to the first surface of the circuit board adjacent said at least one hole; a thermally conductive probe extending through said probe opening of the housing, the thermally conductive probe comprising a first end and a second end opposite the first end, the first end positioned adjacent the second surface of the circuit board and said at least one hole; In some implementations, when the hub and the dock are secured to one another: the second end of the thermally conductive probe contacts at least one of said one or more substrates of the dock; and the thermally conductive probe is configured to receive thermal energy emanating from the subject's skin through the one or more substrates and transmit said thermal energy towards said temperature sensor via the at least one hole of the circuit board when the dock is secured to the subject's skin.

In some implementations, the hub further comprises a wall extending outward from the bottom portion of the housing and extending around at least a portion of the thermally conductive probe. In some implementations, the wall surrounds an entire cross-section of the thermally conductive probe. In some implementations, the wall surrounds an entire perimeter of the thermally conductive probe. In some implementations, the wall encircles the thermally conductive probe. In some implementations, the thermally conductive probe extends beyond the wall. In some implementations, less than about 30% of a length of the thermally conductive probe extends beyond the wall. In some implementations, the thermally conductive probe extends beyond the wall an amount that is less than about 1.5 mm. In some implementations, the thermally conductive probe extends beyond the wall an amount that is between about 0.2 mm and about 1.5 mm. In some implementations, the wall is cylindrical and the thermally conductive probe is cylindrical. In some implementations, a gap between the thermally conductive probe and the wall is between about 0.2 mm and about 1.5 mm.

Disclosed herein is a wearable device comprising a dock and a hub. The dock can comprise one or more substrates configured to be secured to skin of a subject. The hub can be configured to be removably secured to the dock and can comprise: a housing comprising an interior, a top portion, a bottom portion, and an opening extending through said bottom portion, said bottom portion positioned closer to the subject's skin when the hub and dock are secured to one another and the dock is secured to the subject's skin; a circuit board arranged within the interior of the housing, the circuit board comprising a first surface, a second surface, and at least one hole extending through the circuit board between the first and second surfaces; one or more hardware processors coupled to the circuit board and arranged within the interior of housing; a temperature sensor mounted to the first surface of the circuit board adjacent said at least one hole; a thermally conductive probe extending through said opening of the housing, the thermally conductive probe comprising a first end and a second end opposite the first end, the first end positioned adjacent the second surface of the circuit board and said at least one hole; and a wall extending outward from the bottom portion of the housing and extending around at least a portion of the thermally conductive probe. In some implementations, when the hub and the dock are secured to one another and the dock is secured to the subject's skin: the second end of the thermally conductive probe contacts at least one of said one or more substrates of the dock; and the thermally conductive probe is configured to receive thermal energy emanating from the subject's skin through the one or more substrates and transmit said thermal energy towards said temperature sensor via the at least one hole of the circuit board.

In some implementations, the hub further comprises a battery coupled to the circuit board and arranged within the interior of the housing. In some implementations, the wall surrounds an entire cross-section of the thermally conductive probe. In some implementations, the wall surrounds an entire perimeter of the thermally conductive probe. In some implementations, the wall encircles the thermally conductive probe. In some implementations, the thermally conductive probe extends beyond the wall. In some implementations, less than about 30% of a length of the thermally conductive probe extends beyond the wall. In some implementations, the thermally conductive probe extends beyond the wall an amount that is less than about 1.5 mm. In some implementations, the thermally conductive probe extends beyond the wall an amount that is between about 0.2 mm and about 1.5 mm. In some implementations, the wall is cylindrical and the thermally conductive probe is cylindrical. In some implementations, a gap between the thermally conductive probe and the wall is between about 0.2 mm and about 1.5 mm.

In some implementations, said temperature sensor is a first temperature sensor of the wearable device, and the wearable device further comprises a second temperature sensor mounted to the first surface of the circuit board spaced from the first temperature sensor. In some implementations, the one or more processors are configured to receive one or more signals from the first and temperature sensors and determine a body temperature of the subject based on said received signals.

In some implementations, the wearable device further comprises: a plurality of electrodes for monitoring cardiac activity of the subject; and a plurality of cables configured to facilitate electrical communication between the plurality of electrodes and the circuit board of the hub via an electrical connection between the dock and the hub when the hub and the dock are secured to one another. In some implementations, the dock further comprises a circuit layer, and wherein said plurality of cables are configured to facilitate electrical communication between the plurality of electrodes and the circuit layer. In some implementations, said plurality of electrodes are external electrodes configured to be secured to the subject's skin away from the dock, and wherein the wearable device further comprises at least one internal electrode operably positioned by the dock. In some implementations, the wearable device comprises two internal electrodes spaced from one another and operably positioned by the dock.

Disclosed herein is a wearable device configured to measure physiological parameters of a subject. The wearable device can include a dock having a plurality of prongs, a dock circuit layer having a plurality of conductive strips positioned along the plurality of prongs, and a plurality of electrodes in electrical communication with the dock circuit layer. The wearable device can also include a hub configured to be removably secured to the dock, the hub having a housing with a plurality of openings, and a hub circuit layer arranged within the interior of the housing. When the hub and dock are secured to one another, the plurality of prongs of the frame can extend towards the plurality of openings of the housing of the hub and cause the plurality of conductive strips to contact portions of the hub circuit layer to facilitate electrical communication between the plurality of electrodes and the hub circuit layer.

Disclosed herein is a system comprising any of the implementations of wearable devices described above or elsewhere herein and also a charging device. In some implementations, the charging device comprises a plurality of charging cavities, each of the plurality of charging cavities configured to receive at least a portion of the hub and charge a battery of the hub.

For purposes of summarizing the disclosure, certain aspects, advantages, and novel features are discussed herein. It is to be understood that not necessarily all such aspects, advantages, or features will be embodied in any particular implementation of the disclosure, and an artisan would recognize from the disclosure herein a myriad of combinations of such aspects, advantages, or features.

BRIEF DESCRIPTION OF THE DRAWINGS

Certain features of this disclosure are described below with reference to the drawings. The illustrated implementations are intended to illustrate, but not to limit, the implementations. Various features of the different disclosed implementations can be combined to form further implementations, which are part of this disclosure.

FIGS. 4A-4B illustrate top perspective views of the hub of FIGS. 1C-1D in accordance with aspects of this disclosure.

FIG. 4C illustrates a bottom perspective view of the hub of FIGS. 1C-1D in accordance with aspects of this disclosure.

FIGS. 4D-4I illustrate a top view, a bottom view, a first end view, a second end view, a first side view, and a second side view, respectively, of the hub of FIGS. 1C-1D in accordance with aspects of this disclosure.

FIG. 4J illustrates an enlarged view of a portion of the hub as identified in FIG. 4F in accordance with aspects of this disclosure.

DETAILED DESCRIPTION

Figure 1A:
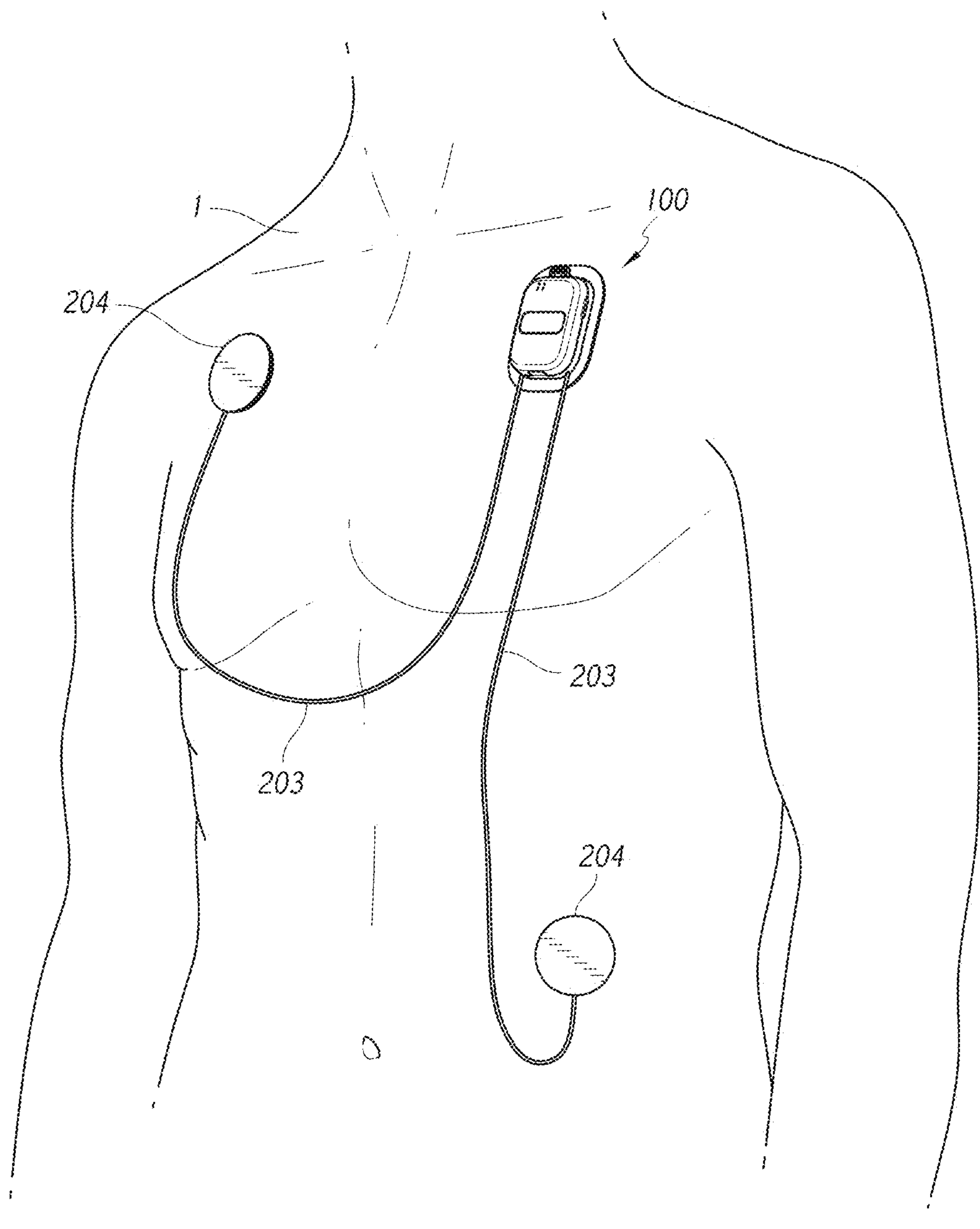
FIG. 1A illustrates a perspective view of a wearable device secured to a subject in accordance with aspects of this disclosure.

Various features and advantages of this disclosure will now be described with reference to the accompanying figures. The following description is merely illustrative in nature and is in no way intended to limit the disclosure, its application, or uses. This disclosure extends beyond the specifically disclosed implementations and/or uses and obvious modifications and equivalents thereof. Thus, it is intended that the scope of this disclosure should not be limited by any particular implementations described below. The features of the illustrated implementations can be modified, combined, removed, and/or substituted as will be apparent to those of ordinary skill in the art upon consideration of the principles disclosed herein.

Disclosed herein are wearable devices that can be used to measure, monitor, process, determine and/or transmit (for example, wirelessly) one or more physiological parameters and/or other parameters of a subject (which can also be referred to herein as a "user", "patient", or "wearer"). The one or more physiological parameters and/or other parameters of the subject can include cardiac activity and/or function, body temperature (for example, core body temperature), orientation, position, and/or movement. Orientation, position, and/or movement of a subject can include orientation of the subject relative to a surface such as a bed, movement in their environment such as a number of steps taken and/or a type and/or a quantity of exercise, a fall, and/or the like. In some implementations, the wearable devices disclosed herein can be configured to measure, monitor, process, determine and/or transmit other physiological parameters of a subject such as lung activity and/or function, body sounds, and/or the like. The wearable devices disclosed herein can also include one or more user inputs (which can also be referred to herein as "user input devices") that allow a subject to interact with the wearable device. Various implementations of the wearable devices disclosed herein can be configured to removably attach to a subject, for example, via an adhesive substrate. Also disclosed herein is a charger configured to charge a wearable device and/or a component thereof as described herein.

Some implementations of the disclosed wearable devices (or portions of such devices) can be disposable, which can reduce the risk of cross-contamination between multiple subjects. Some implementations of the disclosed wearable devices (or portions of such devices) can be waterproof, thereby providing minimal disruption to ordinary activities of the subject (for example, showering). Various implementations of the disclosed wearable devices include two separable components (which may also be referred to as "separate portions"). In such implementations, a first one of the components can be configured to secure to a portion of a subject (for example, skin of the subject) and a second one of the components can be configured to secure (for example, removably secure) to the first component. In some implementations, the second component is spaced away from the subject's skin and/or does not contact the subject's skin when secured to the first component in use. In some implementations, the first and second components are configured such that separation thereof is inhibited or prevented when the first component is secured to the subject but is allowed when the first component is not secured to the subject. Such implementations can be advantageous in scenarios where it is desirable to inhibit or prevent a subject from interfering with operation of the wearable device. In some implementations, the wearable device includes a button configured to transition the wearable device (or a portion thereof such as the second component discussed above) between non-operational and operational modes. In some of such implementations, such button is inaccessible (for example, to the subject wearing the wearable device and/or to another person, such as a care provider) unless the first and second components are separated from one another. Such implementation can advantageously prevent a subject (for example, a child) from intentionally or unintentionally turning the wearable device off when the wearable device is secured to the subject (which can ensure proper compliance in some situations). Such "first component" can be any of the docks and/or dock assemblies disclosed herein and such "second component" can be any of the hubs disclosed herein.

Some implementations of the disclosed wearable devices are configured to monitor an electrocardiogram (ECG) activity of a subject. For example, some implementations of the wearable devices disclosed herein include a plurality of electrodes for monitoring cardiac activity and/or function of a subject. Such electrodes can be configured to output one or more signals responsive to the subject's electrical activity, such as the subject's cardiac electrical activity. Such plurality of electrodes can include one or more external electrodes and/or one or more internal electrodes. Such external electrodes can be configured to be secured to the subject's body. Furthermore, such external electrodes can electrically communicate with other portions of the wearable devices described herein via a cable. Output from such electrodes can be received by one or more hardware processors of the wearable device for determination of an ECG of the subject. Wearable devices described herein can incorporate any of the features described with respect to any of the devices, assemblies, methods, and/or systems described and/or illustrated in U.S. Pat. Pub. No. US2022/0233128, titled "ELECTROCARDIOGRAM DEVICE," which is hereby incorporated by reference in its entirety and for all purposes.

Some implementations of the disclosed wearable devices include a temperature sensor. Some implementations of the disclosed wearable devices include multiple temperature sensors operably positioned in different locations with respect to one another and with respect to the subject's skin when in use. Such configurations can allow temperature to be determined at each of these different locations and compared with one another. In some implementations, thermal paths (which may be referred to as "thermal flow paths" or "heat flow paths") between temperature sensors are defined by air, a thermally insulative element, and/or a thermally conductive element, which can provide additional information where thermal properties (for example, thermal conductivity values) are known. Differences between measurements at various ones of the temperature sensors can be utilized to provide more accurate estimates of body temperature (for example, core body temperature) of the subject. Some implementations include two or more temperature sensors, where one or more of the temperature sensors are at least partially thermally coupled to the subject's skin/body (when the wearable device is in use) and one or more of the temperature sensors are at least partially thermally insulated and/or isolated from the subject's skin/body. Some implementations include an air gap and/or a portion of a circuit layer or circuit board (which can act as a thermal insulator) between one or more of the temperature sensors. Temperature values determined based on each of the temperature sensors can be compared and utilized to approximate core body temperature (which can also be referred to herein as "internal body temperature") value(s) of the subject. In various implementations, thermally conductive probe(s) can be utilized to transmit energy from a substrate of the wearable device (which can adhere to the subject's skin) to and/or toward a substantially aligned temperature sensor. Wearable devices described herein can incorporate any of the features described with respect to any of the devices, assemblies, methods, and/or systems described and/or illustrated in U.S. Pat. Pub. No. US2023/0087671, filed Sep. 20, 2022, titled "WEARABLE DEVICE FOR NONINVASIVE BODY TEMPERATURE MEASUREMENT," which is hereby incorporated by reference in its entirety and for all purposes.

Some implementations of the disclosed wearable devices are configured to monitor a subject's orientation, position, and/or movement. For example, implementations of the disclosed wearable devices can be configured to monitor a subject's orientation relative to a surface (such as a bed), movement in their environment (such as a number of steps taken, a type and/or quantity of exercise, and/or movement that may interfere or affect physiological monitoring of the subject by the wearable device), a fall, and/or the like. Some implementations of wearable devices disclosed herein include a motion sensor, which can include an inertial motion unit and/or one or more accelerometers and/or one or more gyroscopes, and data from such motion sensor can be utilized to determine the subject's orientation, position, and/or movement over time. Wearable devices described herein can incorporate any of the features described with respect to any of the devices, assemblies, methods, and/or systems described and/or illustrated in U.S. Pat. No. 11,406,286, filed Oct. 10, 2019, titled "PATIENT MONITORING DEVICE WITH IMPROVED USER INTERFACE," in U.S. Pat Pub. No. US2023/0045000, filed Oct. 6, 2022, titled "PATIENT MONITORING DEVICE WITH IMPROVED USER INTERFACE," and in U.S. Pat. Pub. No. US2021/0330200, filed Jul. 5, 2021, titled "SYSTEMS AND METHODS FOR PATIENT FALL DETECTION," which are hereby incorporated by reference in their entirety and for all purposes.

FIG. 1A illustrates a perspective view of a wearable device 100 (which can also be referred to as a "physiological monitoring device") secured to a subject 1. Wearable device 100 can be configured to be secured (for example, removably secured) to skin of the subject 1. For example, and as shown in FIG. 1A, the wearable device 100 can be configured to be secured to a subject's torso and/or portions thereof, such as a chest and/or stomach of the subject 1. The wearable device 100 can be secured to, affixed to or otherwise placed on various portions of the subject's body in addition to or as an alternative to placement on the subject's torso. Wearable device 100 can secure to skin of a subject and noninvasively measure, monitor, process, determine, and/or transmit (for example, wirelessly) one or more physiological parameters of the subject as described herein. In some implementations, the placement of the wearable device 100 and/or portions thereof with respect to portions of the subject's body facilitates one or more measuring, monitoring, processing, determining, and/or transmitting functions of the wearable device 100. Wearable device 100 can perform such measuring, monitoring, processing, determining, and/or transmitting using one or more sensors and/or components as described herein. Wearable device 100 can wirelessly communicate with separate devices and/or systems (for example, continuously or periodically wirelessly transmit physiological and/or other information of the subject to a separate device and/or system).

The wearable device 100 can be affixed to the subject's skin using any form of medically-appropriate adherent material. For example, one or more portions of wearable device 100 can include an adhesive material (for example, a medical grade adhesive) that can allow the wearable device 100 or portions thereof to secure (for example, removably secure) to the subject's skin. As another example, the wearable device 100 can include a pressure-sensitive adhesive that is coated or applied to a bottom surface of or one or more portions of the wearable device 100 for securing the wearable device 100 or portions thereof to the subject's skin. In another example, the wearable device can be secured to a subject's skin with an adhesive that wraps over the wearable device 100 or one or more portions thereof. One skilled in the art will appreciate that many other materials and techniques can be used to affix the wearable device 100 or portions thereof to the subject without departing from the scope of the present disclosure.

Wearable device 100 can include a first component that can secure (for example, removably secure) wearable device 100 to a subject and a second component that can secure to such first component. In some implementations, such first and second components of wearable device 100 can be removable from each other. In some implementations, such first component includes one or more substrates configured to adhere (for example, removably adhere) to skin. In some implementations, such first component includes one or more electronic components and/or sensors of the wearable device 100, and such second component includes one or more electronic components and/or sensors of the wearable device 100. In such implementations, the first and second components can be configured to electrically communicate with one another when secured together. In some implementations, the intended service lives of the first and second components are different. For example, the intended service life of the first component can be less than the intended service life of the second component, such as where the first component includes one or more substrates that secure to the subject's skin. In such implementations, the first component can be disposed of and replaced and the second component can be secured with a new first component. This is advantageous where the substrates lose integrity and/or become degraded after an amount of time. An implementation of such first component is dock 201 and/or dock assembly 200, each of which are discussed further below. An implementation of such second component is hub 300 discussed further below.

Figure 1B:
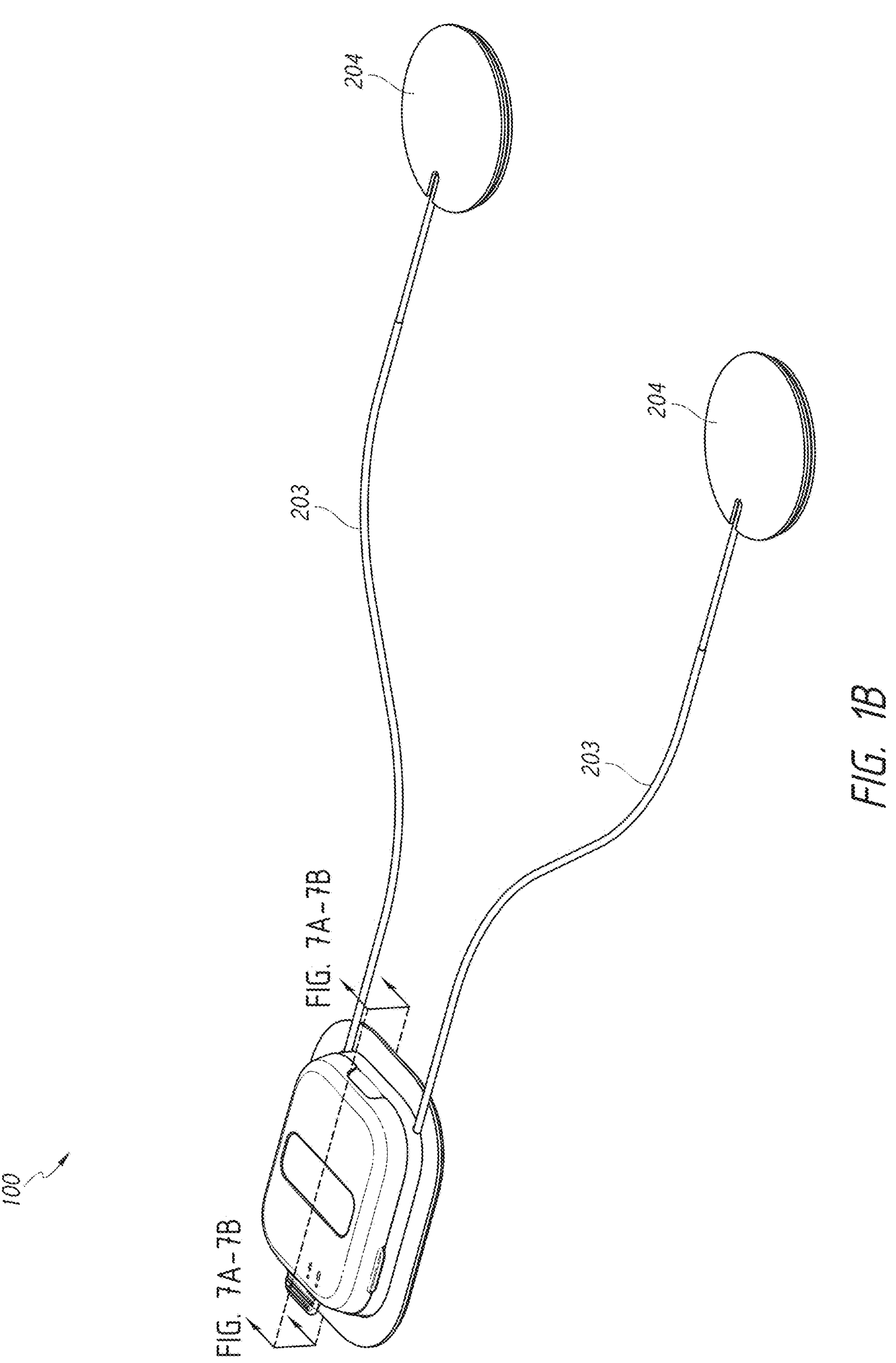
FIG. 1B illustrates a top perspective view of the wearable device of FIG. 1A in accordance with aspects of this disclosure.
Figure 1C:
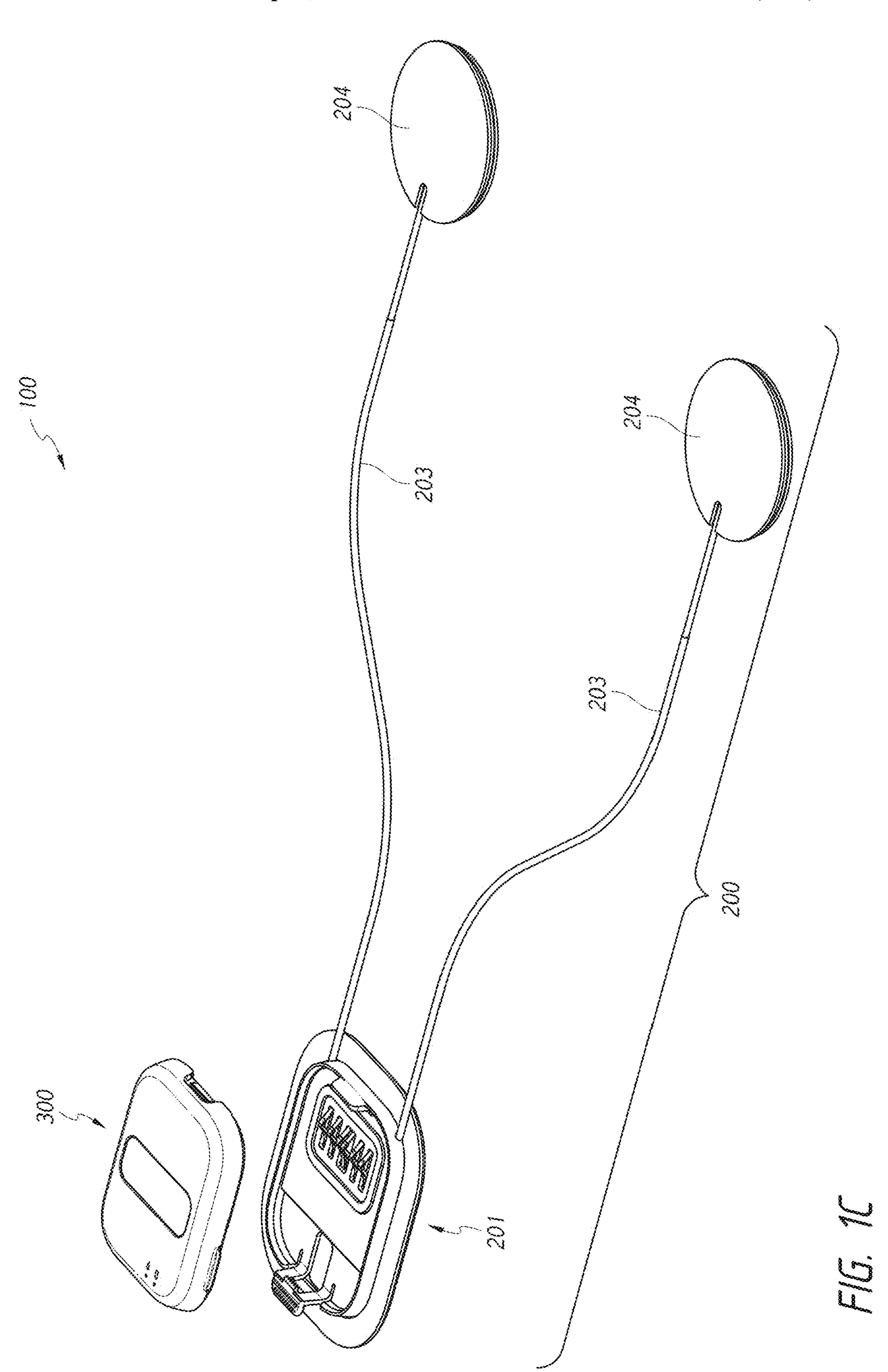
FIG. 1C illustrates a top perspective view of the wearable device of FIG. 1A with a hub detached from a dock assembly in accordance with aspects of this disclosure.
Figure 1D:
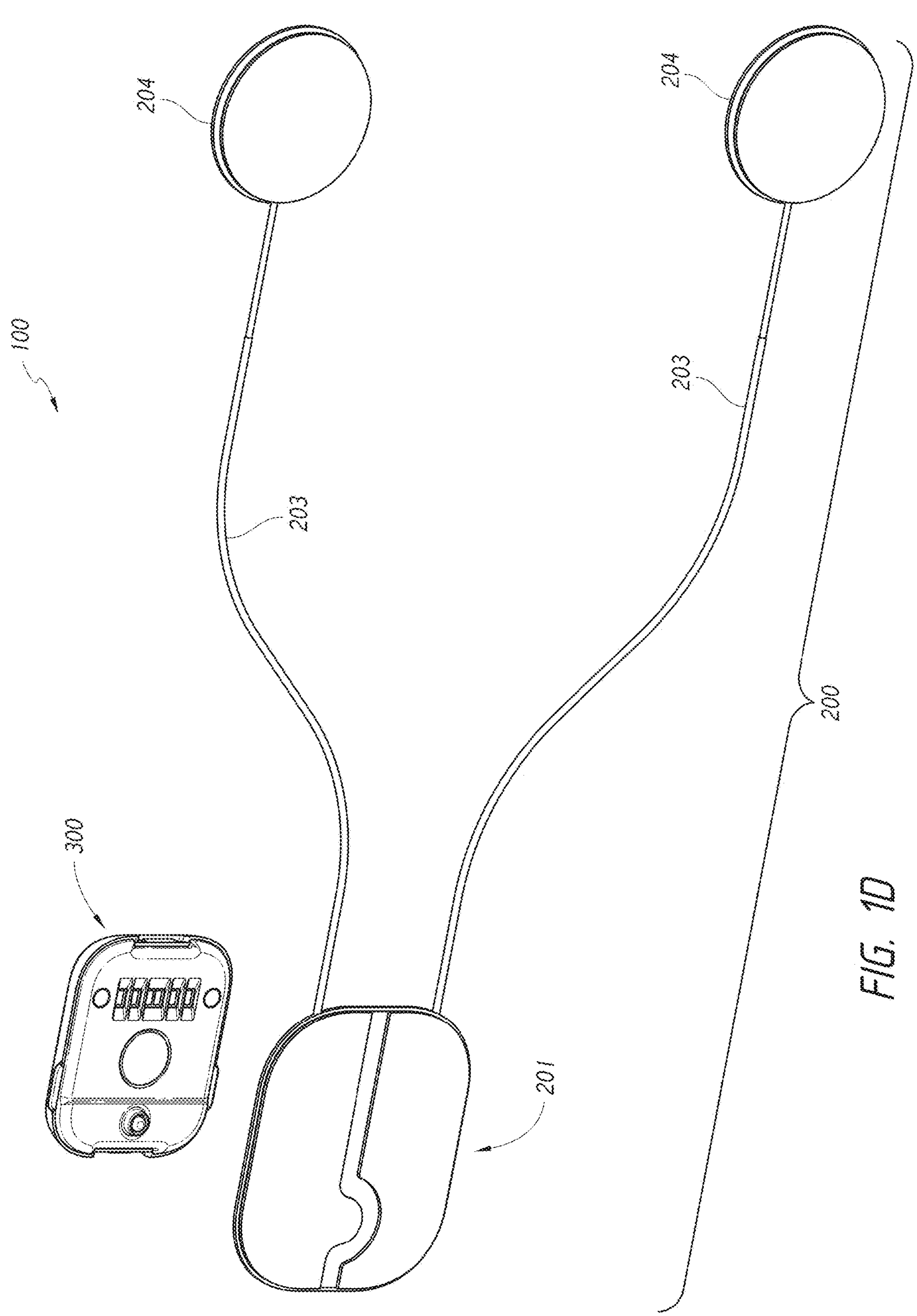
FIG. 1D illustrates a bottom perspective view of the wearable device of FIG. 1A with the hub detached from the dock assembly in accordance with aspects of this disclosure.

FIGS. 1B-1D illustrate various perspective views of wearable device 100 of FIG. 1A. As shown, wearable device 100 can include a dock 201 and a hub 300. In some implementations, wearable device 100 includes a dock assembly 200 that includes dock 201 as well as cable(s) 203 and electrode(s) 204 (described further below). As discussed in more detail herein and as shown in FIGS. 1C-1D, hub 300 (which can also be referred to herein as a "sensor hub") can be removably securable to dock 201 and dock assembly 200 (which can also be referred to herein as a "sensor dock assembly"). Dock assembly 200 can include a plurality of electrodes 204 and a plurality of cables 203 configured to facilitate electrical communication between the plurality of electrodes 204 and the dock 201. For this, cables 203 can be mechanically and electrically connected to and extend from dock 201 and be mechanically and electrically connected to electrodes 204. As shown, each electrode 204 can be connected to dock 201 by a dedicated cable 203. Furthermore, each electrode 204, via a cable 203, can be secured to the subject away from dock 201 (such as shown in FIG. 1A) and in a position for determining cardiac activity and/or function. Dock assembly 200 can additionally include one or more electrodes operably positioned by dock 201 (for example, electrodes(s) 202 discussed with reference to at least FIG. 1E). Dock assembly 200 can also include one or more substrates (as described herein) configured to secure wearable device 100 (or portions thereof) to skin of subject 1. Dock assembly 200 can be formed as a unitary component. In some implementations, wearable device 100 includes dock 201, cables 203, electrodes 204, one or more electrodes (for example, electrodes 202) positioned by dock 201, one or more substrates, and hub 300. Hub 300 can be configured to be removably secured to dock 201. As described in more detail herein, dock 201 and dock assembly 200 can secure to skin of a subject 1 and operably position sensors of wearable device 100 relative to subject 1.

While wearable device 100 is shown in FIGS. 1A-ID as having two electrodes 204 and two cables 203, this is not intended to be limiting. Wearable device 100 can include one, two, three, four, five, six or seven or more cables 203 and/or a corresponding number of electrodes 204.

Figure 1E:
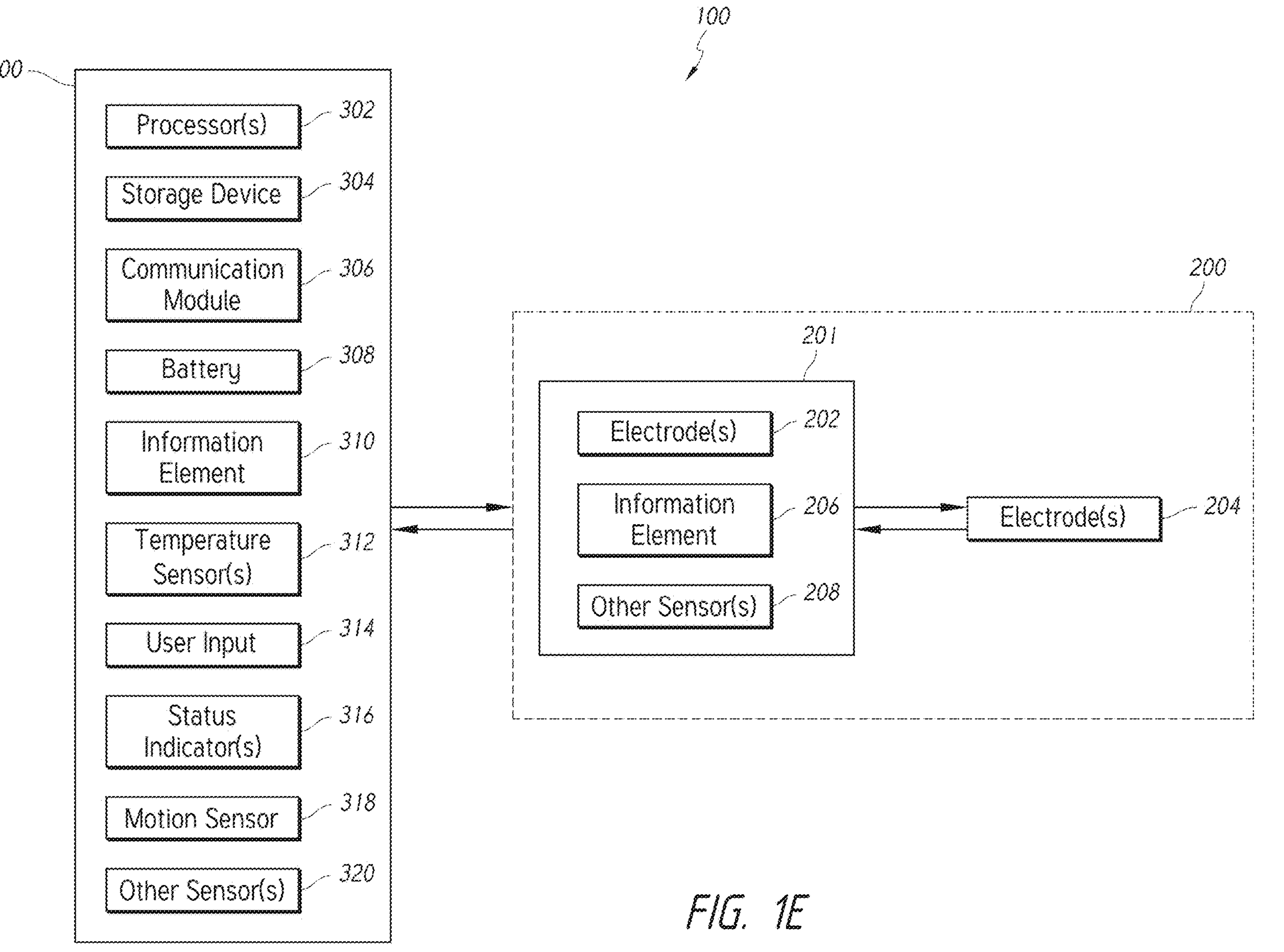
FIG. 1E illustrates a schematic diagram of the wearable device of FIG. 1A in accordance with aspects of this disclosure.

FIG. 1E illustrates an example schematic diagram of wearable device 100. Wearable device 100 can include one or more processors 302 (for example, hardware processor(s)), a storage device 304, a communication module 306, a battery 308, an information element 310, one or more temperature sensors 312, a user input 314, one or more status indicators 316, a motion sensor 318, one or more other sensors 320, one or more electrodes 202, an information element 206, one or more other sensors 208, and/or one or more electrodes 204. In implementations in which wearable device 100 includes a hub 300 and a dock assembly 200, hub 300 can include the one or more processors 302 (for example, hardware processor(s)), storage device 304, communication module 306, battery 308, information element 310, one or more temperature sensors 312, user input 314, one or more status indicators 316, motion sensor 318, and/or one or more other sensors 320. Further to such implementations, the dock assembly 200 can include the one or more electrodes 202, information element 206, one or more other sensors 208, and/or one or more electrodes 204. In some implementations, dock 201 of wearable device 100 includes the one or more electrodes 202, information element 206, one or more other sensors 208, and/or one or more electrodes 204.

Processor(s) 302 can be configured, among other things, to process data, execute instructions to perform one or more functions, and/or control the operation of wearable device 100 and/or components thereof. For example, processor(s) 302 can process physiological data and/or other data (for example, relating to cardiac activity and/or function, temperature, motion, position, orientation, and/or location data) obtained from wearable device 100 and can execute instructions to perform functions related to storing and/or transmitting such physiological data and/or other data. For example, processor(s) 302 can process received data.

Storage device 304 can include one or more memory devices that store data and/or computer-executable instructions, including without limitation, dynamic and/or static random access memory (RAM), programmable read-only memory (PROM), erasable programmable read-only memory (EPROM), electrically erasable programmable read-only memory (EEPROM), and the like. Such stored data can be processed and/or unprocessed physiological data and/or other data obtained from wearable device 100, for example.

Communication module 306 can facilitate communication (via wired and/or wireless connection) between wearable device 100 (and/or components thereof) and separate devices, such as external monitoring and/or mobile devices. For example, communication module 306 can be configured to allow wearable device 100 to wirelessly communicate with other devices, systems, and/or networks over any of a variety of communication protocols. Communication module 306 can be configured to use any of a variety of wireless communication protocols, such as Wi-Fi (802.11x), Bluetooth®, ZigBee®, Z-Wave®, cellular telephony, infrared, near-field communications (NFC), RFID, satellite transmission, proprietary protocols, combinations of the same, and the like. Communication module 306 can allow data and/or instructions to be transmitted and/or received to and/or from wearable device 100 and separate computing devices. Communication module 306 can be configured to transmit (for example, wirelessly) processed and/or unprocessed physiological or other information to separate computing devices, which can include, among others, a mobile device (for example, an iOS or Android enabled smartphone, tablet, laptop), a desktop computer, a server or other computing or processing device for display and/or further processing, among other things. Such separate computing devices can be configured to store and/or further process the received physiological and/or other information, to display information indicative of or derived from the received information, and/or to transmit information—including displays, alarms, alerts, and notifications—to various other types of computing devices and/or systems that may be associated with a hospital, a care provider (for example, a primary care provider), and/or a designee (for example, an employer, a school, friends, family) that have permission to access the subject's data. As another example, communication module 306 of wearable device 100 can be configured to wirelessly transmit processed and/or unprocessed obtained physiological information and/or other information (for example, relating to cardiac activity and/or function, temperature, motion, position, orientation, and/or location data) to a mobile phone which can include one or more hardware processors configured to execute an application that generates a graphical user interface displaying information representative of the processed or unprocessed physiological and/or other information obtained from wearable device 100. In some implementations, communication module 306 can transmit data to and/or receive data from a subject's electronic medical record. In some implementations, wearable device 100 can be used for telehealth. For example, subject 1 can be sent home with wearable device 100, which can transmit data to the cloud for a care provider to review. Communication module 306 can be embodied in one or more components that are in communication with each other. Communication module 306 can comprise a wireless transceiver, an antenna, and/or a near field communication (NFC) component, for example, antenna 362 and/or NFC transponder 361 discussed further below.

Battery 308 can provide power for hardware components of wearable device 100 described herein. Battery 308 can be rechargeable. For example, battery 308 can be a lithium, a lithium polymer, a lithium-ion, a lithium-ion polymer, a lead-acid, a nickel-cadmium, or a nickel-metal hydride battery. In some implementations, battery 308 can be non-rechargeable. In such implementations, a battery life can be a week or more, two weeks or more, four weeks or more, two months or more, or more or less than these durations. In some implementations, wearable device 100 can include a removable battery isolator configured to electrically isolate battery 308 from other electronic components of wearable device 100 until a subject or care provider desires to use wearable device 100. Additionally or alternatively, wearable device 100 can be configured to obtain power from a power source that is external to wearable device 100. For example, wearable device 100 can include or can be configured to connect to a cable which can itself connect to an external power source to provide power to wearable device 100. In implementations wherein battery 308 is rechargeable, wearable device 100 or a portion thereof, such as hub 300 of wearable device 100, can be configured to be charged by a charger. For example, hub 300 with battery 308 can be configured to be charged by charger 400 described herein. In implementations where wearable device 100 is configured to connect to a power cable, wearable device 100 (for example, the hub 300) can include a port for receiving such a power cable. Such a port can, for example, be positioned at a side, corner, or end of the wearable device 100 (for example, of a hub 300 of the wearable device 100 as described herein), and operably connect such an external power source to battery 308 and/or associated electronic components of wearable device 100. In some implementations, wearable device 100 is configured for induction charging and/or wireless charging.

Information element 310 can be a memory storage element that stores, in non-volatile memory, information used to help maintain a standard of quality associated with the wearable device 100. Illustratively, information element 310 can store information regarding whether wearable device 100 has been previously activated and whether wearable device 100 has been previously operational for a prolonged period of time, such as, for example, four hours, one day, two days, five days, ten days, twenty days. The information stored in information element 310 can be used to help detect improper re-use of wearable device 100, for example.

The one or more temperature sensor(s) 312 can continuously or periodically obtain temperature data of a subject. Advantageously, in some implementations, processor(s) 302 can compare temperature data from more than one temperature sensor 312 (for example, temperature sensors 312*a*, 312*b*, and/or 312*c* as described herein) to more accurately determine body temperature (for example, internal body temperature) of the subject. Each of temperature sensor(s) 312 can generate one or more signals responsive to detected thermal energy and such one or more signals can be received by processor(s) 302 for determination of body temperature value(s) of subject 1. Additionally or alternatively, each of temperature sensor(s) 312 can determine temperature values and transmit such temperature values to processor 308 for determination of body temperature value(s). Temperature sensor(s) 312 can be thermistors or integrated circuit (IC) temperature sensors, for example. Wearable device 100 can incorporate temperature sensor(s), associated structure(s), and/or associated methods of subject temperature determination similar or identical those described and/or illustrated in U.S. Pat Pub. No. US2023/0087671 incorporated by reference herein.

User input 314 can allow a subject (or a care provider) to interact with wearable device 100. User input 314 can be utilized to transition wearable device 100 from a non-operational mode to an operational mode (and vice versa) for example, or carry out other actions. With reference to at least FIG. 4L, wearable device 100 (for example, hub 300 of the wearable device 100 as described herein) can include a button 338 configured to actuate switch 371, which can be an implementation of user input 314.

Status indicator(s) 316 can be configured to indicate a status of wearable device 100, such as a charge status or life of battery 308 of wearable device 100, a mode in which wearable device 100 is operating, a status of a wireless connection with an external device, and/or an error condition, among other things. Status indicator(s) can be implemented as one or more emitters configured to emit light, such as illustrated in at least FIG. 5A.

Motion sensor 318 (which can also be referred to herein as an "inertial measurement unit" or an "IMU") can be configured to measure and/or monitor motion, orientation, position and/or location of a subject. Motion sensor 318 can include one or more accelerometers and/or one or more gyroscopes. Motion sensor 318 can generate one or more signals responsive to detected motion, orientation, position and/or location of the subject. One or more of processor(s) 302 may be configured to received motion, orientation, position, and/or location data of a subject from motion sensor 318. Additionally, one or more of processor(s) 302 may determine motion, orientation, position, and/or location of a subject based on data received from motion sensor 318. For example, wearable device 100 can include a motion sensor 318 that can measure static and/or dynamic acceleration forces and/or angular velocity. By measuring static and/or dynamic acceleration forces and/or angular velocity, motion sensor 318 can be used to calculate movement and/or relative position of wearable device 100. Motion sensor 318 can include one or more, and/or a combination of, for example, an AC-response accelerometer (for example, a charge mode piezoelectric accelerometer and/or a voltage mode piezoelectric accelerometer), a DC-response accelerometer (for example, capacitive accelerometer, piezoresistive accelerometer), a microelectromechanical system (MEMS) gyroscope, a hemispherical resonator gyroscope (HRG), vibrating structure gyroscope (VSG), a dynamically tuned gyroscope (DTG), fiber optic gyroscope (FOG), a ring laser gyroscope (RLG), and the like. Motion sensor 318 can measure acceleration forces and/or angular velocity forces in one-dimension, two-dimensions, or three-dimensions. With calculated position and movement data, subjects wearing wearable device 100 and/or others (for example, care providers) may be able to map the positions or movement vectors of wearable device 100. Any number of motions sensors 318 can be used to collect sufficient data to determine position and/or movement of wearable device 100. As such, in some implementations wearable device 100 includes more than one motion sensor 318. Wearable device 100 can be configured to determine and/or keep track of steps and/or distance traveled by a subject based on data from motion sensor 318.

Incorporating at least one motion sensor 318 (for example, one or more of a combination of an accelerometer and/or a gyroscope) in wearable device 100 can provide a number of benefits. For example, a wearable device 100 can be configured such that, when motion is detected (for example, by processor(s) 302) above a threshold value, wearable device 100 stops determining and/or transmitting physiological parameters. As another example, a wearable device 100 can be configured such that, when motion is detected above and/or below a threshold value, electrode(s) 202, electrode(s) 204, and/or temperature sensor(s) 312 are not in operation and/or physiological parameters based on electrodes 202, electrodes 204, and/or temperature sensor(s) 312 are not determined, for example, until motion of the subject falls below such threshold value. This can advantageously reduce or prevent noise, inaccurate, and/or misrepresentative physiological data from being processed, transmitted, and/or relied upon. Additionally, a wearable device 100 can be configured such that, when motion is detected (for example, via processor(s) 302) above a threshold value, wearable device 100 begins determining and/or transmitting physiological parameters.

Some implementations of wearable device 100 can be utilized to determine whether a subject has fallen. For example, orientation and/or motion data can be obtained from a wearable device 100 to determine whether a subject has fallen. As another example, a wearable device 100 can communicate with an external device to indicate a subject has fallen. The wearable device 100 can incorporate motion sensor(s), associated structure(s), and/or associated methods of subject orientation, motion, position, and/or activity determination similar or identical those described and/or illustrated in U.S. Pat. No. 11,406,286 and/or U.S. Pat. Pub. No. 2021/0330200 incorporated by reference herein.

In some implementations, wearable device 100 includes one or more other sensors 320 and/or 208. For example, hub 300 can include one or more other sensors 320, and/or dock assembly 200 (for example, dock 201) can include one or more other sensors 208. Other sensor(s) 320, 208 can include one or more of an acoustic sensor (for example, a microphone), and/or one or more of an optical sensor (for example, a pulse oximetry sensor), among others. Such other sensor(s) 320, 208 can operably connect to processor(s) 302 for determination of body sounds of the subject such as cardiac function and/or lung function (in the case of an acoustic sensor), and/or for determination of one or more pulse oximetry values of the subject (in the case of an optical sensor).

Electrode(s) 202 (which can also be referred to herein as "ECG electrodes", "internal electrodes", or "internal ECG electrodes") and electrode(s) 204 (which can also be referred to herein as "ECG electrodes", "external electrodes", or "external ECG electrodes") can be configured to continuously or periodically measure and/or monitor cardiac activity (which can also be referred to herein as "cardiac electrical activity") of subject 1. Each electrode(s) 202, 204 can generate one or more signals responsive to detected cardiac activity and such one or more signals can be received by processor(s) 302 for determination of such cardiac activity and/or cardiac function of the subject. For example, such one or more signals can be used for ST/QT segment analysis, beat classification, and/or arrhythmia detection, among others.

Wearable device 100 (for example, the dock assembly 200) can include one or more electrode(s) 204. For example, wearable device 100 can include one, two, three, four, five, six, seven, or eight or more electrode(s) 204. Electrode(s) 204 can include a substrate configured to removably secure the electrode(s) 204 to subject 1 (for example, to skin of subject 1). The substrate can be configured to allow for repositioning of electrode(s) 204 if needed. The substrate can provide improved electrical conductivity between electrode(s) 204 and subject 1. The substrate can be waterproof. The substrate can be a silicone adhesive, for example. In some implementations, each of the electrode(s) 204 can include a design (such as a unique design) that can be used to provide instruction to a subject or a caregiver in placing and/or arranging electrode(s) 204 on a subject's body.

Wearable device 100 (for example, dock assembly 200, dock 201) can include one or more electrode(s) 202. For example, wearable device 100 can include one, two, three, four, five, six, seven, or eight or more electrode(s) 202. Electrode(s) 202 can be operably positioned by dock 201. Dock 201 can include one or more substrates, as described herein, that can secure dock 201 and electrode(s) 202 to subject 1. In some implementations, one of electrode(s) 202 is configured to be a ground or reference electrode.

In some implementations, wearable device 100 can be configured as a 3-lead ECG device. For this, wearable device 100 can include two electrodes 202 and two electrodes 204. The two electrodes 202 can be secured to an upper left chest of subject 1 via dock 201. One of such electrodes 202 can be configured as a "RL", "Right Leg", "Reference", or "Ground" electrode, and the other of such electrodes 202 can be configured as a "LA" or "Left Arm" electrode. One of such electrodes 204 can be configured as a "LL" or "Left Leg" electrode and can be configured to be secured to a lower left portion of a stomach of subject 1, and the other of such electrodes 204 can be configured as a "RR" or "Right Arm" electrode and can be configured to be secured to an upper right chest of subject 1. In some implementations, wearable device 100 can be configured as a 6-lead ECG device or have a different ECG lead configuration.

Wearable device 100 can incorporate electrode(s), associated structure(s), and/or associated methods of subject cardiac activity and/or cardiac function determination similar or identical those described and/or illustrated in U.S. Pat. Pub. No. US2022/0233128 incorporated by reference herein.

Figure 2A:
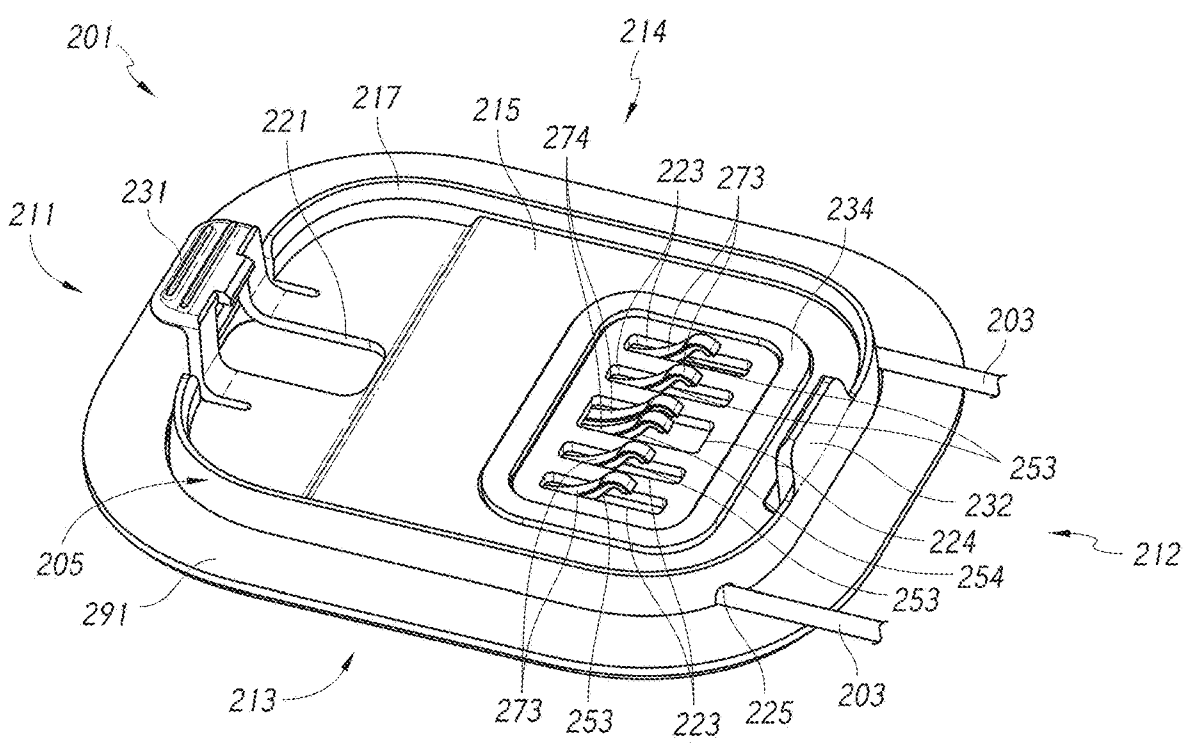
FIGS. 2A-2B illustrate top perspective views of a dock of the dock assembly of FIGS. 1C-1D in accordance with aspects of this disclosure.
Figure 2B:
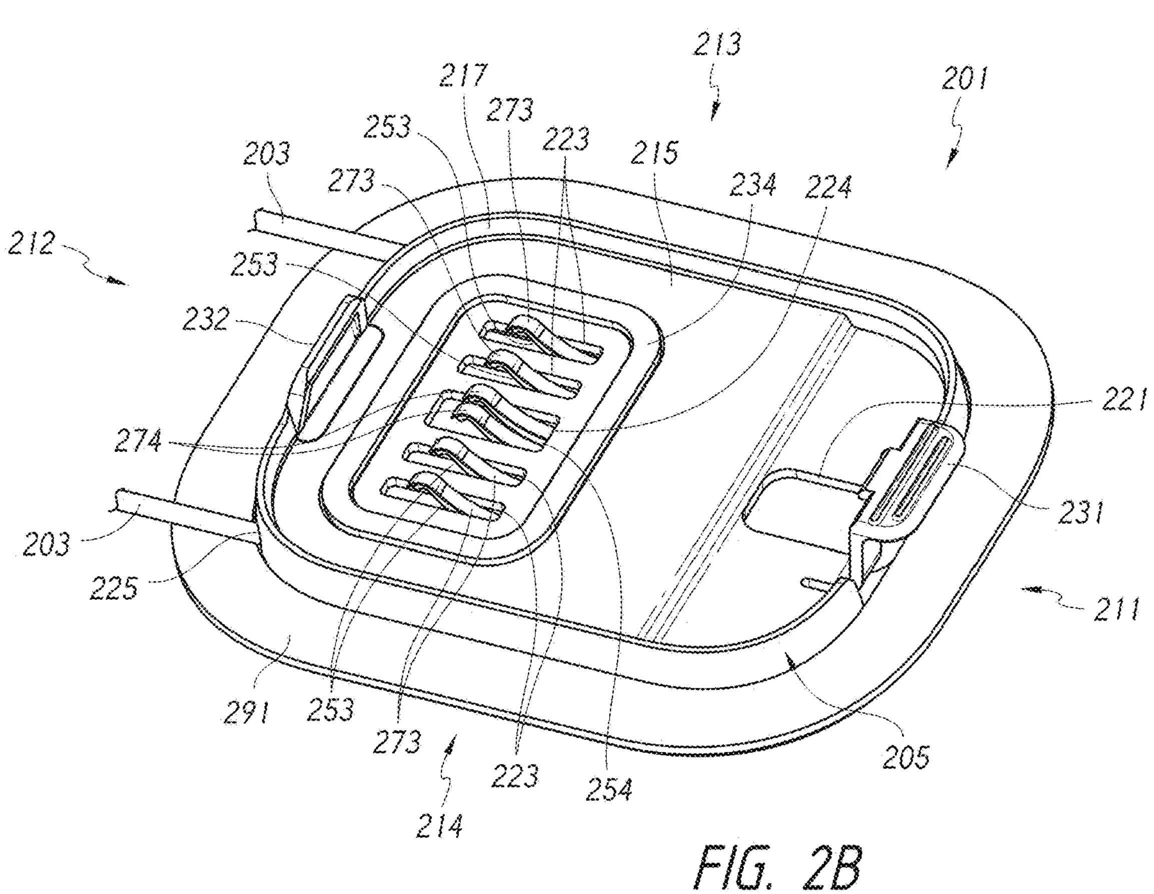
Figure 2C:
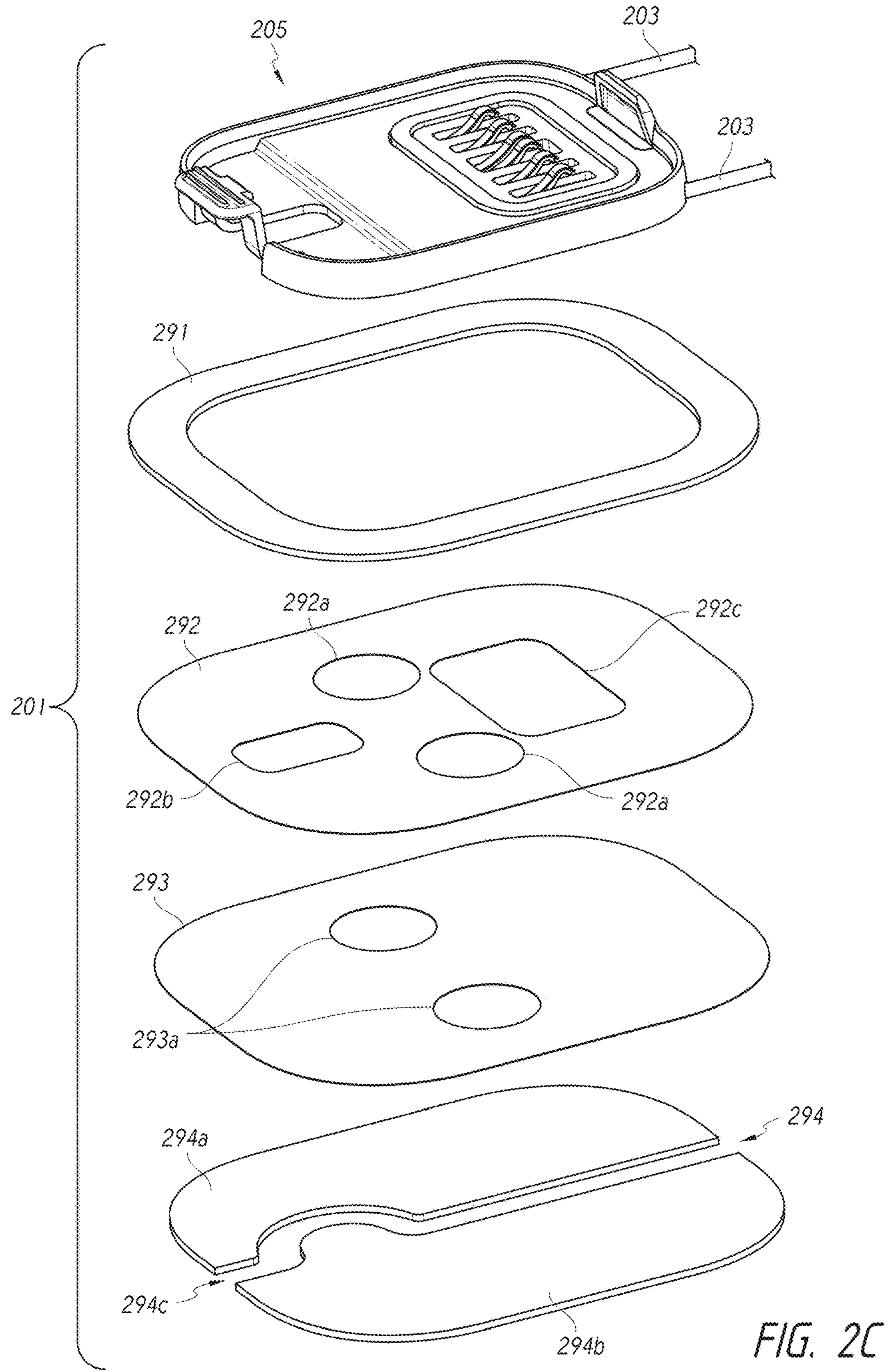
FIG. 2C illustrates an exploded, top perspective view of the dock of FIGS. 2A-2B in accordance with aspects of this disclosure.
Figure 2D:
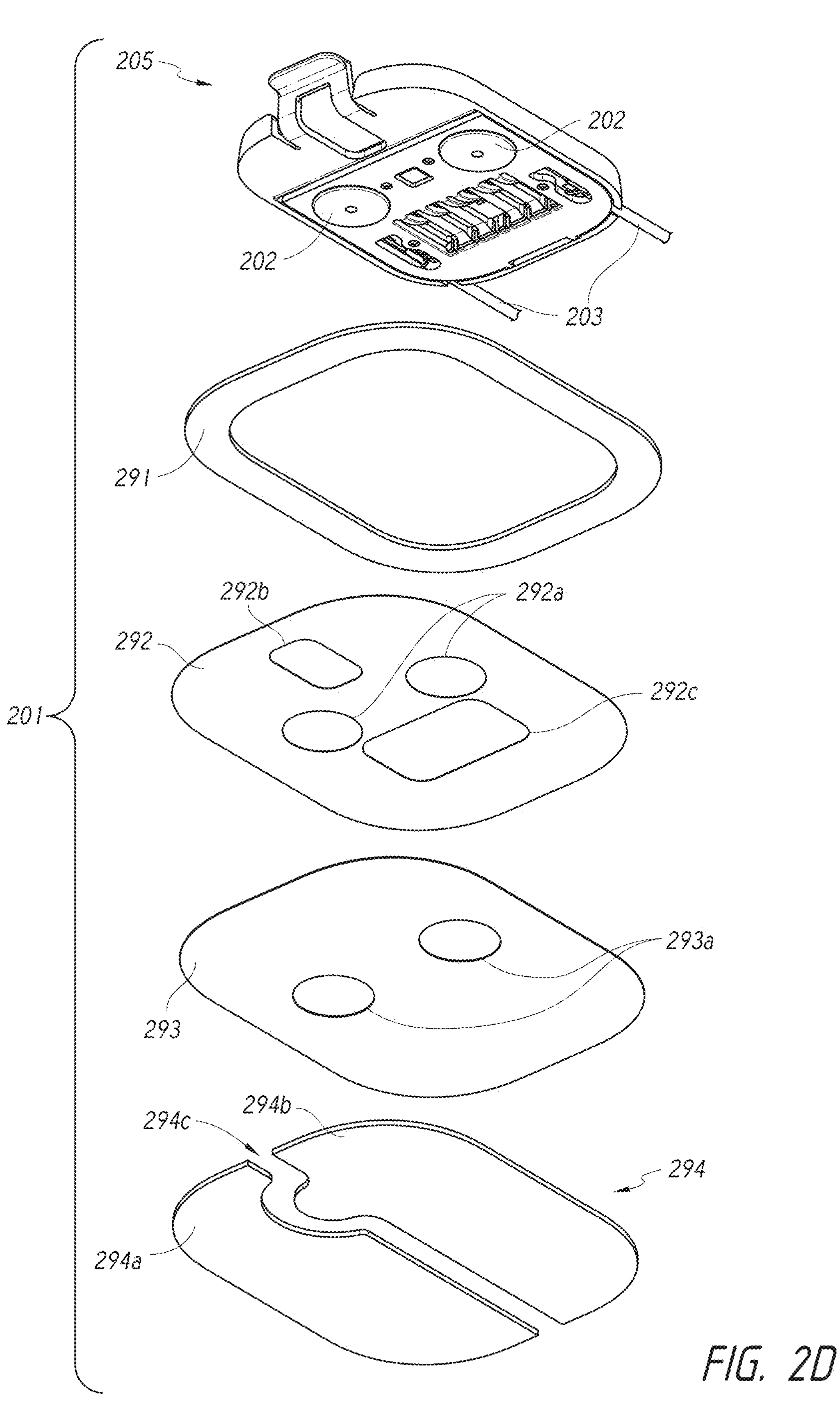
FIG. 2D illustrates an exploded, bottom perspective view of the dock of FIGS. 2A-2B in accordance with aspects of this disclosure.
Figure 2E:
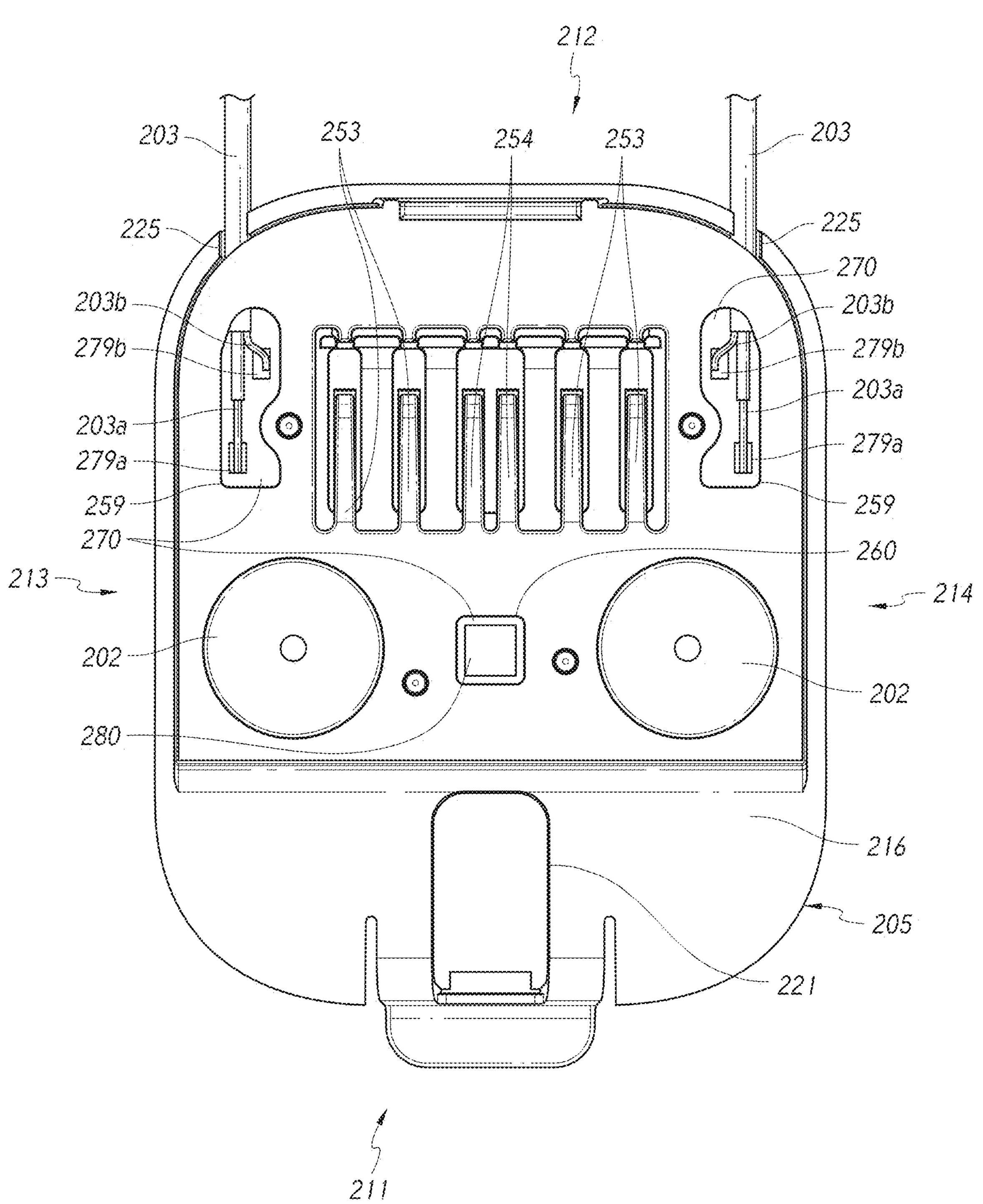
FIG. 2E illustrates a bottom view of a frame and electrical components of the dock of FIGS. 2A-2B in accordance with aspects of this disclosure.

FIGS. 2A-2E illustrate various views of dock 201 of wearable device 100. FIGS. 2A-2B illustrate top perspective views of dock 201, FIGS. 2C-2D illustrate exploded perspective views of dock 201, and FIG. 2E illustrates a bottom view of a portion of dock 201. Dock 201 can have a first end 211, a second end 212 opposite first end 211, a first side 213, and a second side 214 opposite first side 213. Dock 201 (which can also be referred to herein as a "base") can include one or more substrates, such as substrates 291, 292, 293 and/or 294 shown in FIGS. 2C-2D. Dock 201 can also include a frame 205 coupled to the one or more substrates (for example, coupled to at least one of the substrates 291, 292, 293 and/or 294). Dock 201 can include one or more mechanical connectors, such as mechanical connectors 231 and/or 232, configured to secure (for example, removably secure) hub 300 to dock 201 (for example, to secure hub 300 to dock assembly 200). Further as shown, dock 201 can include a circuit layer, such as dock circuit layer 270 (which can also be referred to herein as a "circuit substrate" or a "flexible circuit layer"). Such circuit layer can include a plurality of conductive strips, such as conductive strip(s) 273 (which can be referred to herein as "electrode conductive strips") and/or conductive strip(s) 274 (which can be referred to herein as "information element conductive strips"). Dock 201 can include a plurality of prongs, such as prong(s) 253 (which can also be referred to herein as "fingers") and/or prong(s) 254 (which can also be referred to herein as "fingers"). The plurality of conductive strips of the circuit layer can be positioned along the plurality of prongs. In some implementations, dock 201 includes and operably positions electrode(s) 202 described herein. Furthermore, in some implementations, dock 201 includes an opening, such as opening 221 (which can be referred to herein as a "probe opening"), configured to receive one or more portions and/or components of hub 300 (for example, wall 345 and/or thermally conductive probe 374 of hub 300 described herein) at least partially therethrough. Dock 201 can also include one or more components configured to create a seal (for example, a water-tight or substantially water-tight seal) with hub 300 when hub 300 is secured thereto, such as gasket 234.

Mechanical connectors 231, 232 can be configured to engage corresponding mechanical connectors of hub 300 (for example, mechanical connectors 341, 342 of hub 300 described herein) to hold hub 300 in place with respect to dock 201. Mechanical connector 231 can be proximate first end 211 and mechanical connector 232 can be proximate second end 212 of dock 201. Frame 205 can include such mechanical connectors 231, 232. Mechanical connector 231 can be, for example, a clip that extends outward from a first surface 215 of frame 205 and can be configured to bend and/or flex (for example, when securing and/or removing hub 300 to/from dock 201). Such first surface 215 can face towards hub 300 when hub 300 is secured to frame 205 (for example, when hub 300 is secured to dock 201). Mechanical connector 231 can include a protrusion that can extend in a direction towards second end 212 (for example, towards mechanical connector 232) configured to aid in securing hub 300 to dock 201. Mechanical connector 232 can be, for example, a catch that extends outward from first surface 215 of frame 205. Furthermore, mechanical connector 232 can include a recess that extends inward in a direction towards second end 212 configured to aid in securing hub 300 to dock 201. The interaction of mechanical connectors 231, 232 and corresponding mechanical connectors of hub 300 (for example, mechanical connectors 341, 342 of hub 300) can advantageously allow and maintain electrical communication between dock 201 and hub 300. In some variants, dock 201 includes less than two mechanical connectors or more than two mechanical connectors. For example, in some variants, dock 201 includes only one of mechanical connectors 231, 232.

Frame 205 can include a wall 217 extending from first surface 215 and along and/or around (for example, at least partially along and/or around) an exterior and/or perimeter of frame 205. Wall 217 can be configured (for example, sized and shaped) to receive a perimeter of hub 300. Frame 205 (for example, proximate and/or through wall 217) can include opening(s) 225 configured to receive cable(s) 203 connected to electrode(s) 204. For example, frame 205 can include an opening 225 for each cable 203 connected to dock 201. Such opening(s) 225 can be proximate second end 212 of dock 201 as shown, however this is not intended to be limiting.

Frame 205 can include prong(s) 253 and/or prong(s) 254. Prong(s) 253, 254 can extend outward from first surface 215 of frame 205, thereby positioning associated conductive strip(s) 273, 274 of dock circuit layer 270 outward from first surface 215 of frame 205. In some implementations, conductive strip(s) 273, 274 can be operably positioned by and/or coupled to (for example, positioned along) the prong(s) 253, 254, respectively. Each of the conductive strip(s) 273, 274 can be coupled to, positioned along, and or operably positioned by a different one of the prong(s) 253, 254. Prong(s) 253, 254, conductive strip(s) 273, 274, dock circuit layer 270, and frame 205 are described further with respect to FIGS. 3A-3D.

Opening 221 of dock 201 can be proximate first end 211 of dock 201. Frame 205 can include opening 221. Opening 221 can extend from first surface 215 (which can also be referred to herein as "top") of frame 205 to a second surface 216 (which can also be referred to herein as "bottom") of frame 205 that is opposite first surface 215 (for example, opening 221 can extend through a portion of frame 205). As described above, opening 221 can be configured to receive at least a portion of thermally conductive probe 374 of hub 300 at least partially therethrough. Opening 221 can also be configured to receive at least a portion of wall 345 of hub 300 at least partially therethrough.

Referring to FIGS. 2C-2D, dock 201 can include one or more of substrates 291, 292, 293 and/or 294. Substrate 291 can comprise foam and can be configured to surround frame 205 when dock 201 is assembled. Substrate 291 can include an opening sized and/or shaped to match a size and/or shape of a perimeter of frame 205.

Substrate 292 can comprise an adhesive material configured to secure substrate 291 and/or second surface 216 of frame 205 to substrate 230 and/or to substrate 231. Substrate 292 can be, for example, a double-sided adhesive layer. Substrate 292 can include one or more of openings **292*a*, 292*b*, 292*c*. Openings 229*a* can be sized and/or shaped to allow electrode(s) 202 to contact portion(s) of substrate 294. The number of openings 229*a* can correspond to the number of electrode(s) 202. Openings 229*a* can be dimensioned to receive electrode(s) 202. Opening 229*b* can be positioned proximate opening 221 of frame 205 and can be configured to allow thermally conductive probe 374 and/or wall 345 of hub 300 to contact a portion of substrate 293 when hub 300 is secured by dock 201. In some implementations, opening 229*a* is sized and/or shaped substantially similar to opening 221. Opening 292*c* can be positioned proximate prong(s) 253, 254 and sized and/or shaped substantially similar to an opening 257 of a portion of frame 205 discussed with respect to FIGS. 3A-3C**.

Substrate 293 can be secured (for example, adhered) to substrate 292 as discussed above. Substrate 293 can include openings **293*a* sized and/or shaped to allow electrode(s) 202 to contact portion(s) of substrate 294. The number of openings 293*a* can correspond to the number of electrodes 202. Openings 230*a* can be dimensioned to receive electrode(s) 202. As discussed above, opening 292*b* of substrate 292 can be sized and/or shaped to allow thermally conductive probe 374 and/or wall 345 of hub 300 to contact a portion of substrate 293 when hub 300 is secured by dock 201. Advantageously, substrate 293 can comprise a thermally conductive material configured to provide thermal communication between the subject's skin and thermally conductive probe 374. Substrate 293 can comprise an electrically isolative material which can advantageously minimize or eliminate electrical interference between the subject's skin and portions of dock 201 in areas other than openings 293*a*. Substrate 293** can be, for example, a polyethylene (PE) film.

Substrate 294 can be secured (for example, adhered) to substrate 293 and can be a bottommost layer of dock 201. Substrate 294 can be configured to contact skin of subject 1 when dock 201 is secured to subject 1. Substrate 294 can be configured to secure to skin of subject 1, thereby securing dock 201 to the subject 1. For this, substrate 294 can include an adhesive material. In some implementations, substrate 294 is the only portion of dock 201 that contacts subject 1 (e.g., substrate 294 can be positioned between electrode(s) 202 and/or thermally conductive probe 374, if included, and the subject's skin). In some implementations, substrate 294 comprises substrates **294*a* and 294*b* that are separated from one another by a channel 294*c*. Such separation between substrates 294*a* and 294*b* can provide electrical isolation between two electrodes 202 (where two are included in dock 201) such that the two substrates 294*a* and 294*b* (and respective electrodes 202 coupled thereto) make independent electrical contact with the subject's skin. In some implementations, channel 294*c* is substantially straight. In some implementations, channel 294*c* comprises a straight portion and a portion that is at least partially curved (for example, comprises a serpentine shape). Substrate 294 can comprise an electrically conductive material. In some implementations, substrate 294 comprises a thermally conductive material. Substrate 294** can comprise hydrogel, for example.

In some implementations (not shown), dock 201 can include a release liner configured to be secured to one or more of the above-described substrates and further configured to be removed prior to securement of the dock 201 to subject 1. Such release liner can cover substrate 294, for example, and/or have the same or similar shape or external perimeter as substrate 294. Furthermore, such release liner can include a tab configured to assist in removing the release liner from one or more of the above-described substrates.

FIG. 2E illustrates a bottom view of dock 201 without substrates 291, 292, 293 and 294. In this bottom view, second surface 216 (which faces the subject 1 when the dock 201 is secured to the subject 1) of frame 205 and various electrical components of dock 201 are visible. As shown, frame 205 can include an opening 260 that extends at least partially therethrough and configured to receive information element 280 of dock 201 and dock assembly 200. Information element 280 can be coupled to dock circuit layer 270 and can, as described herein, be used to verify dock 201 and dock assembly 200 as an authorized product. Also shown, frame 205 can include opening(s) 259 that extend at least partially therethrough and positioned proximate the connections between cable(s) 203 and dock circuit layer 270. Each of cable(s) 203 can include a first wire 203*a* that is electrically connected to a different one of conductive pad(s) 279*a*. Additionally, each of cable(s) 203 can include a second wire 203*b* that is electrically connected to a different one of ground pad(s) 279*b*.

Figure 3A:
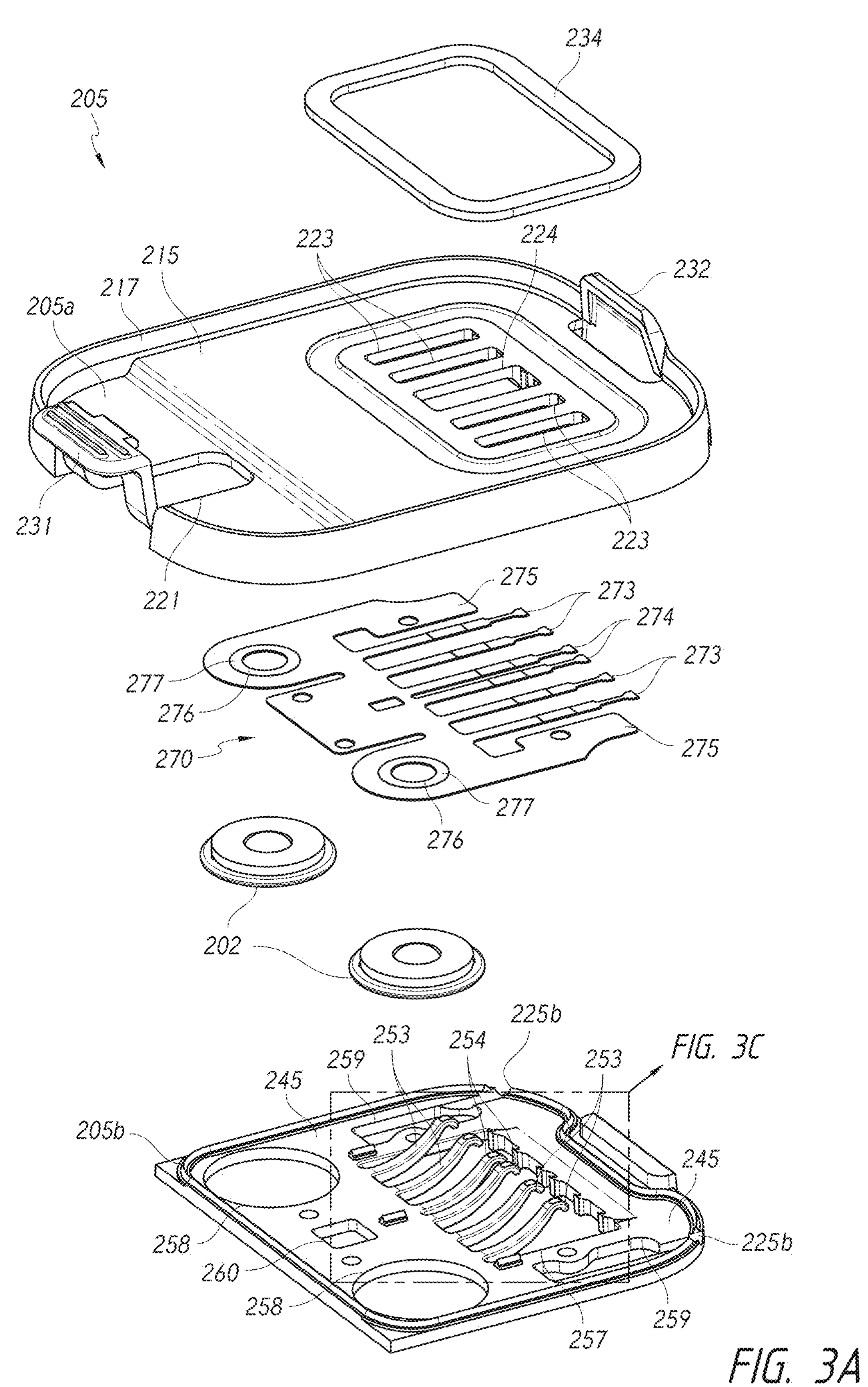
FIGS. 3A-3B illustrate exploded, top and bottom perspective views, respectively, of a frame and electronic components of the dock of FIGS. 2A-2B in accordance with aspects of this disclosure.
Figure 3B:
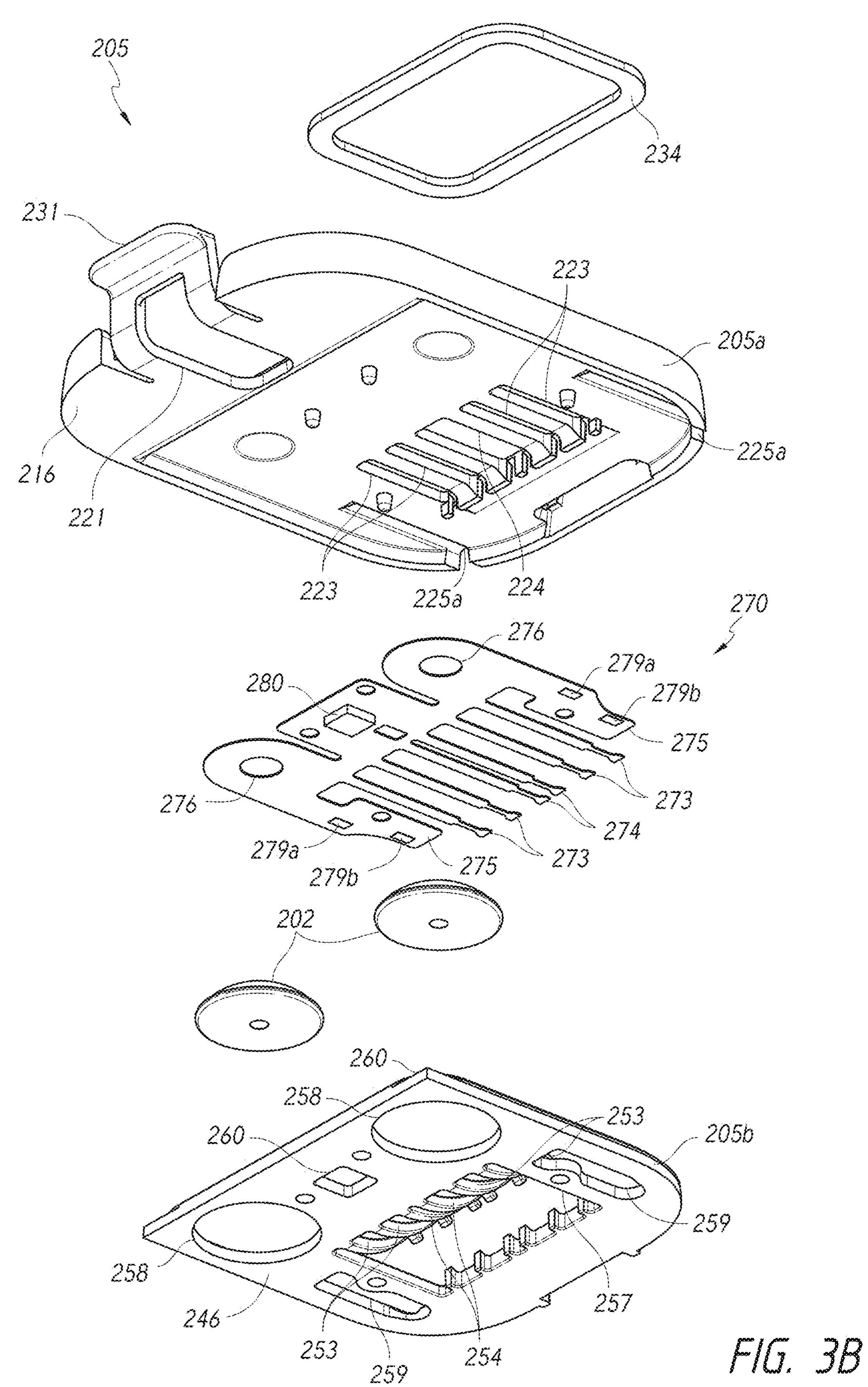

FIGS. 3A-3B illustrate exploded perspective views of frame 205 and electronic components of dock 201. As shown, frame 205 can comprise a main body 205*a* (which can also be referred to herein as a "first portion") and a plate 205*b* (which can also be referred to herein as a "second portion"). Main body 205*a* and plate 205*b* can be configured to couple to one another to form frame 205. Further as shown, dock circuit layer 270 can be positioned in between main body 205*a* and plate 205*b*. For this, main body 205*a* and plate 205*b* can include features configured to secure dock circuit layer 270 in place with respect to frame 205.

Main body 205*a* can include first surface 215, second surface 216, wall 217, mechanical connectors 231, 232, opening 221, and opening(s) 225*a* that form a first part of opening(s) 225 of frame 205. Main body 205*a* can also include a plurality of openings 223 that extend through main body 205*a*. Opening(s) 223 can be configured to receive therethrough conductive strip(s) 273 positioned along prong(s) 253. Main body 205*a* can also include an opening 224 that extends through main body 205*a*. Opening 224 can be configured to receive therethrough conductive strip(s) 274 positioned along prong(s) 254. Gasket 234 described herein can be positioned proximate and/or around opening(s) 223 and openings 224 at first surface 215.

Plate 205*b* can include a first surface 245 and a second surface 246 opposite first surface 245. First surface 245 of plate 205*b* can face towards main body 205*a* when coupled thereto. Plate 205*b* can include opening 260, opening(s) 259, opening(s) 225*b* that form a second part of opening(s) 225, prong(s) 253, and prong(s) 254 of frame 205. Plate 205*b* can also include opening(s) 258 configured to operably position electrode(s) 202. Further as shown, plate 205*b* can include opening 257 that at least partially surrounds prong(s) 253 and prong(s) 254.

Dock circuit layer 270 can include conductive strip(s) 273 and conductive strip(s) 274 as described herein. Conductive strip(s) 273 and conductive strip(s) 274 can be configured to be flexible so as to be positionable along prongs(s) 253 and prong(s) 254, respectively. Dock circuit layer 270 can include arms 275 comprising conductive pad(s) 279*a* and ground pad(s) 279*b* described with respect to FIG. 2E. As shown, information element 280 can be electrically connected to dock circuit layer 270. Dock circuit layer 270 can include opening(s) 276 surrounded by conductive ring(s) 277. Opening(s) 276 can be configured to receive and/or position at least a part of electrode(s) 202. Conductive ring(s) 277 can be configured to electrically connect electrode(s) 202 to dock circuit layer 270. Dock circuit layer 270 can be configured to electrically isolate each of electrode(s) 202 and/or each of electrode(s) 204 (when included). Furthermore, dock circuit layer 270 can be configured such that each of electrode(s) 202 and/or each of electrode(s) 204 (when included) can electrically connect to a different one of conductive strip(s) 273. Dock circuit layer 270 can be configured to electrically isolate information element 280 from other electric components connected thereto. Furthermore, dock circuit layer can be configured such that information element 280 is electrically connected to at least one of conductive strip(s) 274.

Figure 3C:
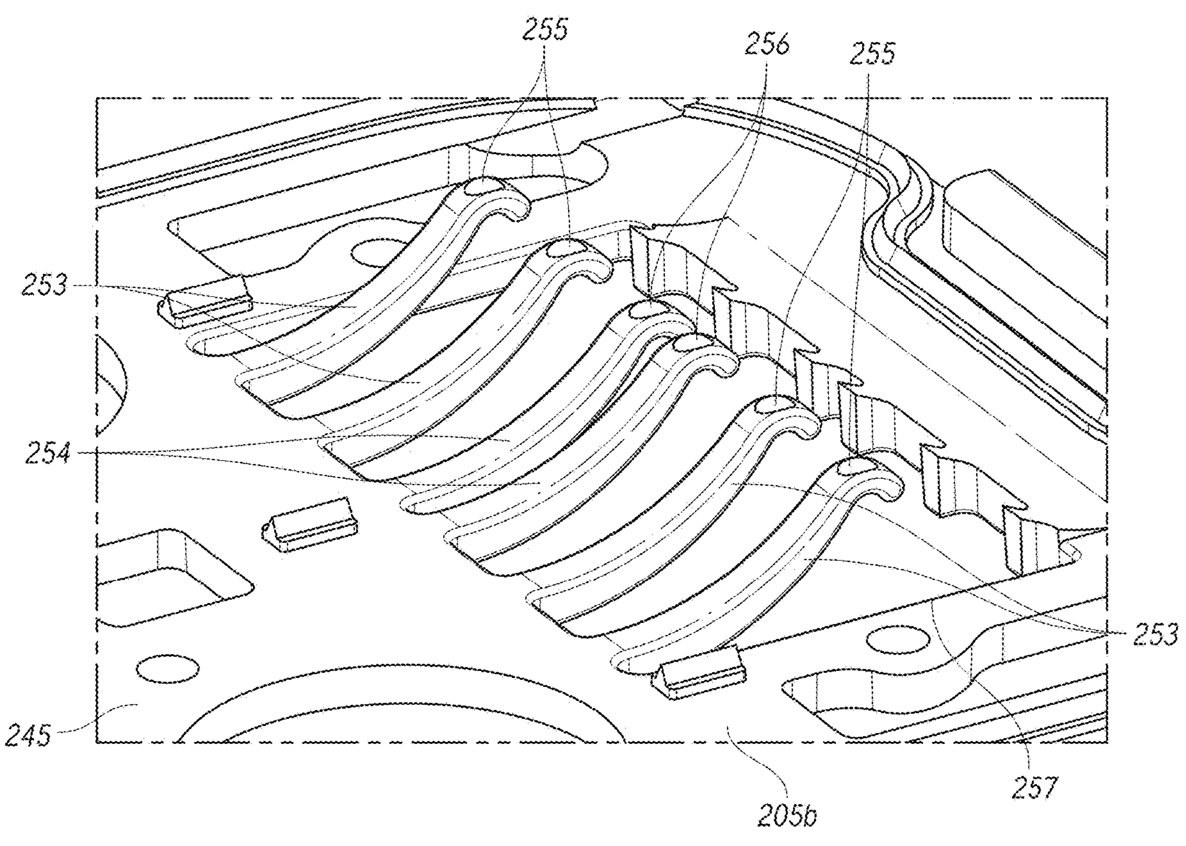
FIG. 3C illustrates an enlarged view of a portion of the frame as identified in FIG. 3A in accordance with aspects of this disclosure.
Figure 3D:
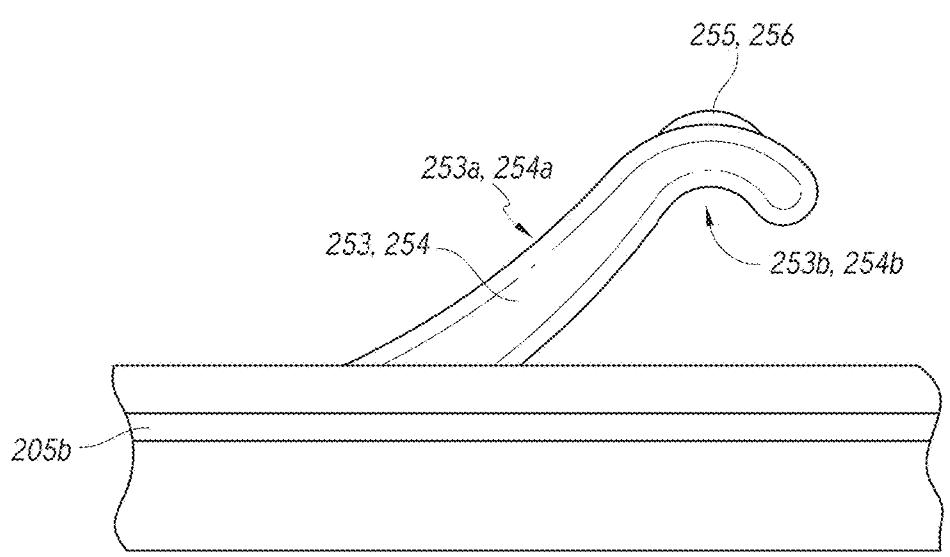
FIG. 3D illustrates a side view of a portion of the frame of FIG. 3A in accordance with aspects of this disclosure.

FIG. 3C illustrates an enlarged view of a portion of plate 205*b* of frame 205 as identified in FIG. 3A, and FIG. 3D illustrates a side view of a portion of plate 205*b* of frame 205. As described herein, prong(s) 253, 254 can extend outward from frame 205. As shown, prong(s) 253, 254 can extend outward from first surface 245 of plate 205*b*. Each of prong(s) 253, 254 can have a first end connected to a portion of frame 205 (for example, connected to a portion of plate 205*b*) and a second end opposite the first end. As shown, such second end of each of prong(s) 253, 254 can be cantilevered, for example over opening 257. Such configuration can allow prong(s) 253, 254 to function as springs when downward force is applied thereto (for example, when downward force is applied to or adjacent their second end). Prong(s) 253, 254 can be configured to be flexible and/or resilient. Each of prong(s) 253, 254 can include a curved portion that is closer to their respective second end than to their respective first end. When hub 300 and dock 201 are secured to one another, such curved portion of each of prong(s) 253, 254 can extend at least partially through respective openings of hub 300 (for example, opening(s) 333 and opening 334 of hub 300) and cause respective conductive strip(s) 273, 274 to contact portions of a hub circuit layer (for example, electrical contact(s) 376, 377 of hub circuit board 351 shown in FIG. 4L). Such contact between conductive strip(s) 273, 274 and portions of the hub circuit layer can electrically connect hub 300 with dock 201.

Each of prong(s) 253, 254 can have a convex portion 253*a*, 254*a*, respectively, and a concave portion 253*b*, 254*b*, respectively. The convex portion(s) 253*a*, 254*a* can be closer to the first end of each of prong(s) 253, 254. The concave portion(s) 253*b*, 254*b* can be closer to the second end of each of prong(s) 253, 254. The concave portion(s) 253*b*, 254*b* can comprise a smaller amount of a length of each of prong(s) 253, 254, be shorter than convex portion(s) 253*a*, 254*a*, and/or have a smaller radius of curvature than convex portion(s) 253*a*, 254*a*. When hub 300 and dock 201 are secured to one another, such concave portion(s) 253*b*, 254*b* of each of prong(s) 253, 254 can extend at least partially through respective openings of hub 300 (for example, opening(s) 333 and opening 334 of hub 300) and cause respective conductive strip(s) 273, 274 to contact portions of the hub circuit layer (for example, electrical contact(s) 376, 377 of hub circuit board 351 shown in FIG. 4L). As mentioned above, such contact between conductive strip(s) 273, 274 and portions of the hub circuit layer can electrically connect hub 300 with dock 201.

Figure 4K:
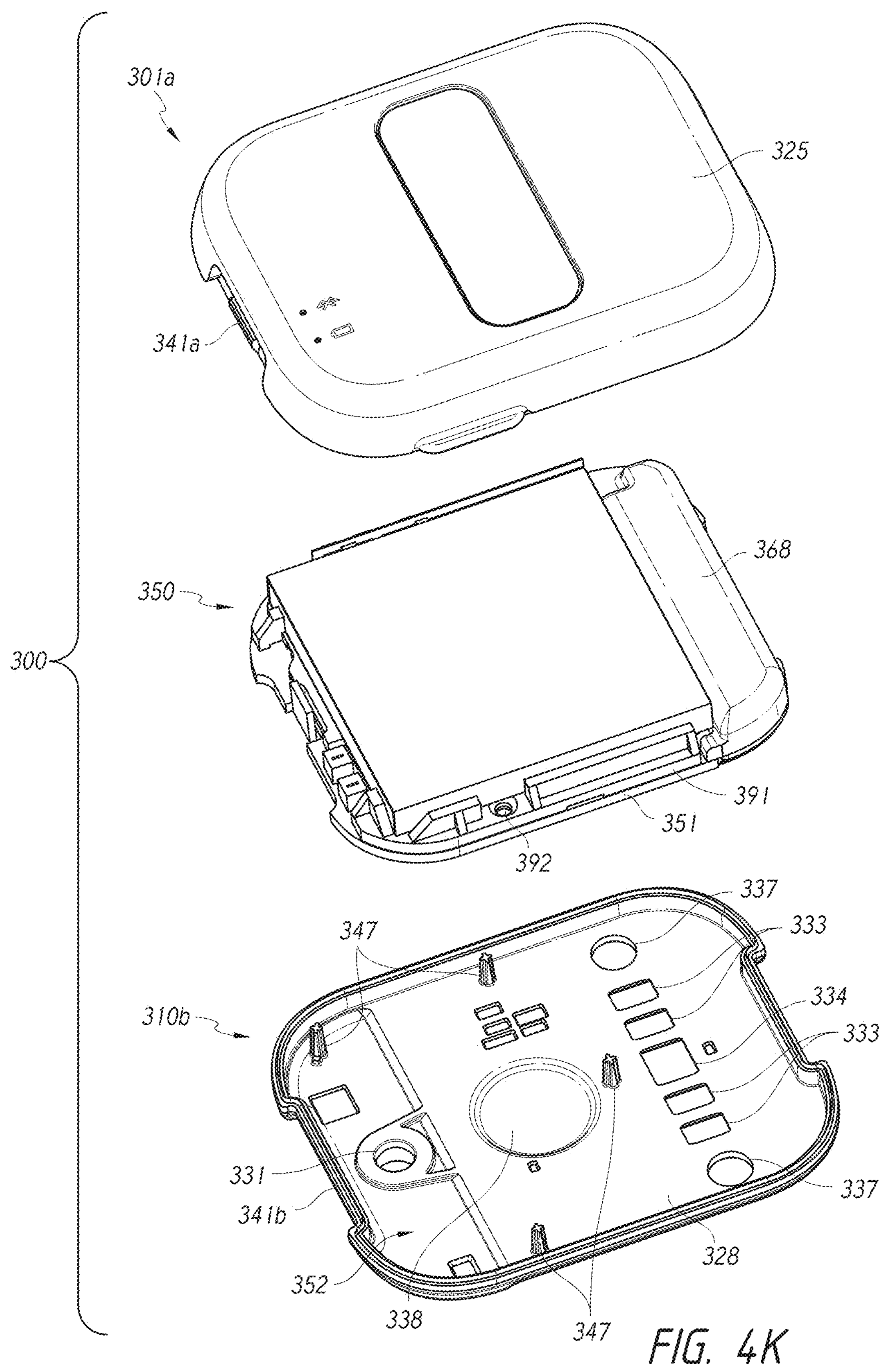
FIG. 4K illustrates an exploded, top perspective view of the hub of FIGS. 1C-1D in accordance with aspects of this disclosure.
Figure 4L:
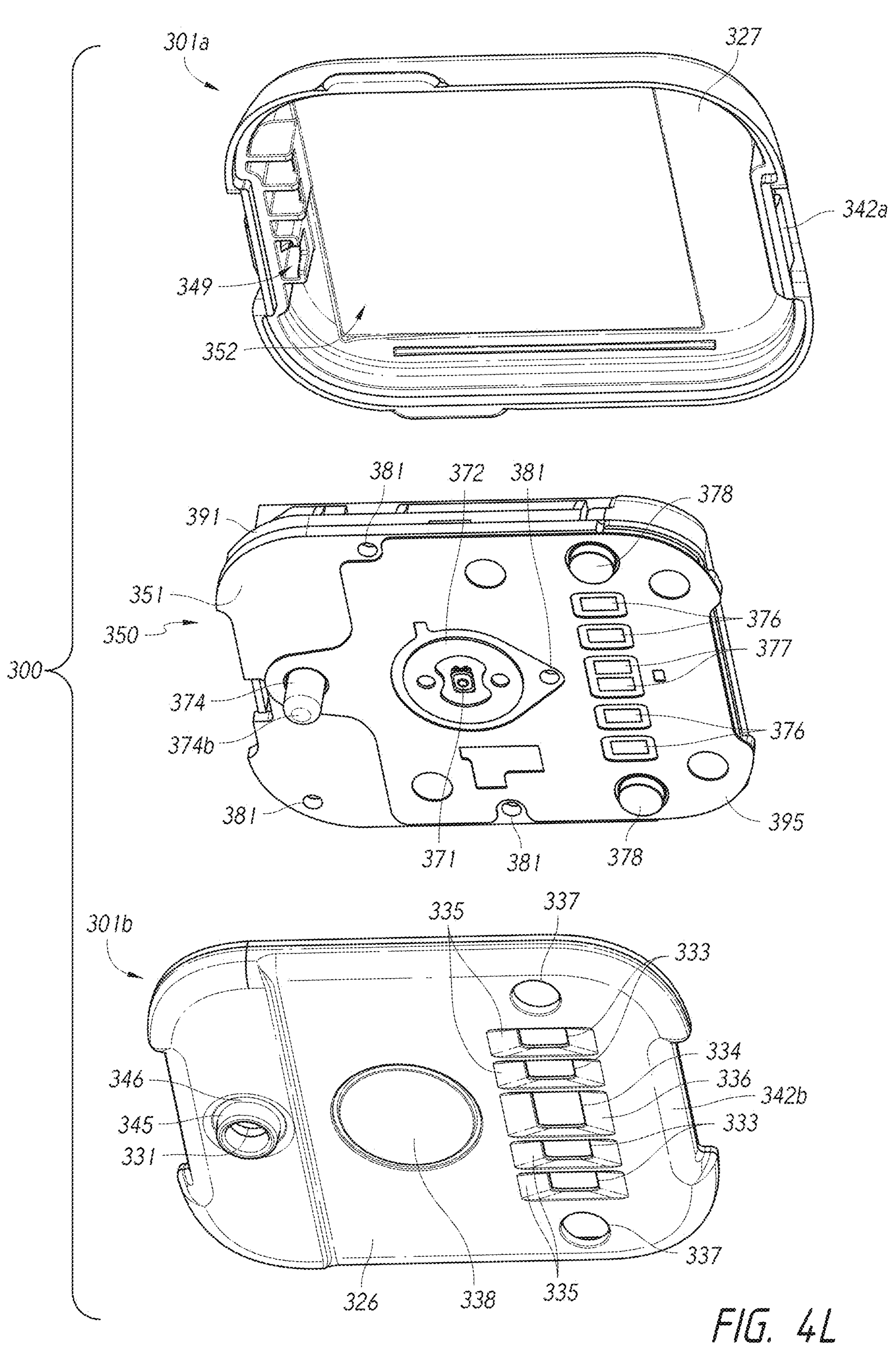
FIG. 4L illustrates an exploded, bottom perspective view of the hub of FIGS. 1C-1D in accordance with aspects of this disclosure.

Each of prong(s) 253, 254 can include a bump 255, 256, respectively, configured to facilitate contact between conductive strip(s) 273, 274 and portions of the hub circuit layer (for example, electrical contact(s) 376, 377 of hub circuit board 351 shown in FIG. 4L). Concave portion(s) 253*b*, 254*b* of prong(s) 253, 254 can include such bump(s) 255, 256 as shown. In some implementations, bump(s) 255, 256 comprise a rounded protrusion.

FIGS. 4A-4J illustrate various views of hub 300 of wearable device 100. FIGS. 4A-4B illustrate top perspective views of hub 300, FIG. 4C illustrates a bottom perspective view of hub 300, and FIGS. 4D-4I illustrate a top view, a bottom view, a first end view, a second end view, a first side view, and a second side view, respectively, of hub 300. Hub 300 can have a first end 321, a second end 322 opposite first end 321, a first side 323, a second side 324 opposite first side 323, a first surface 325 (which can also be referred to as a "top surface"), and a second surface 326 (which can also be referred to as a "bottom surface") opposite first surface 325. Hub 300 can be configured to mechanically and electrically connect with dock 201. Hub 300 can include one or more mechanical connectors, such as mechanical connectors 341 and/or 342, configured to secure (for example, removably secure) hub 300 to dock 201 and dock assembly 200. Hub 300 can include a circuit layer, such as circuit board 351 (which can also be referred to herein as a "hub circuit layer" or a "circuit substrate") shown in FIGS. 4K-6B. Hub 300 can include a plurality of openings, such as opening(s) 333 and/or opening(s) 334, each of which may also be referred to herein as "prong openings". Such plurality of openings can allow for conductive strip(s) 273, 274 of dock 201 to electrically connect with portions of the circuit layer of hub 300. Further shown, hub 300 can include ridges 329 configured to aid in handling hub 300 and/or aid in mating hub 300 with a charge cavity 420 of charger 400 described herein for charging battery 308 of hub 300. Hub 300 can include windows 317 configured to allow light emitted from status indicator(s) 316 to pass therethrough. Furthermore, hub 300 can include one or more electrical contacts and corresponding openings, such as electrical contact(s) 378 (which can also be referred to herein as "charger contacts") and associated openings 337, configured to allow battery 308 of hub 300 to receive power from a charging device (for example, charger 400 described herein). Hub 300 can include button 338 for actuating switch 371 as part of user input 314 described herein. Hub 300 can also include one or more components for thermally coupling a temperature sensor 312*a* with the subject's body, such as thermally conductive probe 374 extending through an opening 331. Additionally, hub 300 can include features for protecting such thermally conductive probe 374, such as wall 345 described further herein. Hub 300 can comprise housing 301, which can incorporate and/or operably position the features described above with respect to hub 300 and which can be configured to be secured to dock 201.

Mechanical connectors 341, 342 can be configured to engage corresponding mechanical connectors 231, 232 of dock 201. Mechanical connector 341 can be proximate first end 321, and mechanical connector 342 can be proximate second end 322. Mechanical connectors 341 can include a protrusion and a recess configured to releasably connect with the protrusion of the clip of mechanical connector 231 of dock 201. Mechanical connector 342 can include a protrusion and a recess configured to releasably connect with the catch of mechanical connector 232 of dock 201.

Opening(s) 333, 334 can extend through a portion of hub 300 (for example, a portion of housing 301) and be configured to receive at least a portion of conductive strips 273, 274, respectively, of dock 201 therethrough. In some implementations, opening(s) 333, 334 can be configured to receive at least a portion of prong(s) 253, 254, respectively, of dock 201 therethrough. Openings 333, 334 can be surrounded by inwardly tapered recesses 335, 336, respectively, as shown in at least FIG. 4C to aid in positioning portions of conductive strips 273, 274 carried by prong(s) 253, 254 through opening(s) 333, 334. For example, inwardly tapered recesses 335, 336 can guide prong(s) 253, 254 carrying conductive strips 273, 274 to and/or through openings 333, 334.

Figure 5A:
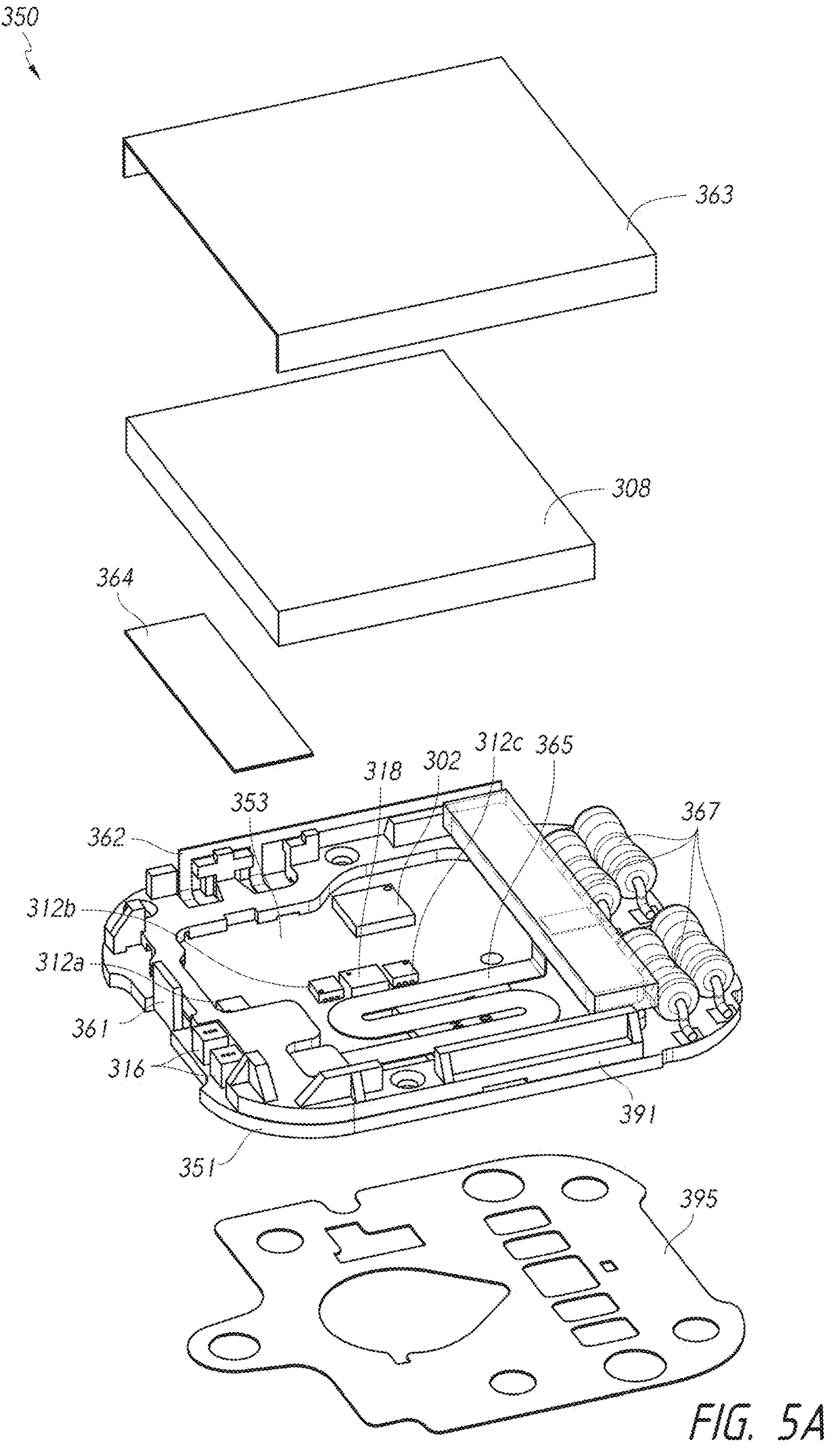
FIG. 5A illustrates an exploded, top perspective view of an electronics assembly of the hub of FIGS. 1C-1D in accordance with aspects of this disclosure.
Figure 5B:
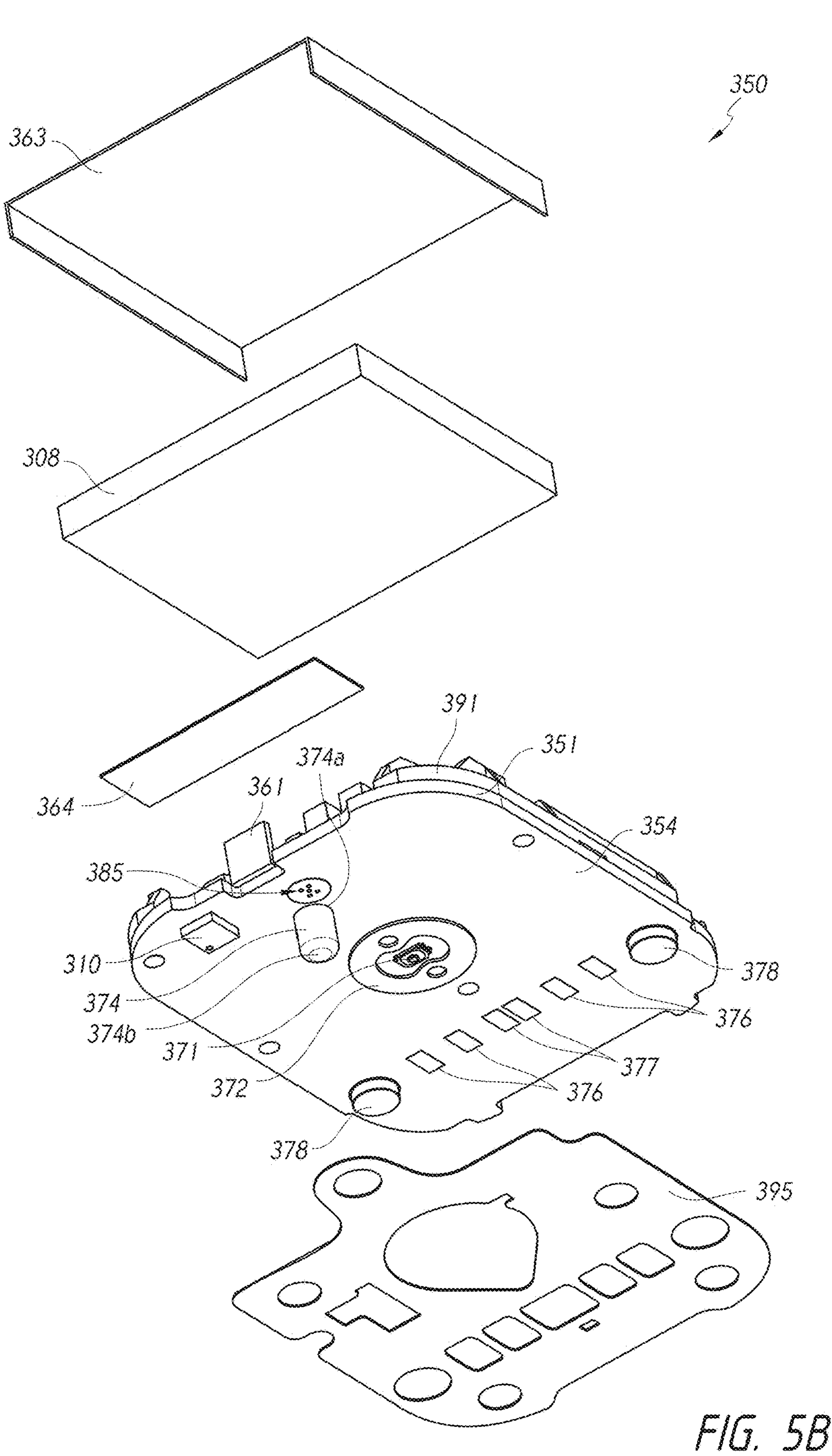
FIG. 5B illustrates an exploded, bottom perspective view of an electronics assembly of the hub of FIGS. 1C-1D in accordance with aspects of this disclosure.
Figure 7A:
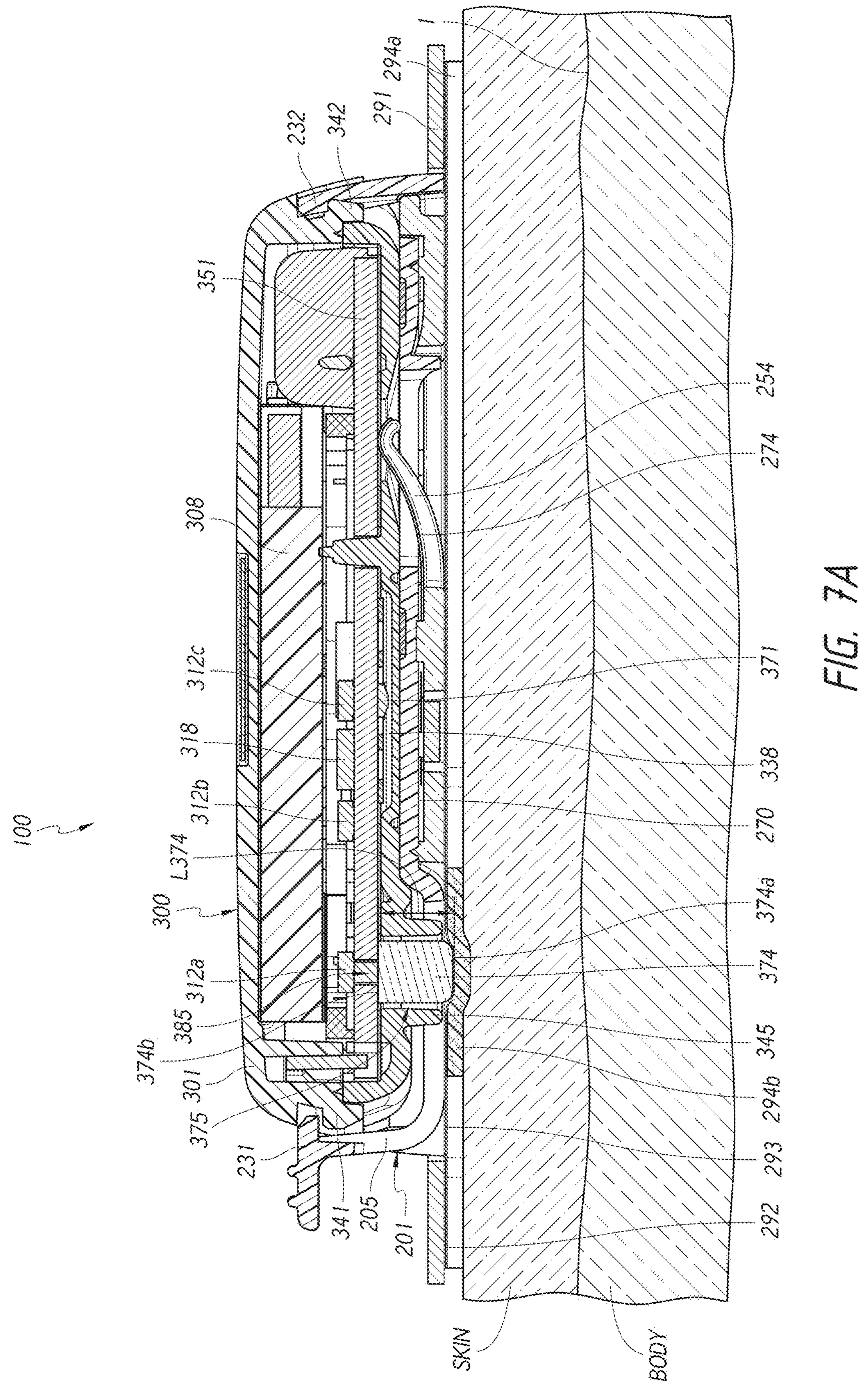
FIG. 7A illustrates a cross-sectional view as identified in FIG. 1B of a portion of the wearable device secured to a subject in an example condition of use in accordance with aspects of this disclosure.
Figure 7B:
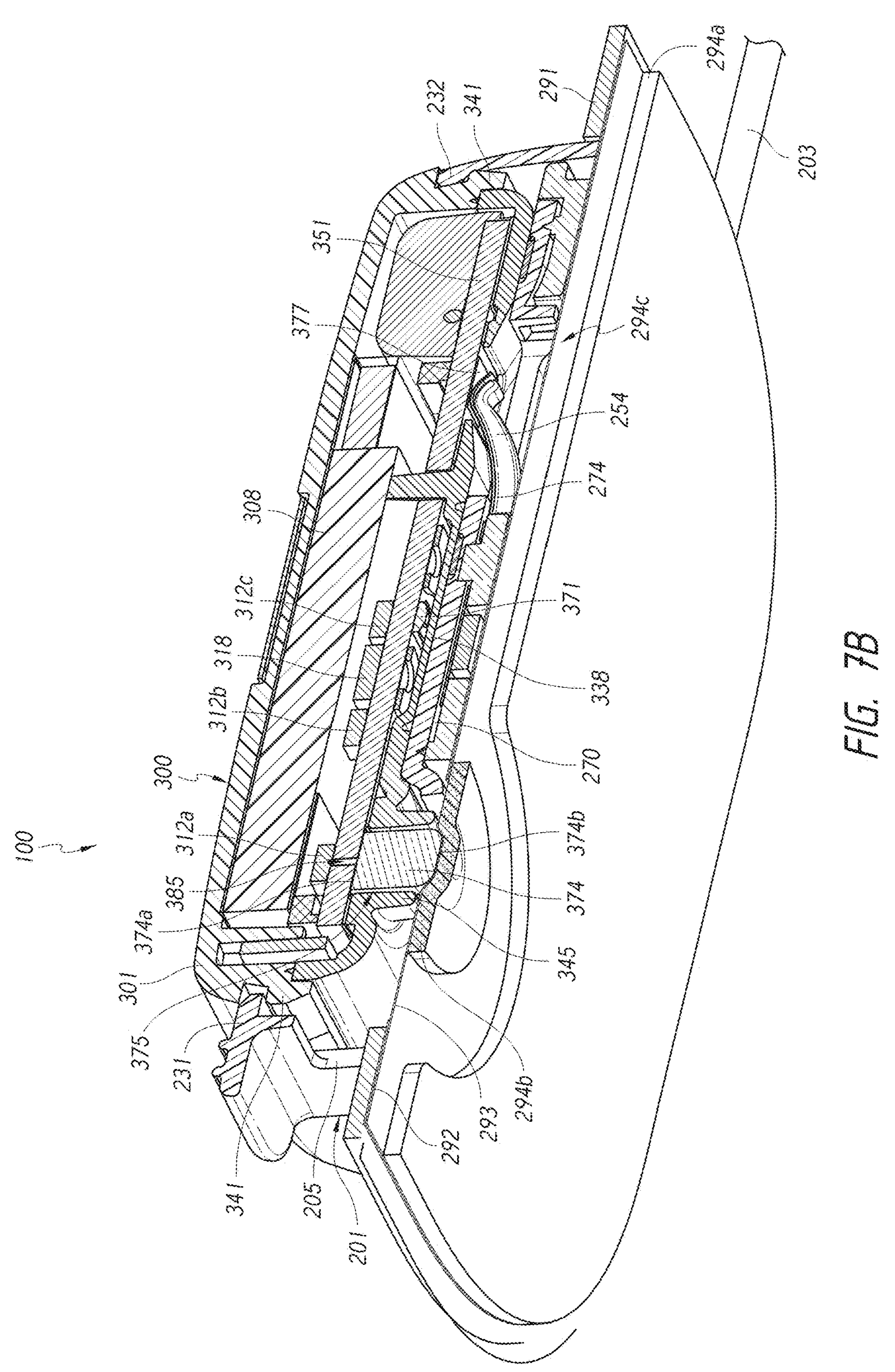
FIG. 7B illustrates a bottom perspective of the cross-sectional view as identified in FIG. 1B of a portion of the wearable device in accordance with aspects of this disclosure.

As described above and shown in FIGS. 4C-4I, in the enlarged view of a portion of hub 300 shown in FIG. 4J, in FIG. 4L, in FIG. 5B, and in FIGS. 7A-7B, hub 300 can include thermally conductive probe 374 that extends through housing 301. Thermally conductive probe 374 can have a first end 374*a* and a second end 374*b* opposite the first end. Furthermore, thermally conductive probe 374 can have a length L374 from first end 374*a* to second end 374*b*. First end 374*a* can couple to circuit board 351 and second end 374*b* can extend beyond housing 301. Hub 300 can include wall 345 that extends outward from housing 301 (for example, from second surface 326 thereof) and extends around at least a portion of thermally conductive probe 374. Wall 345 can surround an entire cross-section and/or perimeter of thermally conductive probe 374. In some implementations, wall 345 encircles thermally conductive probe 374. In some implementations, wall 345 is cylindrical and thermally conductive probe 374 is cylindrical. Wall 345 can be configured to protect thermally conductive probe 374, such as from physical impacts. In some implementations, wall 345 thermally insulates at least a portion of thermally conductive probe 374 (for example, to prevent or minimize thermal energy from dissipating from thermally conductive probe 374 as it transfers heat from subject 1 to temperature sensor 312*a* discussed herein). Wall 345 can be at least partially surrounded by a recess 346 in housing 301. As an example, recess 346 can comprise a circular recess that surrounds wall 345.

Wall 345 can extend an amount $L_{345}$ (which can also be referred to herein as a "length $L_{345}$") beyond second surface 326 of housing 301. Wall 345 can have a diameter (for example, an outer diameter) $D_{345}$. Thermally conductive probe 374 can extend an amount $L_{375}$ (which can also be referred to herein as a "length $L_{375}$") beyond wall 345. For example, second end 374*b* of thermally conductive probe 374 can extend beyond wall 345 such that second end 374*b* is exposed. Thermally conductive probe 374 can have a diameter $D_{374}$. A gap 375 can exist between thermally conductive probe 374 and wall 345.

In some implementations, thermally conductive probe 374 extends beyond wall 345 an amount (for example, $L_{375}$) that is less than about 5 mm, less than about 4.5 mm, less than about 4 mm, less than about 3.5 mm, less than about 3 mm, less than about 2.5 mm, less than about 2 mm, less than about 1.5 mm, less than about 1 mm, or less than about 0.5 mm. In some implementations, thermally conductive probe 374 extends beyond wall 345 an amount (for example, $L_{375}$) that is between about 0.1 mm and about 5 mm, between about 0.5 mm and about 4.5 mm, between about 1 mm and about 4 mm, between about 1.5 mm and about 3.5 mm, between about 2 mm and about 3 mm, between about 0.1 mm and about 5 mm, between about 0.1 mm and about 4.5 mm, between about 0.1 mm and about 4 mm, between about 0.1 mm and about 3.5 mm, between about 0.1 mm and about 3 mm, between about 0.1 mm and about 2.5 mm, between about 0.1 mm and about 2 mm, between about 0.1 mm and about 1.5 mm, between about 0.1 mm and about 1 mm, or between about 0.5 mm and about 1 mm. In some implementations, less than about 50% of a length of thermally conductive probe 374 extends beyond wall 345. For example, in some implementations, less than about 45%, less than about 40%, less than about 35%, less than about 30%, less than about 25%, less than about 20%, less than about 15%, or less than about 10% of a length (for example, L374) of thermally conductive probe 374 extends beyond wall 345.

In some implementations, a ratio between diameter $D_{345}$ of wall 345 and diameter $D_{374}$ of thermally conductive probe 374 can be between about 5.0 and about 1.1, between about 4.0 and about 1.2, between about 3.0 and about 1.3, or between about 2.0 and about 1.4. In some implementations, a ratio between diameter $D_{345}$ of wall 345 and diameter $D_{374}$ of thermally conductive probe 374 can be less than about 5.0, less than about 4.0, less than about 3.0, or less than about 2.0.

In some implementations, a gap (for example, gap 375) between thermally conductive probe 374 and wall 345 is less than about 2 mm, less than about 1.5 mm, less than about 1.2 mm, less than about 1.0 mm, less than about 0.8 mm, less than about 0.6 mm, less than about 0.5 mm, or less than about 0.4 mm. In some implementations, a gap (for example, gap 375) between thermally conductive probe 374 and wall 345 is between about 1.5 mm and about 0.2 mm, between about 1.2 mm and about 0.3 mm, between about 1.0 mm and about 0.3 mm, between about 0.8 mm and about 0.4 mm, between about 0.7 mm and about 0.4 mm, or between about 0.6 mm and about 0.4 mm.

Although wall 345 and thermally conductive probe 374 have been described in some implementations as having cylindrical shapes with diameters $D_{345}$, $D_{375}$, respectively, in some variants, wall 345 and/or thermally conductive probe 374 have different shapes, for example, square, or rectangular. In such variants, wall 345 and/or thermally conductive probe 374 can have lengths and/or widths that can be equivalent to any of the values or ranges described above with respect to diameters $D_{345}$, $D_{375}$.

FIGS. 4K-4L illustrate exploded, top and bottom perspective views, respectively of hub 300. As shown, housing 301 of hub 300 can include a top portion 301*a* (which can also be referred to herein as a "top shell") and a bottom portion 301*b* (which can also be referred to herein as a "bottom shell") configured to couple to one another. In some implementations, shells 301*a*, 301*b* are permanently secured to one another when hub 300 is assembled. Housing 301 can include an interior 352, such as formed by top portion 301*a* and bottom portion 301*b*. Top portion 301*a* can include first surface 325 of housing 300 and a bottom surface 327 opposite first surface 325. Bottom portion 301*b* can include second surface 326 of housing 300 and a top surface 328 opposite second surface 326. Further as shown, hub 300 can include electronics assembly 350. Electronics assembly 350 can be arranged within interior 352, such as by one or more features of housing 300.

Top portion 301*a* can include a first portion 341*a* of mechanical connector 341 and/or first portion 342*a* of mechanical connector 342 described herein. Bottom portion 301*b* can include a second portion 341*b* of mechanical connector 341 and/or a second portion 342*b* of mechanical connector 342 as described herein. Mechanical connectors 341 and/or 342 can thus be formed when top portion 301*a* and bottom portion 301*b* are coupled to one another.

Top portion 301*a* can include a cavity 349 configured to position NFC transponder 361 described herein. Bottom portion 301*b* can include opening 331, wall 345, and/or recess 346 (when included) as described herein. Bottom portion 301*b* can include button 338 described herein. Bottom portion can include opening(s) 337 described herein. Bottom portion 301*b* can include opening(s) 333, 334 and corresponding inwardly tapered recesses 335, 336 described herein. As shown in FIG. 4L, inwardly tapered recesses 335, 336 can taper inward from second surface 326 towards top surface 328.

Bottom surface 327 of top portion 301*a* and/or top surface 328 of bottom portion 301*b* can be configured to position electronics assembly 350 within interior 352 of housing 301. Bottom portion 301*b* can also include one or more posts 347 configured to position electronics assembly 350 within the interior 352 of housing 301. Portions of electronics assembly 350, such as circuit board 351 and/or a frame 391, can include one or more openings 381, 391, respectively, configured to receive post(s) 347 for such positioning. Frame 391 can be configured to aid in positioning electronics assembly 350 within interior 352. Electronics assembly 350 can also include a substrate 395 configured to secure (for example, adhesively secure) electronics assembly 350 to hub 300 (for example, to top surface 328 of bottom portion 301*b*). For this, substrate 395 can comprise a double-sided adhesive.

Electronics assembly 350 can include components of hub 300 shown and described with respect to FIG. 1E. For example, electronics assembly 350 can include processor(s) 302, storage device 304, communication module 306, battery 308, information element 310, temperature sensor(s) 312, at least a portion of user input 314, status indicator(s) 316, motion sensor 318, and/or other sensor(s) 320. Electronics assembly 350 can also include circuit board 351, frame 391, and components operably connected thereto shown in FIGS. 5A-6B. FIGS. 5A-5B illustrate exploded, top and bottom perspective views, respectively of electronics assembly 350. As shown and as described herein, electronics assembly 350 can include circuit board 351 and associated components, frame 391, and substrate 395. Use of the phrase "electronics assembly" and use of numeral "350" in the present disclosure is not intended to be limiting, but rather, is merely intended as a convenient method to refer to one or more components of hub 300 which can be enclosed by the shells 301*a*, 301*b*. The use of such phrase and such numeral is not intended to convey that the inclusion of any elements or features described with reference to electronics assembly 350 necessarily requires inclusion of any or all other elements or features described with reference to electronics assembly 350.

Figures 6A, 6B:
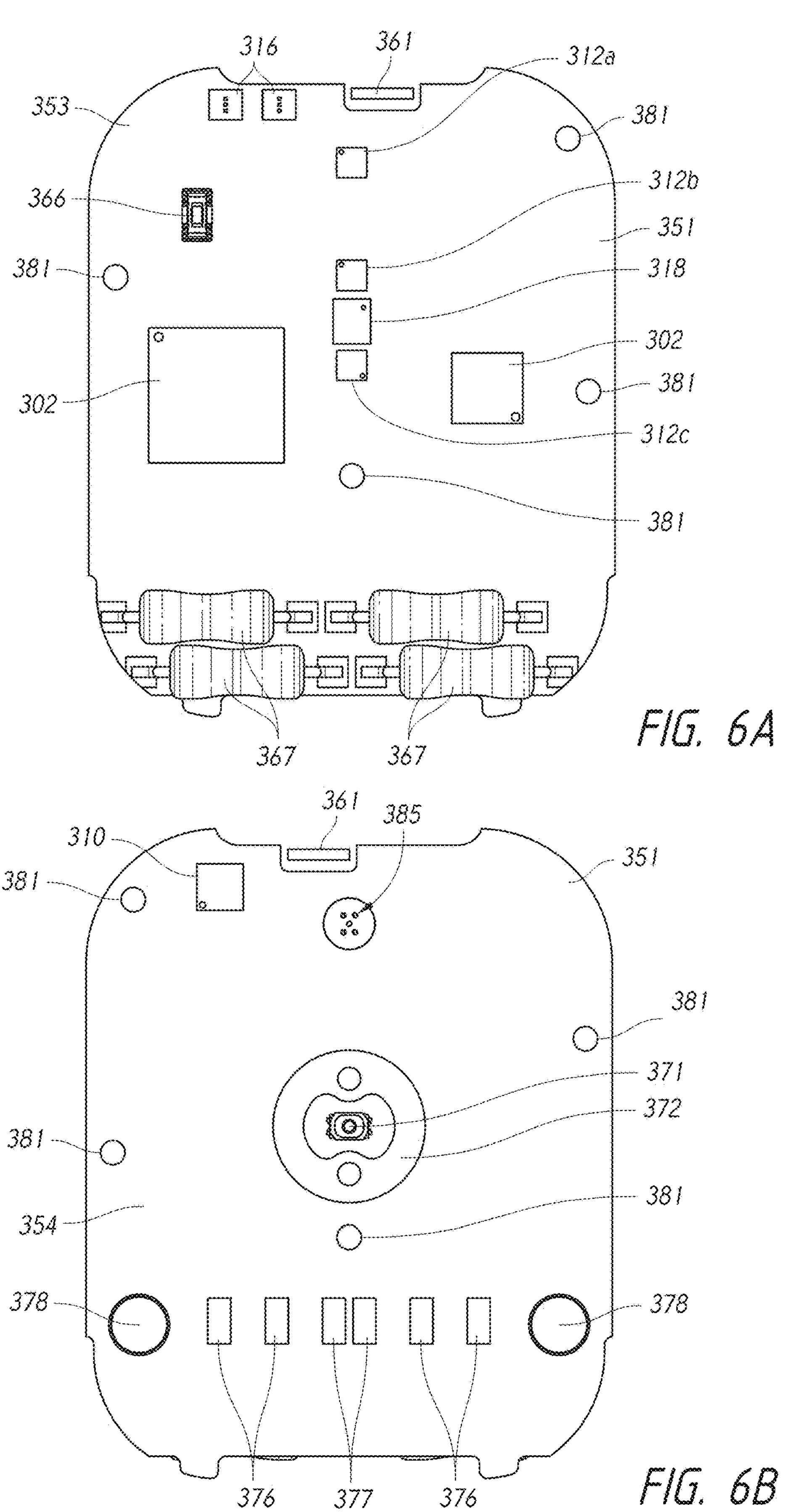
FIGS. 6A-6B illustrate top and bottom views, respectively, of a circuit layer of the hub of FIGS. 1C-1D in accordance with aspects of this disclosure.

As shown in FIGS. 5A-5B and in the top and bottom views, respectively, of circuit board 351 of FIGS. 6A-6B, circuit board 351 can have a first surface 353 and a second surface 354 opposite first surface 353. First surface 353 can face towards top portion 301*a* of housing 301, while second surface 354 can face towards bottom portion 301*b* of housing 301. With such arrangement, first surface 353 can face towards dock 201 when the hub 300 is secured by the dock 201.

Circuit board 351 can be operably coupled to temperature sensor(s) 312 (for example, temperature sensors 312*a*, 312*b*, and/or 312*c* when included), motion sensor 318, processor(s) 302, NFC transponder 361, antenna 362, status indicator(s) 316, one or more resistor(s) 367, battery 308, charger contact(s) 378, switch 371, information element 310, and/or thermally conductive probe 374. Temperature sensor(s) 312 (for example, temperature sensors 312*a*, 312*b*, and/or 312*c* when included), motion sensor 318, processor(s) 302, NFC transponder 361, antenna 362, status indicator(s) 316, one or more resistor(s) 367, and/or battery 308 can be operably coupled to first surface 353 as shown, although such arrangement is not intended to be limiting.

Charger contact(s) 378, switch 371, information element 310, and/or thermally conductive probe 374 can be operably coupled to second surface 354 as shown, although such arrangement is not intended to be limiting. Electrical contact(s) 376, 377 as discussed herein, can be positioned adjacent second surface 354. Hub 300 can include all components of electronics assembly 350.

Frame 391 can couple to first surface 353 of circuit board 351. In addition to aiding in positioning electronics assembly 350 within interior 352 of housing 301, frame 391 can include features for positioning battery 308 within interior 352 of housing 301. Battery 308 can be operably coupled to circuit board 351 via a circuit 365 and battery electrical connector 366 as shown. In some implementations, electronics assembly 350 can include substrate 364 configured to secure (for example, adhesively secure) a portion of battery 308 to frame 391. Electronics assembly 350 can include a cover 363 configured to cover battery 308.

Hub 300 and electronics assembly 350 can include a number of resistors 367 that corresponds to the number of electrode(s) 202, 204 included in wearable device 100. A resistor 367 can be in an electrical path between each of electrode(s) 202, 204 and circuit board 351. Resistor(s) 367 can prevent or reduce damage to circuit board 351 (or other components of hub 300) due to shorting or arcing, which may be caused when high voltage is accidentally and/or suddenly introduced through electrode(s) 202, 204. For example, resistor(s) 367 can be high-capacity, low-resistance resistors that allow electrical signals related to a subject's cardiac activity to pass therethrough but inhibit high voltage from passing to circuit board 351 and/or other components of hub 300. As shown in FIG. 4K, resistor(s) can be encased by encasement 368. In some implementations, a magnetic plate 372 can be coupled to the second side 354 of circuit board 351. Such magnetic plate 372 can be configured to aid in connecting electrical contacts 378 with a charger (such as charger 400).

Circuit board 351 can include one or more holes 385 extending through circuit board 351 between first and second surfaces 353, 354 thereof. Thermally conductive probe 374, for example, first end 374*a* thereof, can be positioned adjacent second surface 354 and hole(s) 385. In some implementations, thermally conductive probe 374 can cover hole(s) 385. Temperature sensor 312*a* can be positioned adjacent first surface 353 and hole(s) 385. In some implementations, temperature sensor 312*a* can cover hole(s) 385. Hole(s) 385 can be configured to transmit thermal energy from thermally conductive probe 374 to temperature sensor 312*a*. For this, hole(s) 385 can include a thermally conductive material therein, such as copper.

FIG. 7A illustrates a cross-sectional view as identified in FIG. 1B of a portion of wearable device 100 (for example, hub 300 and dock 201) secured to subject 1 (for example, secured to the subject's skin). FIG. 7B illustrates a bottom perspective of the cross-sectional view as identified in FIG. 1B of a portion of wearable device 100 (for example, hub 300 and dock 201). FIG. 7A shows the thermally conductive path that is created from the subject's skin to temperature sensor 312*a* via substrate 294 (for example, the curved portion of substrate 294*b* that can be positioned between the subject's skin and thermally conductive probe 374), thermally conductive probe 374, and hole(s) 385. As discussed herein, hub 300 can include temperature sensors 312*b* and/or 312*c*, which can be spaced away from temperature sensor 312*a* and at least partially thermally isolated from temperature sensor 312*a* and/or the subject's skin. FIGS. 7A-7B also show how prong(s) 253, 254 (in this case a single prong 274 is shown) can electrically connect conductive strip(s) 273, 274 (in this case a single conductive strip 274 is shown) with electrical contacts 373, 374 (in this case a single electrical contact 377 is shown in FIG. 7B) when the hub 300 is secured to the dock 201.

Figures 8A, 8B, 8C:
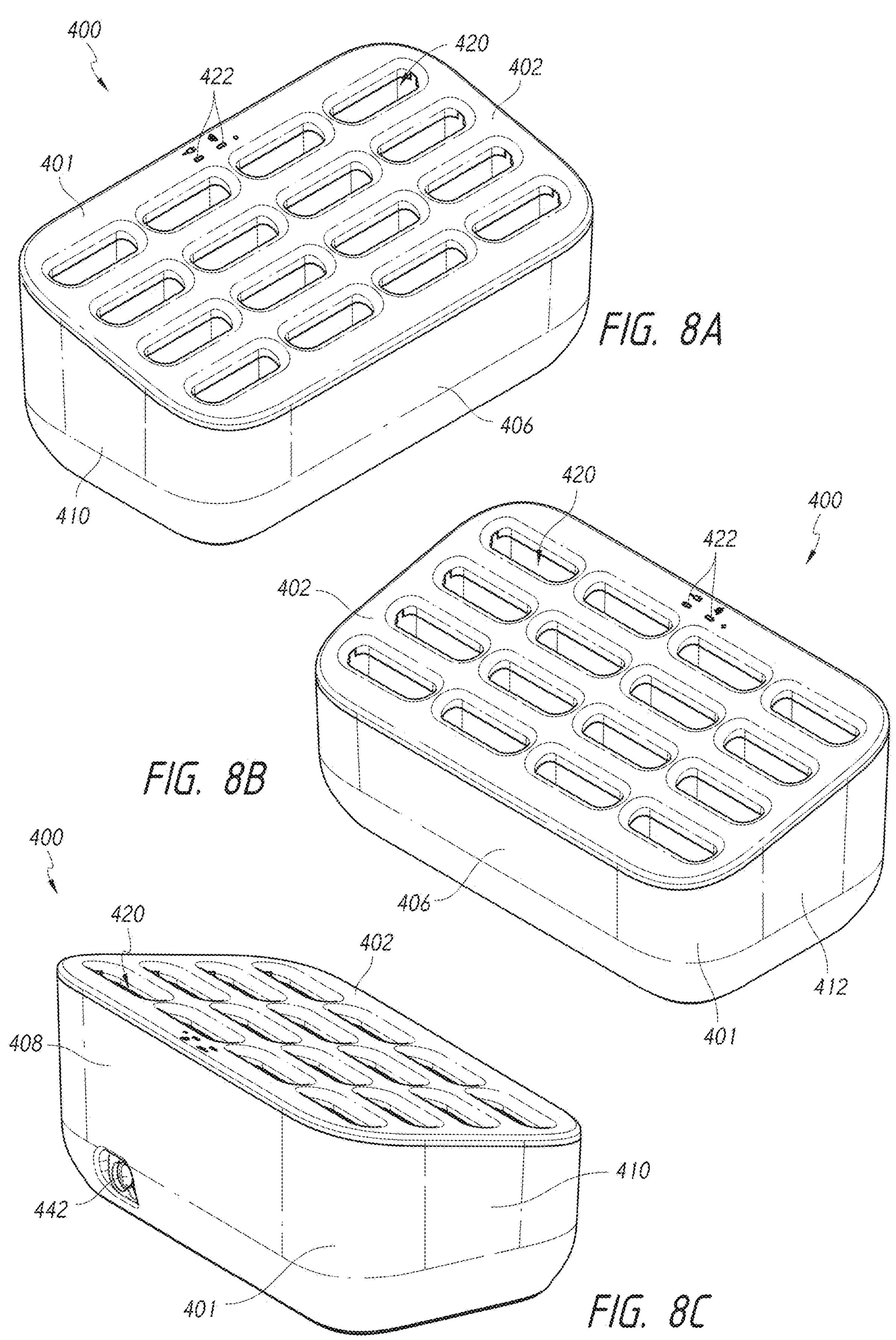
FIGS. 8A-8C illustrate top perspective views of a charger in accordance with aspects of this disclosure.
Figures 8D, 8E, 8F:
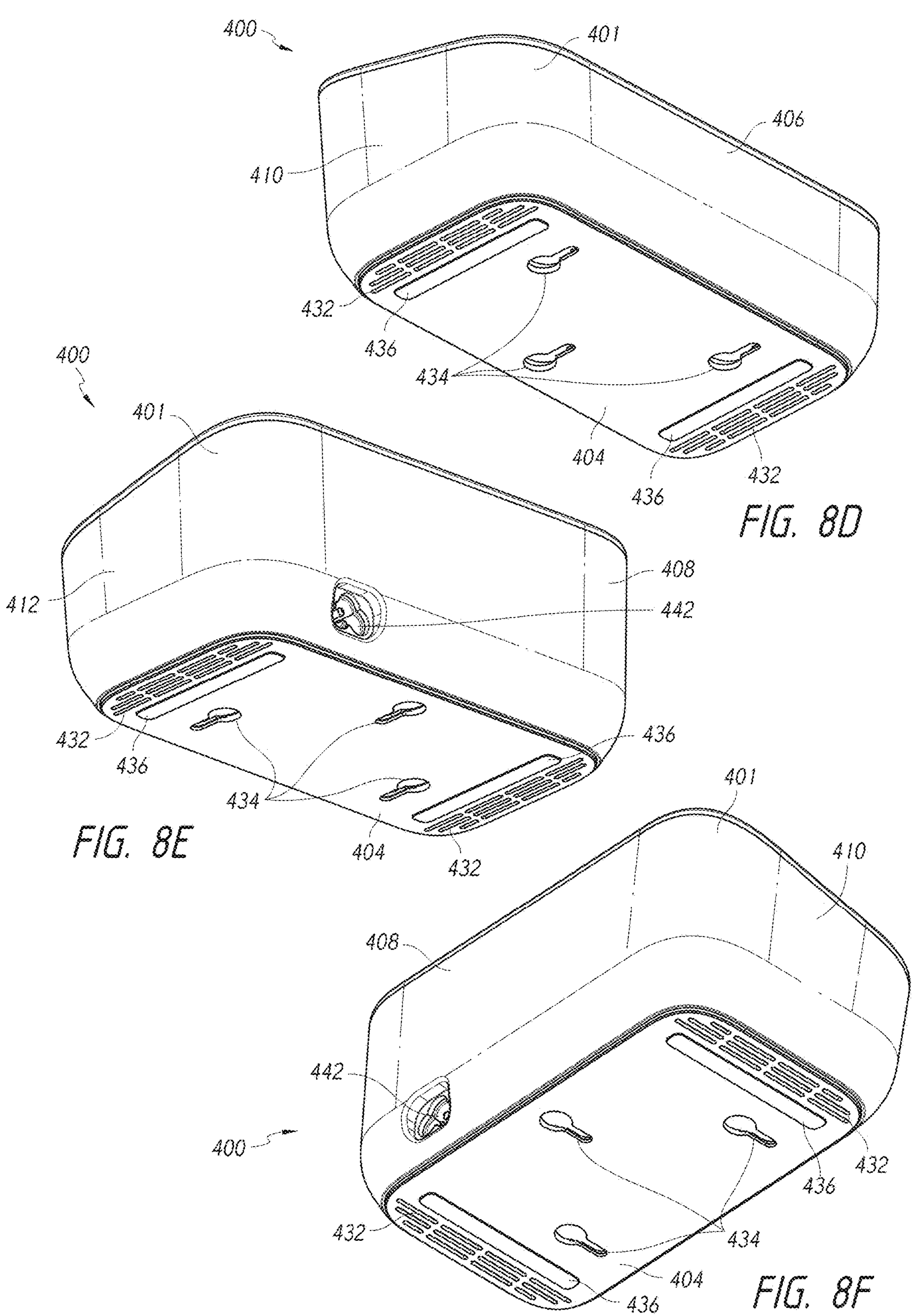
FIGS. 8D-8F illustrates bottom perspective views of the charger of FIGS. 8A-8C in accordance with aspects of this disclosure.
Figures 8G, 8H, 8I, 8J:
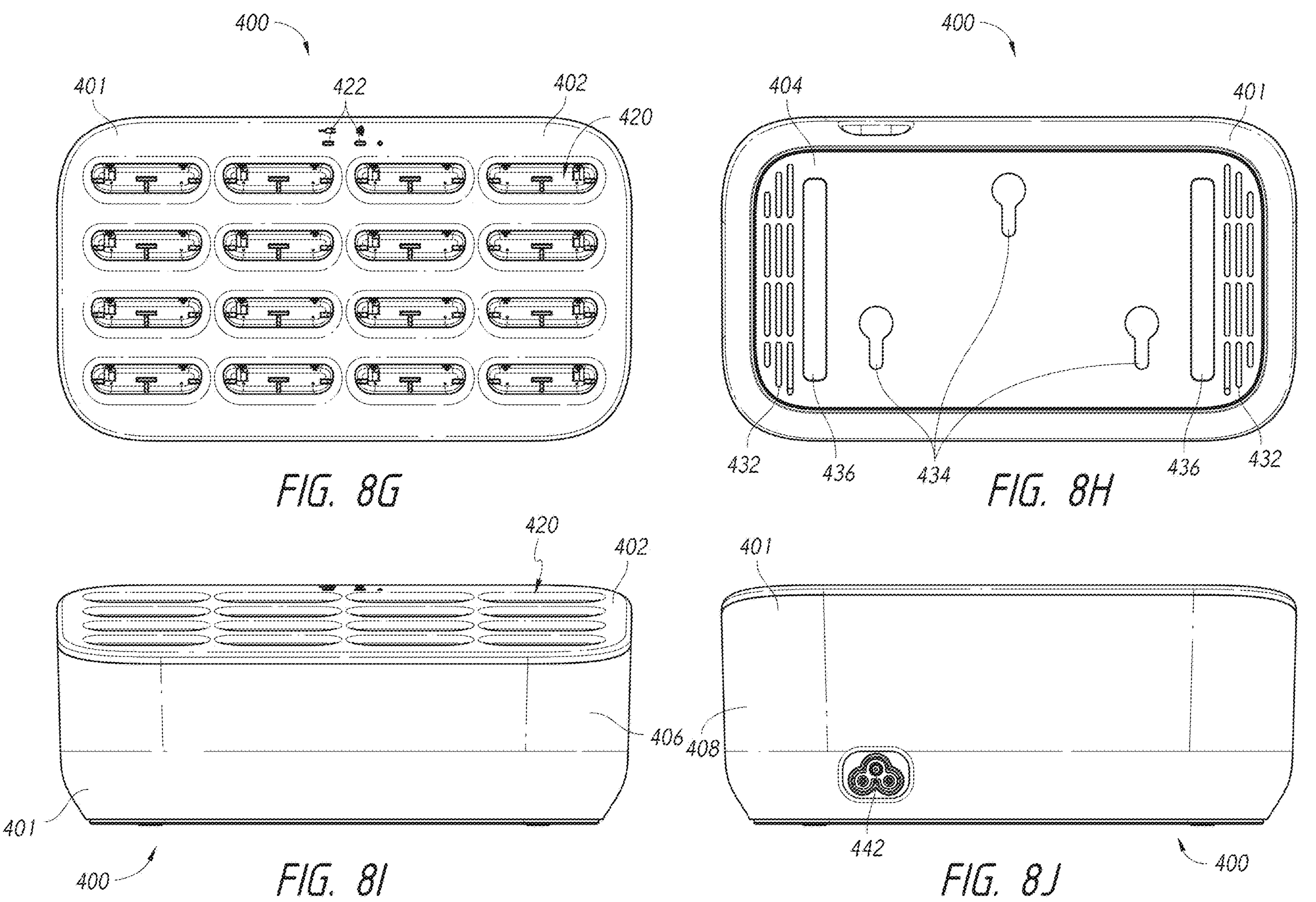
FIGS. 8G-8L illustrate a top view, a bottom view, a front view, a rear view, a first side view, and a second side view, respectively, of the charger of FIGS. 8A-8C in accordance with aspects of this disclosure.
Figures 8K, 8L, 8M, 8N:
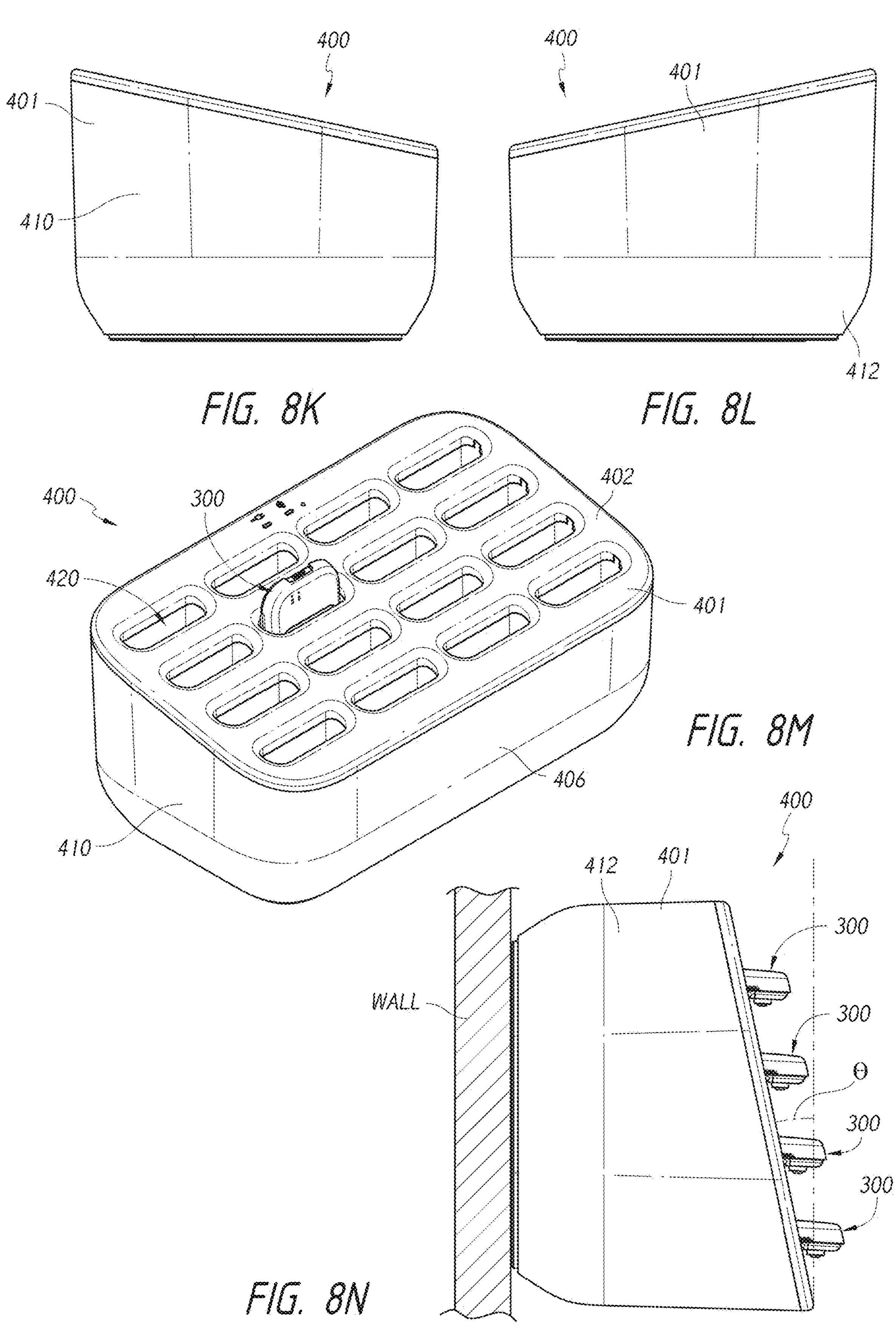
FIG. 8M illustrates a top perspective view of the charger of FIGS. 8A-8C with a hub positioned within a portion thereof in an example condition of use in accordance with aspects of this disclosure.
FIG. 8N illustrates a side view of the charger of FIGS. 8A-8C mounted to a wall with multiple hubs positioned within portions thereof in another example condition of use in accordance with aspects of this disclosure.

FIGS. 8A-8N illustrate various views of a charger 400. FIGS. 8A-8C illustrate top perspective views, FIGS. 8D-8F illustrate bottom perspective views, FIGS. 8G-8L illustrate a top view, a bottom view, a front view, a rear view, a first side view, and a second side view, respectively, of charger 400. FIG. 8M illustrates a top perspective view of charger 400 with a hub 300 positioned within a portion thereof in an example condition of use. FIG. 8N illustrates a side view of charger 400 mounted to a wall with multiple hubs 300 positioned within portions thereof in another example condition of use.

Charger 400 can include a main body 401 and can have a top 402, a bottom 404 opposite top 402, a front 406, a back 408 opposite front 406, a first side 410, and a second side 412 opposite first side 410. Front 406, back 408, first side 410, and second side 412 can extend from bottom 404. As shown, front 406, back 408, first side 410, and second side 412 can extend from bottom 404 at substantially right angles with respect to bottom 404, however such configuration is not intended to be limiting. Top 402 can be angled at an angle θ with respect to a plane that is substantially coplanar with bottom 404 as identified in FIG. 8N. Such angle θ can be between about 0 degrees and about 90 degrees, between about 5 degrees and about 50 degrees, or between about 10 degrees and about 30 degrees.

Charger 400 can include a plurality of charging cavities 420 (which can also be referred to herein as "charging ports"). Charging cavities 420 can extend inward from top 402 of main body 401. Each charging cavity 420 can be configured to receive at least a portion of hub 300 as described herein. Furthermore, each charging cavity 420 can be configured to charge battery 308 of hub 300 when hub 300 is inserted therein. Top 402 having angle θ with respect to a plane that is substantially coplanar with bottom 404 can advantageously position hub(s) 300 received by charging cavities 420 such that they can be easier to insert and/or remove from charger 400.

In some implementations, charging cavities 420 can include features configured to aid in securing a hub 300 at least partially therein and/or for aiding in making electrical contact therebetween. For example, charging cavities 420 can include one or more features that can receive ridge(s) 329 of hub 300 to operably position a hub 300 within a charging cavity 420. In some implementations, charging cavities 420 can include a magnet that can interact with magnetic plate 372 of hub 300 (when included) to aid in making electrical contact between a hub 300 and charging cavity 420.

As shown, charger 400 can include an array of charging cavities 420. For example, charger 400 can include 16 charging cavities 420 in a 4×4 array along top 402, however in some implementations charger 400 can be configured to have less than or more than 16 charging cavities 420 and/or have a different array configuration.

Charger 400 can include an electrical connection 442 configured to provide power to charger 400. Electrical connection 442 can be positioned along back 408. Charger 400 can include hardware to convert electrical energy received by a power source connected to electrical connection 442 to electrical energy appropriate for charging battery 308 of a hub 300 received by a charging cavity 420.

Charger 400 can include vent(s) 432 configured to manage the temperature within main body 401. Such vent(s) 432 can be positioned along bottom 404. Charger 400 can also include pad(s) 436 and/or mounting portions 434 positioned along bottom 404. As shown in FIG. 8N, such mounting portions 434 can be configured to allow charger 400 to be mounted to a wall.

Charger 400 can include one or more status indicators 422 configured to indicate a status of charger 400. For example, status indicators 422 can indicate a power status of charger 400, a charge status of one or more hubs 300 received by charger 400, and/or a connectivity status of charger 400 (for example, a wireless connectivity of charger 400). Such status indicators 422 can be positioned along top 402.

In some implementations, charger 400 can function as a hub that can wirelessly transmit data between charger 400 and one or more external devices and/or systems. For example, charger 400 can function as a hub that can transmit data (such as physiological data of a subject) from a hub 300 connected to the charger 400 via a charging cavity 420. Such data can be displayed on a display and/or imported into a subject's medical records, for example.

Although various implementations of the wearable device 100 have been disclosed as including electrode(s) 204 and cable(s) 203 (for example, as part of dock assembly 200), in some variants, wearable device 100 does not include such electrode(s) 204 and cable(s) 203, yet still includes, for example, hub 300 and dock 201 with any of the features described herein with respect to these components

ADDITIONAL CONSIDERATIONS AND TERMINOLOGY

Although this invention has been disclosed in the context of certain preferred implementations, it should be understood that certain advantages, features and aspects of the systems, devices, and methods may be realized in a variety of other implementations. Additionally, it is contemplated that various aspects and features described herein can be practiced separately, combined together, or substituted for one another, and that a variety of combination and subcombinations of the features and aspects can be made and still fall within the scope of the invention. Furthermore, the systems and devices described above need not include all of the modules and functions described in the preferred implementations.

Conditional language used herein, such as, among others, "can," "could," "might," "may," "e.g.,", "for example," and the like, unless specifically stated otherwise, or otherwise understood within the context as used, is generally intended to convey that certain features, elements, and/or steps are optional. Thus, such conditional language is not generally intended to imply that features, elements, and/or steps are in any way required or that one or more implementations necessarily include logic for deciding, with or without other input or prompting, whether these features, elements, and/or steps are included or are to be always performed. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain implementations require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain implementations, the terms "generally parallel" and "substantially parallel" refer to a value, amount, or characteristic that departs from exactly parallel by less than or equal to 10 degrees, 5 degrees, 3 degrees, or 1 degree. As another example, in certain implementations, the terms "generally perpendicular" and "substantially perpendicular" refer to a value, amount, or characteristic that departs from exactly perpendicular by less than or equal to 10 degrees, 5 degrees, 3 degrees, or 1 degree.

Although certain implementations and examples have been described herein, it will be understood by those skilled in the art that many aspects of the systems and devices shown and described in the present disclosure may be differently combined and/or modified to form still further implementations or acceptable examples. All such modifications and variations are intended to be included herein within the scope of this disclosure. A wide variety of designs and approaches are possible. No feature, structure, or step disclosed herein is essential or indispensable.

Any methods disclosed herein need not be performed in the order recited. The methods disclosed herein may include certain actions taken by a practitioner; however, they can also include any third-party instruction of those actions, either expressly or by implication.

The methods and tasks described herein may be performed and fully automated by a computer system. The computer system may, in some cases, include multiple distinct computers or computing devices (for example, physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (for example, solid state storage devices, disk drives, etc.). The various functions disclosed herein may be embodied in such program instructions, and/or may be implemented in application-specific circuitry (for example, ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. The computer system may be a cloud-based computing system whose processing resources are shared by multiple distinct business entities or other subjects.

Depending on the implementation, certain acts, events, or functions of any of the processes or algorithms described herein can be performed in a different sequence, can be added, merged, or left out altogether (for example, not all described operations or events are necessary for the practice of the algorithm). Moreover, in certain implementations, operations or events can be performed concurrently, for example, through multi-threaded processing, interrupt processing, or multiple processors or processor cores or on other parallel architectures, rather than sequentially.

Various illustrative logical blocks, modules, routines, and algorithm steps that may be described in connection with the disclosure herein can be implemented as electronic hardware (for example, ASICs or FPGA devices), computer software that runs on general purpose computer hardware, or combinations of both. Various illustrative components, blocks, and steps may be described herein generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, various illustrative logical blocks and modules that may be described in connection with the disclosure herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. A processor can include an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of any method, process, routine, or algorithm described in connection with the disclosure herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor such that the processor can read information from, and write information to, the storage medium. In the alternative, the storage medium can be integral to the processor. The processor and the storage medium can reside in an ASIC. The ASIC can reside in a subject terminal. In the alternative, the processor and the storage medium can reside as discrete components in a subject terminal.

While the above detailed description has shown, described, and pointed out novel features, it can be understood that various omissions, substitutions, and changes in the form and details of the devices or algorithms illustrated can be made without departing from the spirit of the disclosure. As can be recognized, certain portions of the description herein can be embodied within a form that does not provide all of the features and benefits set forth herein, as some features can be used or practiced separately from others. The scope of certain implementations disclosed herein is indicated by the appended claims rather than by the foregoing description. All changes which come within the meaning and range of equivalency of the claims are to be embraced within their scope.

What is claimed is:

1. A wearable device comprising:
- a dock comprising:
  - one or more substrates configured to be secured to skin of a subject;
  - a frame coupled to the one or more substrates, the frame comprising a plurality of prongs;
  - a dock circuit layer comprising a plurality of conductive strips positioned along the plurality of prongs of the frame;
- a plurality of electrodes for monitoring cardiac activity of the subject; and
- a plurality of cables configured to facilitate electrical communication between the plurality of electrodes and the dock circuit layer; and
- a hub configured to be removably secured to the dock, the hub comprising:
  - a housing comprising an interior and a plurality of openings;
  - a hub circuit layer arranged within the interior of the housing; and
  - one or more hardware processors coupled to the hub circuit layer;
- wherein, when the hub and dock are secured to one another, the plurality of prongs of the frame extend towards the plurality of openings of the housing of the hub and cause the plurality of conductive strips to contact portions of the hub circuit layer to facilitate electrical communication between the plurality of electrodes and the hub circuit layer.

2. The wearable device of claim 1, wherein, when the hub and dock are secured to one another, the plurality of prongs of the frame extend at least partially through the plurality of openings of the housing of the hub and cause the plurality of conductive strips to contact said portions of the hub circuit layer.

3. The wearable device of claim 2, wherein:
- each of the plurality of prongs comprises a first end connected to a portion of the frame, a second end opposite said first end, and a curved portion that is closer to said second end than to said first end; and
- when the hub and dock are secured to one another, said curved portions of the plurality of prongs extend at least partially through the plurality of openings of the housing of the hub and cause the plurality of conductive strips to contact portions of the hub circuit layer.

4. The wearable device of claim 2, wherein:

each of the plurality of prongs comprises a first end connected to a portion of the frame, a second end opposite said first end, a convex portion, and a concave portion;

said convex portion is closer to said first end than said concave portion;

said concave portion is closer to said second end than said convex portion; and when the hub and dock are secured to one another, said concave portions of the plurality of prongs extend at least partially through the plurality of openings of the housing of the hub and cause the plurality of conductive strips to contact portions of the hub circuit layer.

5. The wearable device of claim 4, wherein said concave portion:

comprises a smaller amount of a length of each of said plurality of prongs;

is shorter than said convex portion; and/or has a smaller radius of curvature than said convex portion.

6. The wearable device of claim 4, wherein each of the plurality of prongs comprises a bump on said concave portion, said bumps of the plurality of prongs configured to facilitate contact between the plurality of conductive strips and the portions of the hub circuit layer.

7. The wearable device of claim 1, wherein the hub is configured to removably secure to the frame of the dock, wherein the frame includes at least one mechanical connector configured to secure to at least one mechanical connector of the hub.

8. The wearable device of claim 1, wherein each of the plurality of prongs comprises a bump, said bumps of the plurality of prongs configured to facilitate contact between the plurality of conductive strips and the portions of the hub circuit layer.

9. The wearable device of claim 1, wherein said plurality of electrodes are external electrodes configured to be secured to the subject's skin away from the dock, and wherein the wearable device further comprises at least one internal electrode operably positioned by the frame of the dock.

10. The wearable device of claim 9, wherein the wearable device comprises two internal electrodes spaced from one another and operably positioned by the frame of the dock.

11. The wearable device of claim 10, wherein the one or more substrates comprises two substrates separated by a channel, wherein each of the two substrates are associated with a different one of the two internal electrodes, and wherein said channel provides electrical isolation between the two internal electrodes.

12. The wearable device of claim 11, wherein each of the two substrates are configured to be positioned between their respective internal electrode and the subject's skin.

13. The wearable device of claim 1, wherein the one or more substrates are electrically and/or thermally conductive.

14. The wearable device of claim 1, wherein the housing further comprises a plurality of inwardly tapered recesses, each of the plurality of inwardly tapered recesses surrounding a different one of the plurality of openings.

15. The wearable device of claim 1, wherein the hub further comprises one or more electrical contacts coupled to the hub circuit layer and configured to allow a battery of the hub to receive power from a charging device, and wherein the housing comprises one or more charger contact openings configured to provide access to said one or more electrical contacts.

16. The wearable device of claim 1, wherein the hub further comprises a temperature sensor.

17. The wearable device of claim 1, wherein:

said plurality of openings of the housing of the hub are prong openings of the housing;

said housing further comprises a top portion, a bottom portion, and a probe opening extending through said bottom portion, said bottom portion positioned closer to the subject's skin when the hub and dock are secured to one another and the dock is secured to the subject's skin;

said hub circuit layer is a circuit board, said circuit board comprising a first surface, a second surface, and at least one hole extending through the circuit board between the first and second surfaces; and said hub further comprises:

a temperature sensor mounted to the first surface of the circuit board adjacent said at least one hole;

a thermally conductive probe extending through said probe opening of the housing, the thermally conductive probe comprising a first end and a second end opposite the first end, the first end positioned adjacent the second surface of the circuit board and said at least one hole; and when the hub and the dock are secured to one another:

the second end of the thermally conductive probe contacts at least one of said one or more substrates of the dock; and the thermally conductive probe is configured to receive thermal energy emanating from the subject's skin through the one or more substrates and transmit said thermal energy towards said temperature sensor via the at least one hole of the circuit board when the dock is secured to the subject's skin.

18. The wearable device of claim 17, wherein the hub further comprises a wall extending outward from the bottom portion of the housing and extending around at least a portion of the thermally conductive probe.

19. The wearable device of claim 18, wherein the wall surrounds an entire cross-section of the thermally conductive probe.

20. The wearable device of claim 18, wherein the wall surrounds an entire perimeter of the thermally conductive probe.

21. The wearable device of claim 18, wherein the wall encircles the thermally conductive probe.

22. The wearable device of claim 18, wherein the thermally conductive probe extends beyond the wall.

23. The wearable device of claim 22, wherein less than about 30% of a length of the thermally conductive probe extends beyond the wall.

24. The wearable device of claim 22, wherein the thermally conductive probe extends beyond the wall an amount that is less than about 1.5 mm.

25. The wearable device of claim 22, wherein the thermally conductive probe extends beyond the wall an amount that is between about 0.2 mm and about 1.5 mm.

26. The wearable device of claim 22, wherein the wall is cylindrical and the thermally conductive probe is cylindrical.

27. The wearable device of claim 22, wherein a gap between the thermally conductive probe and the wall is between about 0.2 mm and about 1.5 mm.

* * * * *